(12) United States Patent
Achen et al.

(10) Patent No.: US 7,846,437 B2
(45) Date of Patent: Dec. 7, 2010

(54) CHIMERIC ANTI-VEGF-D ANTIBODIES AND HUMANIZED ANTI-VEGF-D ANTIBODIES AND METHODS OF USING SAME

(75) Inventors: Marc Gregory Achen, Parkville (AU); Steven Alan Stacker, Parkville (AU); Christoph Renner, Homburg/Saar (DE)

(73) Assignee: Vegenics Limited, Toorak (AU)

( * ) Notice: Subject to any disclaimer, the term of this patent is extended or adjusted under 35 U.S.C. 154(b) by 0 days.

(21) Appl. No.: 12/165,446

(22) Filed: Jun. 30, 2008

(65) Prior Publication Data

US 2009/0155252 A1 Jun. 18, 2009

Related U.S. Application Data

(63) Continuation of application No. 11/074,373, filed on Mar. 7, 2005, now abandoned.

(60) Provisional application No. 60/550,441, filed on Mar. 5, 2004.

(51) Int. Cl.
*A61K 39/395* (2006.01)
*C12P 21/08* (2006.01)

(52) U.S. Cl. ............... 424/133.1; 424/141.1; 424/145.1

(58) Field of Classification Search ........................ None
See application file for complete search history.

(56) References Cited

U.S. PATENT DOCUMENTS

| | | | |
|---|---|---|---|
| 4,946,778 A | 8/1990 | Ladner et al. | |
| 5,530,101 A | 6/1996 | Queen et al. | |
| 5,585,089 A | 12/1996 | Queen et al. | |
| 5,607,918 A | 3/1997 | Eriksson et al. | |
| 5,693,762 A | 12/1997 | Queen et al. | |
| 5,840,693 A | 11/1998 | Eriksson et al. | |
| 5,919,899 A | 7/1999 | Persico et al. | |
| 5,928,939 A | 7/1999 | Eriksson et al. | |
| 6,130,071 A | 10/2000 | Alitalo et al. | |
| 6,221,839 B1 | 4/2001 | Alitalo et al. | |
| 6,235,713 B1 | 5/2001 | Achen et al. | |
| 6,245,530 B1 | 6/2001 | Alitalo et al. | |
| 6,331,301 B1 | 12/2001 | Eriksson et al. | |
| 6,361,946 B1 | 3/2002 | Alitalo et al. | |
| 6,383,484 B1 | 5/2002 | Achen et al. | |
| 6,403,088 B1 | 6/2002 | Alitalo et al. | |
| 6,645,933 B1 | 11/2003 | Alitalo et al. | |
| 7,097,986 B2 * | 8/2006 | Achen et al. | ............... 435/7.1 |
| 7,122,654 B2 * | 10/2006 | Achen et al. | ............... 536/23.5 |
| 7,410,639 B2 * | 8/2008 | Achen et al. | ............. 424/130.1 |
| 7,534,572 B2 * | 5/2009 | Achen et al. | ............... 435/7.1 |
| 7,662,932 B2 * | 2/2010 | Achen et al. | ............... 530/399 |
| 2003/0113870 A1 | 6/2003 | Ferrara et al. | |
| 2005/0282233 A1 * | 12/2005 | Eriksson et al. | ............... 435/7.2 |
| 2006/0030000 A1 | 2/2006 | Alitalo et al. | |

FOREIGN PATENT DOCUMENTS

| | | |
|---|---|---|
| EP | 9519928.7 | 9/1995 |
| EP | 9612368.2 | 6/1996 |
| EP | 0935001 | 8/1999 |
| JP | 8-185216 | 7/1996 |
| WO | WO-93/11236 | 6/1993 |
| WO | WO-96/11269 | 4/1996 |
| WO | WO-96/26736 | 9/1996 |
| WO | WO-97/05250 | 2/1997 |
| WO | WO-97/12972 | 4/1997 |
| WO | WO-98/02543 | 1/1998 |
| WO | WO-98/07832 | 2/1998 |
| WO | WO-98/33917 | 8/1998 |
| WO | WO00/18212 | 4/2000 |
| WO | WO-00/21560 | 4/2000 |
| WO | WO-00/25805 | 5/2000 |
| WO | WO-00/27879 | 5/2000 |
| WO | WO00/37025 | 6/2000 |
| WO | WO-02/060950 | 8/2002 |

OTHER PUBLICATIONS

De Pascalis et al, Journal of Immunology 169: 3076-3084, 2002.*
Vajdos et al, J. Mol. Biol. 320: 415-428, 2002.*
Holm et al, Mol. Immunol. 44: 1075-1084, 2007.*
Chen, J. Mol. Biol. 293: 865-881, 1999.*
U.S. Appl. No. 11/692,774, Achen et al.
U.S. Appl. No. 11/692,753, Achen et al.
U.S. Appl. No. 11/772,089, Achen et al.
Achen et al., "Monoclonal antibodies to vascular endothelial growth factor-D block its interactions with both VEGF receptor-2 and VEGF receptor-3," *Eur. J. Biochem.*, 267:2505-2515 (2000).
Achen et al., "Vascular endothelial growth factor D (VEGF-D) is a ligand for the tyrosine kinases VEGF receptor 2 (Flk1) and VEGF receptor 3 (Flt4)," *Proc. Natl. Acad. Sci. USA*, 95:548-553 (1998).
Barrios et al., "Length of the antibody heavy chain complementarily determining region 3 as a specificity-determining factor," *J. Mol. Recognition*, 17:332-8 (2004).
Breiteneder-Geleff et al., "Angiosarcomas experss mixed endothelial phenotypes of blood and lymphatic capillaries," *Am. J. Pathol.*, 154:385-394 (1999).
Cao et al., "Vascular endothelial growth factor C induces angiogenesis in vivo," *Proc. Natl. Acad. Sci. USA*, 95:14389-14394, 1998.
Chomczynski et al., "Single-step method of RNA isolation by acid guanidinium thiocyanate-phenol-chloroform extraction," *Anal. Biochem.*, 162:156-159 (1987).
Cobleigh et al., "A phase I/II dose-escalation trial of bevacizumab in previously treated metastatic breast cancer," *Seminars in Oncology*, 30(Suppl 16):117-124 (2003).
Dumont et al., "Cardiovascular failure in mouse embryos deficient in VEGF receptor-3," *Science*, 282:946-949 (1998).

(Continued)

*Primary Examiner*—Phuong Huynh
(74) *Attorney, Agent, or Firm*—Marshall, Gerstein & Borun LLP

(57) ABSTRACT

The present invention relates to materials and methods for modulating angiogenesis and lymphangiogenesis. The compositions of the invention provide chimeric and/or humanized VEGF-D antibody substances, antibodies, polypeptides and fragments thereof useful for modulating angiogenesis and lymphangiogenesis in a subject.

4 Claims, 12 Drawing Sheets

OTHER PUBLICATIONS

Dumont et al., "Vascularization of the mouse embryo: a study of flk-1, tek, tie, and vascular endothelial growth factor expression during development," *Developmental Dynamics*, 203:80-92 (1995).

Ferrara, "Molecular and biological properties of vascular endothelial growth factor," *J. Mol. Med.*, 77:527-543 (1999).

Folkman et al., "Angiogenesis," *J. Biol. Chem.*, 267:10931-10934 (1992).

Fong et al., "Regulation of flt-1 expression during mouse embryogenesis suggests a role in the establishment of vascular endothelium," *Developmental Dynamics*, 207:1-10 (1996).

Fong et al., "Role of the Flt-1 receptor tyrosine kinase in regulating the assembly of vascular endothelium," *Nature*, 376:66-70 (1995).

Hiratsuka et al., "Flt-1 lacking the tyrosine kinase domain is sufficient for normal development and angiogenesis in mice," *Proc. Natl. Acad. Sci. USA*, 95:9349-9354 (1998).

Jeltsch et al., "Hyperplasia of lymphatic vessels in VEGF-C transgenic mice," *Science*, 276:1423-1425 (1997).

Jones et al., "Replacing the complementarity-determining regions in a human antibody with those from a mouse," *Nature*, 321:522-525 (1986).

Joukov et al., "A novel vascular endothelial growth factor, VEGF-C, is a ligand for the Flt4 (VEGR-3) and KDR (VEGFR-2) receptor tyrosine kinases," *The EMBO J.*, 15:290-298 (1996).

Jussila et al., "Lymphatic endothelium and kaposi's sarcoma spindle cells detected by antibodies against the vascular endothelial growth factor receptor-3," *Cancer Research*, 58:1955-1604 (1998).

Kaipainen et al., "Enhanced expression of the tie receptor tyrosine kinase messenger RNA in the vascular endothelium of metastatic melanomas," *Cancer Research*, 54:6571-6577 (1994).

Kaipainen et al., "Expression of the fms-like tyrosine kinase 4 gene becomes restricted to lymphatic endothelium during development," *Proc. Natl. Acad. Sci. USA*, 9:3566-3570 (1995).

Kaipainen et al., "The related FLT4,FLT1, and KDR receptor tyrosine kinases show distinct expression patterns in human fetal endothelial cells," *J. Exp. Med.*, 178:2077-2088 (1993).

Karpanen et al., "Vascular endothelial growth factor C promotes tumor lymphangiogenesis and intralymphatic tumor growth," *Cancer Research*, 61:1786-1790 (2001).

Kobrin et al., "A V region mutation in a phosphocholine-binding monoclonal antibody results in loss of antigen binding," *J. Immunol.*, 146:2017-20 (1991).

Kortt et al., "Dimeric and trimeric antibodies: high avidity scFvs for cancer targeting," *Biomol. Eng..*, 18:95-108 (2001).

Kozak, "An analysis of 5'-noncoding sequences from 699 vertebrate messenger RNAs," *Nucleic Acids Research*, 15:8125-8148 (1987).

Kyte et al., "A simple method for displaying the hydropathic character ofa protein," *J. Mol. Biol.*, 157:105-132 (1982).

Layton et al., "Neutralising antibodies to the granulocyte colony-stimulating factor receptor recognise both teh immunoglobulin-like domain and the cytokine receptor homologous domain," *Growth Factors*, 14:117-130 (1997).

MacCallum et al., "Antibody-antigen interactions: contact analysis and binding site topography," *J. Mol. Biol.*, 262:732-45 (1996).

Marconcini et al., "C-fos-indused growth factor/vascular endothelial growth factor D induces angiogenesis in vivo and in vitro," *Proc. Natl. Acad. Sci. USA*, 96:9671-9676 (1999).

Meissner et al., "Transient gene expression: recombinant protein production with suspension-adapted HEK293-EBNA cells," *Biotechnol. Bioeng.*, 75:197-203 (2001).

Meyer et al., "A novel vascular endothelial growth factor encoded by Orf virus, VEGF-E, mediates angiogenesis via signalling through VEGFR-2 (KDR) but not VEGFR-1 (Flt-1) receptor tyrosine kinases," *The Embo J.*, 18:363-374 (1999).

Muller et al., "The crystal structure of vascular endothelial growth factor (VEGF) refined to 1.93 A resolution: multiple copy flexibility and receptor binding," *Structure*, 5:1325-1338 (1997).

Neufeld et al., "Vascular endothelial growth factor (VEGF) and its receptors," *FASEB J.*, 13:9-22 (1999).

Oelrichs et al., "NYK/FLK-1: a putative receptor protein tyrosine kinase isolated from E10 embryonic neuroepithelium is expressed in endothelial cells of the developing embryo," *Oncogene*, 8:11-18 (1992).

Oh et al., "VEGF and VEGF-C: specific induction of angiogenesis and lymphangiogenesis in the differentiated avian chorioallantoic membrance," *Dev. Biol.*, 188:96-109 (1997).

Owens et al., "The genetic engineering of monoclonal antibodies," *J. Immunol. Meth.*, 168:149-165 (1994).

Partanen et al., "Lack of lymphatic vascular specificity of vascular endothelial growth factor receptor 3 in 185 vascular tumors," *Cancer*, 86:2406-2412 (1999).

Prevo et al., "Mouse LYVE-1 is an endocytic receptor for hyaluronan in lymphatic endothelium," *J. Biol. Chem.*, 276:19420-19430 (2001).

Renner et al., "Differential mRNA display at the single-cell level," *Biotechniques*, 24:720-722 (1998).

Renner et al., "The role of lymphocyte subsets and adhesion molecules in T cell-dependent cytotoxicity mediated by CD3 and CD28 bispecific monoclonal antibodies," *Eur. J. Immunol.*, 25:2027-2033 (1995).

Riechmann et al., "Reshaping human antibodies for therapy," *Nature*, 332::323-327 (1977).

Rissanen et al., "VEGF-D is the strongest angiogenic and lymphangiogenic effector among VEGFs delivered into skeletal muscle via adenoviruses," *Circ. Res.*, 92:1098-1106 (2003).

Rockson, "Lymphedema," *Am. J. Med.*, 110:228-295 (2001).

Rudikoff et al., "Single amino acid substitution altering antigen-binding specificity," *Proc. Natl. Acad. Sci. USA*, 79:1979-83 (1982).

Shalaby et al., "A requirement for Flk1 in primitive and definitive hematopoiesis and vasculogenesis," *Cell*, 89:981-990 (1997).

Shalaby et al., "Failure of blood-island formation and vasculogenesis in Flk-1-deficient mice," *Nature*, 376:62-66 (1995).

Skobe et al., "Induction of tumor lymphangiogenesis by VEGF-C promotes breast cancer metastasis," *Nature Medicine*, 7:192-198 (2001).

Soker et al., "Neuropilin-1 is experssed by endothelial and tumor cells as an isoform-specific receptor for vascular endothelial growth factor," *Cell*, 92:735-745 (1998).

Stacker et al., "A mutant form of vascular endothelial growth factor (VEGF) that lacks VEGF receptor-2 activation retains the ability to induce vascular permeability," *J. Biol. Chem.*, 274:34884-34892 (1999).

Stacker et al., "Biosynthesis of vascular endothelial growth factor-D involves proteolytic processing which generates non-covalent homodimers," *J. Biol. Chem.*, 274:32127-32136 (1999).

Stacker et al., "The vascular endothelial growth factor family: signalling for vascular development," *Growth Factors*, 17:1-11 (1999).

Stacker et al., "VEGF-D promotes the metastatic spread of tumor cells via the lymphatics," *Nature Medicine*, 7:186-191 (2001).

Stryer, Biochemistry, 3rd edition, New York, NY: W.H. Freeman Company, pp. 31-33 (1998).

Taipale et al., "Vascular endothelial growth factor receptor-3," *Curr. Topics Micro. Immunol.*, 237:85-96 (1999).

Todorovska et al., "Design and application of diabodies, triabodies and tetrabodies for cancer targeting," *J. Immunol. Methods*, 248:47-66 (2001).

Veikkola et al., "Signalling via vascular endothelial growth factor receptor-3 is sufficient for lymphangiogenesis in transgenic mice," *The EMBO J.*, 20:1223-1231 (2001).

Verhoeyen et al., "Reshaping human antibodies: grafting an antilysozyme activity," *Science*, 239:1534-1536 (1998).

Witte et al., "lymphangiogenesis: mechanisms, signficance and clinical implications," in *Regulation of Angiogenesis* (ed., Goldberg), Basel, Switzerland: Birkhauser Verlag (1997).

Witzenbichler et al., "Vascular endothelial growth factor-C (VEGF-C/VEGF-2) promotes angiogenesis in the setting of tissue ischemia," *Am. J. Pathol.*, 153:381-394 (1998).

Wu et al., "Humanization of a murine monoclonal antibody by simultaneous optimization of framework and CDR residues," *J. Mol. Biol.*, 294:151-62 (1999).

Yang et al., "A randomized trial of bevacizumab, an anti-vascular endothelial growth factor antibody, for metastatic renal cancer," *N. Engl. J. Med.*, 349:427-434 (2003).

\* cited by examiner

FIGURE 1

A. Anti-VEGF-D light chain variable region

```
atgaagttgcctgttaggctgttggtgctgatgttctggattcctgcttccagcagtgat
 M   K   L   P   V   R   L   L   V   L   M   F   W   I   P   A   S   S   S   D
tttgtgatgacccaaactccactctcctgcctgtcagtcttggagatcaagcctccatc
 F   V   M   T   Q   T   P   L   S   L   P   V   S   L   G   D   Q   A   S   I
tcttgcagatctagtcagagccttgtacacagtaatggaaacacctatttacattggtac
 S   C   R   S   S   Q   S   L   V   H   S   N   G   N   T   Y   L   H   W   Y
ctgcagaagccaggccagtctccaaagctcctgatctacaaagtttccaaccgattttct
 L   Q   K   P   G   Q   S   P   K   L   L   I   Y   K   V   S   N   R   F   S
ggggtcccagacaggttcagtggcagtggatcagggacagatttcacactcaagatcagc
 G   V   P   D   R   F   S   G   S   G   S   G   T   D   F   T   L   K   I   S
agagtggaggctgaggatctgggagtttatttctgctctcaaagtacacatgttcctcgg
 R   V   E   A   E   D   L   G   V   Y   F   C   S   Q   S   T   H   V   P   R
                                                           BamHI
acgttcggtggaggcaccaagctggaaatcaaagagtGGATCC
 T   F   G   G   G   T   K   L   E   I   K
```

B. Anti-VEGF-D heavy chain variable region

```
atgggatggagcggggtctttctcttcctcctgtcaggaagtacaggtgtccactctgag
 M   G   W   S   G   V   F   L   F   L   L   S   G   S   T   G   V   H   S   E
atccagctacagcagtctggacctgacctggtgaagcctggggcttcggtgaaggtatcc
 I   Q   L   Q   Q   S   G   P   D   L   V   K   P   G   A   S   V   K   V   S
tgcagggcttctggttactcattcactggctacaacatgtactgggtgaagcagagccat
 C   R   A   S   G   Y   S   F   T   G   Y   N   M   Y   W   V   K   Q   S   H
ggaaagagccttgagtggattggatatattgatccttacaatggtgatactacctacaac
 G   K   S   L   E   W   I   G   Y   I   D   P   Y   N   G   D   T   T   Y   N
cagaagttcaagggcaaggccacattgactgttgacaagtcctccagcacagccttcatg
 Q   K   F   K   G   K   A   T   L   T   V   D   K   S   S   S   T   A   F   M
catctcaacagcctgacatctgaggactctgcagtctattactgtgcaaggacctcctat
 H   L   N   S   L   T   S   E   D   S   A   V   Y   Y   C   A   R   T   S   Y
tatggaggtatggactactggggtcaaggaacctcagtcaccgtctcctcagcaggtgag
 Y   G   G   M   D   Y   W   G   Q   G   T   S   V   T   V   S   S BamHI
    tGGATCC
```

FIGURE 2

*The destroyed internal vector BamHI site is high-lighted in bold and underlined pEAK8 human light chain vector

```
GGCGTAATCTGCTGCTTGCAAACAAAAAAACCACCGCTACCAGCGGTGGT
TTGTTTGCCGGATCAAGAGCTACCAACTCTTTTTCCGAAGGTAACTGGCT
TCAGCAGAGCGCAGATACCAAATACTGTCCTTCTAGTGTAGCCGTAGTTA
GGCCACCACTTCAAGAACTCTGTAGCACCGCCTACATACCTCGCTCTGCT
AATCCTGTTACCAGTGGCTGCTGCCAGTGGCGATAAGTCGTGTCTTACCG
GGTTGGACTCAAGACGATAGTTACCGGATAAGGCGCAGCGGTCGGGCTGA
ACGGGGGGTTCGTGCACACAGCCCAGCTTGGAGCGAACGACCTACACCGA
ACTGAGATACCTACAGCGTGAGCATTGAGAAAGCGCCACGCTTCCCGAAG
GGAGAAAGGCGGACAGGTATCCGGTAAGCGGCAGGGTCGGAACAGGAGAG
CGCACGAGGGAGCTTCCAGGGGGAAACGCCTGGTATCTTTATAGTCCTGT
CGGGTTTCGCCACCTCTGACTTGAGCGTCGATTTTTGTGATGCTCGTCAG
GGGGGCGGAGCCTATGGAAAAACGCCAGCAACGCAAGCTAGAGTTTAAAC
TTGACAGATGAGACAATAACCCTGATAAATGCTTCAATAATATTGAAAAA
GGAAAAGTATGAGTATTCAACATTTCCGTGTCGCCCTTATTCCCTTTTTT
GCGGCATTTTGCCTTCCTGTTTTTGCTCACCCAGAAACGCTGGTGAAAGT
AAAAGATGCAGAAGATCACTTGGGTGCGCGAGTGGGTTACATCGAACTGG
ATCTCAACAGCGGTAAGATCCTTGAGAGTTTTCGCCCCGAAGAACGTTTC
CCAATGATGAGCACTTTTAAAGTTCTGCTATGTGGCGCGGTATTATCCCG
TATTCTTGGTTGAATACTCACCAGTCACAGAAAAGCATCTTACGGATGGC
ATGACAGTAAGAGAATTATGCAGTGCTGCCATAACCATGAGTGATAACAC
TGCGGCCAACTTACTTCTGACAACTATCGGAGGACCGAAGGAGCTAACCG
CTTTTTTGCACAACATGGGGGATCATGTAACTCGCCTTGATCGTTGGGAA
CCGGAGCTGAATGAAGCCATACCAAACGACGAGCGTGACACCACGATGCC
TGTAGCAATGGCAACAACGTTGCGAAAACTATTAACTGGCGAACTACTTA
CTCTAGCTTCCCGGCAACAACTAATAGACTGGATGGAGGCGGATAAAGTT
GCAGGACCACTTCTGCGCTCGGCACTTCCGGCTGGCTGGTTTATTGCTGA
TAAATCAGGAGCCGGTGAGCGTGGGTCACGCGGTATCATTGCAGCACTGG
GGCCGGATGGTAAGCCCTCCCGTATCGTAGTTATCTACACTACGGGGAGT
CAGGCAACTATGGATGAACGAAATAGACAGATCGCTGAGATAGGTGCCTC
ACTGATTAAGCATTGGTAAGGATAAATTTCTGGTAAGGAGGACACGTATG
GAAGTGGGCAAGTTGGGGAAGCCGTATCCGTTGCTGAATCTGGCATATGT
GGGAGTATAAGACGCGCAGCGTCGCATCAGGCATTTTTTCTGCGCCAAT
GCAAAAAGGCCATCCGTCAGGATGGCCTTTCGCATAACTAGTGAGGCTCC
GGTGCCCGTCAGTGGGCAGAGCGCACATCGCCCACAGTCCCCGAGAAGTT
GGGGGGAGGGGTCGGCAATTGAACCGGTGCCTAGAGAAGGTGGCGCGGGG
TAAACTGGGAAAGTGATGTCGTGTACTGGCTCCGCCTTTTTCCCGAGGGT
GGGGGAGAACCGTATATAAGTGCAGTAGTCGCCGTGAACGTTCTTTTTCG
CAACGGGTTTGCCGCCAGAACACAGGTAAGTGCCGTGTGTGGTTCCCGCG
GGCCTGGCCTCTTTACGGGTTATGGCCCTTGCGTGCCTTGAATTACTTCC
```

CGCCCCTGGCTGCAGTACGTGATTCTTGATCCCGAGCTTCGGGTTGGAAG
TGGGTGGGAGAGTTCGAGGCCTTGCGCTTAAGGAGCCCCTTCGCCTCGTG
CTTGAGTTGAGGCCTGGCCTGGGCGCTGGGGCCGCCGCGTGCGAATCTGG
TGGCACCTTCGCGCCTGTCTCGCTGCTTTCGATAAGTCTCTAGCCATTTA
AAATTTTTGATGACCTGCTGCGACGCTTTTTTTCTGGCAAGATAGTCTTG
TAAATGCGGGCCAAGATCGATCTGCACACTGGTATTTCGGTTTTTGGGGC
CGCGGGCGGCGACGGGGCCCGTGCGTCCCAGCGCACATGTTCGGCGAGGC
GGGGCCTGCGAGCGCGGCCACCGAGAATCGGACGGGGGTAGTCTCAAGCT
GGCCGGCCTGCTCTGGTGCCTGGCCTCGCGCCGCCGTGTATCGCCCCGCC
CTGGGCGGCAAGGCTGGCCCGGTCGGCACCAGTTGCGTGAGCGGAAAGAT
GGCCGCTTCCCGGCCCTGCTGCAGGGAGCTCAAAATGGAGGACGCGGCGC
TCGGGAGAGCGGGCGGGTGAGTCACCCACACAAAGGAAAAGGGCCTTTCC
GTCCTCAGCCGTCGCTTCATGTGACTCCACGGAGTACCGGGCGCCGTCCA
GGCACCTCGATTAGTTCTCGAGCTTTTGGAGTACGTCGTCTTTAGGTTGG
GGGGAGGGGTTTTATGCGATGGAGTTTCCCCACACTGAGTGGGTGGAGAC
TGAAGTTAGGCCAGCTTGGCACTTGATGTAATTCTCCTTGGAATTTGCCC
TTTTTGAGTTTGGATCTTGGTTCATTCTCAAGCCTCAGACAGTGGTTCAA

HindIII
AGTTTTTTTCTTCCATTTCAGGTGTCGTGAAAAGCTT-------------

BamHI
------GGATCCATCTGGGATAAGCATGCTGTTTTCTGTCTGTCCCTAAC

ATGCCCTGTGATTATGCGCAAACAACACACCCAAGGGCAGAACTTTGTTA

CTTAAACACCATCCTGTTTGCTTCTTTCCTCAGGAACTGTGGCTGCACCA
                     T V A A P

TCTGTCTTCATCTTCCCGCCATCTGATGAGCAGTTGAAATCTGGAACTGC
S V F I F P P S D E Q L K S G T A

CTCTGTTGTGTGCCTGCTGAATAACTTCTATCCCAGAGAGGCCAAAGTAC
 S V V C L L N N F Y P R E A K V Q

AGTGGAAGGTGGATAACGCCCTCCAATCGGGTAACTCCCAGGAGAGTGTC
 W K V D N A L Q S G N S Q E S V

ACAGAGCAGGACAGCAAGGACAGCACCTACAGCCTCAGCAGCACCCTGAC
T E Q D S K D S T Y S L S S T L T

GCTGAGCAAAGCAGACTACGAGAAACACAAAGTCTACGCCTGCGAAGTCA
 L S K A D Y E K H K V Y A C E V T

CCCATCAGGGCCTGAGCTCGCCCGTCACAAAGAGCTTCAACA
GGGGAGAG
 H Q G L S S P V T K S F N R
G E

NotI      (Figure 2 cont'd)

TGTTGAGCGGCCGCAGGTAAGCCAGCCCAGGCCTCGCCCTCC
AGCTCAAGG
C   *

CGGGACAGGTGCCCTAGAGTAGCCTGCATCCAGGGACAGGCC
CCAGCCGGGTGCTGACACGTCCACCTCCATCTCTTCCTCAGG
TCTGCCCGGGTGGCATCCCTGTGACCCCTCCCCAGTGCCTCT
CCTGGCCCTGGAAGTTGCCACTCCAGTGCCCACCAGCCTTGT
CCTAATAAAATTAAGTTGCATCATTTTGTCTGACTAGGTGTC
CTTCTATAATATTATGGGGTGGAGGGGGGTGGTATGGAGCAA
GGGGCCCAAGTTAACTTGTTTATTGCAGCTTATAATGGTTAC
AAATAAAGCAATAGCATCACAAATTTCACAAATAAAGCATTT
TTTTCACTGCATTCTAGTTGTGGTTTGTCCAAACTCATCAAT
GTATCTTATCATGTCTGGATCTGCTTCAGGCACCGGGCTTGC
GGGTCATGCACCAGGTCGCGCGGTCCTTCGGGCACTCGACGT
CGGCGGTGACGGTGAAGCCGAGCCGCTCGTAGAAGGGGAGGT
TGCGGGGCGCGGAGGTCTCCAGGAAGGCGGGCACCCCGGCGC
GCTCGGCCGCCTCCACTCCGGGGAGCACGACGGCGCTGCCCA
GACCCTTGCCCTGGTGGTCGGGCGAGACGCCGACGGTGGCCA
GGAACCACGCGGGCTCCTTGGGCCGGTGCGGCGCCAGGAGGC
CTTCCATCTGTTGCTGCGCGGCAGCCGGGAACCGCTCAACT
CGGCCATGCGCGGGCCGATCTCGGCGAACACCGCCCCCGCTT
CGACGCTCTCCGGCGTGGTCCAGACCGCCACCGCGGCGCCGT
CGTCCGCGACCCACACCTTGCCGATGTCGAGCCCGACGCGCG
TGAGGAAGAGTTCTTGCAGCTCGGTGACCCGCTCGATGTGGC
GGTCCGGGTCGACGGTGTGGCGCGTGGCGGGGTAGTCGGCGA
ACGCGGCGGCGAGGGTGCGTACGGCCCGGGGACGTCGTCGC
GGGTGGCGAGGCGCACCGTGGGCTTGTACTCGGTCATGGTGG
CCTGCAGAGTCGCTCGGTGTTCGAGGCCACACGCGTCACCTT
AATATGCGAAGTGGACCTGGGACCGCGCCGCCCCGACTGCAT
CTGCGTGTTAATTCGCCAATGACAAGACGCTGGGCGGGGTTT
GTGTCATCATAGAACTAAAGACATGCAAATATATTTCTTCCG
GGGACACCGCCAGCAAACGCGAGCAACGGGCCACGGGGATGA
AGCAGCTGCGCCACTCCCTGAAGATCCATCGTCTCCTAACAA
GTTACATCACTCCTGCCCTTCCTCACCCTCATCTCCATCACC
TCCTTCATCTCCGTCATCTCCGTCATCACCCTCCGCGGCAGC
CCCTTCCACCATAGGTGGAAACCAGGGAGGCAAATCTACTCC
ATCGTCAAAGCTGCACACAGTCACCCTGATATTGCAGGTAGG
AGCGGGCTTTGTCATAACAAGGTCCTTAATCGCATCCTTCAA
AACCTCAGCAAATATATGAGTTTGTAAAAAGACCATGAAATA
ACAGACAATGGACTCCCTTAGCGGGCCAGGTTGTGGGCCGGG
TCCAGGGGCCATTCCAAAGGGGAGACGACTCAATGGTGTAAG
ACGACATTGTGGAATAGCAAGGGCAGTTCCTCGCCTTAGGTT
GTAAAGGGAGGTCTTACTACCTCCATATACGAACACACCGGC
GACCCAAGTTCCTTCGTCGGTAGTCCTTTCTACGTGACTCCT
AGCCAGGAGAGCTCTTAAACCTTCTGCAATGTTCTCAAATTT
CGGGTTGGAACCTCCTTGACCACGATGCTTTCCAAACCACCC
TCCTTTTTTGCGCCTGCCTCCATCACCCTGACCCCCGCTGCG
CGGGGGCACGTCAGGCTCACCATCTGGGCCGCCTTCTTGGTG
GTATTCAAAATAATCGGCTTCCCCTACAGGGTGGAAAAATGG
(Figure 2 cont'd)

```
CCTTCTACCTGGAGGGGGCCTGCGCGGTGGAGACCCGGATGA
TGATGACTGACTACTGGGACTCCTGGGCCTCTTTTCTCCACG
TCCACGACCTCTCCCCCTGGCTCTTTCACGACTTCCCCCCCT
GGCTCTTTCACGTCCTCTACCCCGGCGGCCTCCACTACCTCC
TCGACCCCGGCCTCCACTACCTCCTCGACCCCGGCCTCCACT
GCCTCCTCGACCCCGGCCTCCACCTCCTGCTCCTGCCCCTCC
CGCTCCTGCTCCTGCTCCTGTTCCACCGTGGGTCCCTTTGCA
GCCAATGCAACTTGGACGTTTTGGGGTCTCCGGACACCATC
TCTATGTCTTGGCCCTGATCCTGAGCCGCCCGGGGCTCCTGG
TCTTCCGCCTCCTCGTCCTCGTCCTCTTCCCCGTCCTCGTCC
ATGTGCCATGATGGCGGCCTGCAGCTGTGTTCGAGGCCGCGC
GTGTCACCTTAATATGCGAAGTGGACCTGGGACCGCGCCGCC
CCGACTGCATCTGCGTGTTCGAGTTCGCCAATGACAAGACGC
TGGGCGGGGAGATCCCCCTTATTAACCCTAAACGGGTAGCAT
ATGCTTCCCGGGTAGTAGTATATACTATCCAGACTAACCCTA
ATTCAATAGCATATGTTACCCAACGGGAAGCATATGCTATCG
AATTAGGGTTAGTAAAAGGGTCCTAAGGAACAGCGATCTGGA
TAGCATATGCTATCCTAATCTATATCTGGGTAGCATATGCTA
TCCTAATCTATATCTGGGTAGCATAGGCTATCCTAATCTATA
TCTGGGTAGCATATGCTATCCTAATCTATATCTGGGTAGTAT
ATGCTATCCTAATTTATATCTGGGTAGCATAGGCTATCCTAA
TCTATATCTGGGTAGCATATGCTATCCTAATCTATATCTGGG
TAGTATATGCTATCCTAATCTGTATCCGGGTAGCATATGCTA
TCCTCATGCATATACAGTCAGCATATGATACCCAGTAGTAGA
GTGGGAGTGCTATCCTTTGCATATGCCGCCACCTCCCAAGGA
GATCTGTCGACATCGATGGGCGCGGGTGTACACTCCGCCCAT
CCCGCCCCTAACTCCGCCCAGTTCCGCCCATTCTCCGCCTCA
TGGCTGACTAATTTTTTTATTTATGCAGAGGCCGAGGCCGC
CTCGGCCTCTGAGCTATTCCAGAAGTAGTGAGGAGGCTTTTT
TGGAGGCCTAGGCTTTTGCAAAAAGCTAATTC
```

*The destroyed internal vector BamHI site is high-lighted in bold and underlined pEAK8 Human Heavy Chain Vector

```
GGCGTAATCTGCTGCTTGCAAACAAAAAAACCACCGCTACCAGCGGTGGT
TTGTTTGCCGGATCAAGAGCTACCAACTCTTTTTCCGAAGGTAACTGGCT
TCAGCAGAGCGCAGATACCAAATACTGTCCTTCTAGTGTAGCCGTAGTTA
GGCCACCACTTCAAGAACTCTGTAGCACCGCCTACATACCTCGCTCTGCT
AATCCTGTTACCAGTGGCTGCTGCCAGTGGCGATAAGTCGTGTCTTACCG
GGTTGGACTCAAGACGATAGTTACCGGATAAGGCGCAGCGGTCGGGCTGA
ACGGGGGGTTCGTGCACACAGCCCAGCTTGGAGCGAACGACCTACACCGA
ACTGAGATACCTACAGCGTGAGCATTGAGAAAGCGCCACGCTTCCCGAAG
GGAGAAAGGCGGACAGGTATCCGGTAAGCGGCAGGGTCGGAACAGGAGAG
CGCACGAGGGAGCTTCCAGGGGGAAACGCCTGGTATCTTTATAGTCCTGT
CGGGTTTCGCCACCTCTGACTTGAGCGTCGATTTTTGTGATGCTCGTCAG
GGGGGCGGAGCCTATGGAAAAACGCCAGCAACGCAAGCTAGAGTTTAAAC
TTGACAGATGAGACAATAACCCTGATAAATGCTTCAATAATATTGAAAAA
GGAAAAGTATGAGTATTCAACATTTCCGTGTCGCCCTTATTCCCTTTTTT
GCGGCATTTTGCCTTCCTGTTTTTGCTCACCCAGAAACGCTGGTGAAAGT
AAAAGATGCAGAAGATCACTTGGGTGCGCGAGTGGGTTACATCGAACTGG
ATCTCAACAGCGGTAAGATCCTTGAGAGTTTTCGCCCCGAAGAACGTTTC
CCAATGATGAGCACTTTTAAAGTTCTGCTATGTGGCGCGGTATTATCCCG
TATTCTTGGTTGAATACTCACCAGTCACAGAAAAGCATCTTACGGATGGC
ATGACAGTAAGAGAATTATGCAGTGCTGCCATAACCATGAGTGATAACAC
TGCGGCCAACTTACTTCTGACAACTATCGGAGGACCGAAGGAGCTAACCG
CTTTTTTGCACAACATGGGGGATCATGTAACTCGCCTTGATCGTTGGGAA
CCGGAGCTGAATGAAGCCATACCAAACGACGAGCGTGACACCACGATGCC
TGTAGCAATGGCAACAACGTTGCGAAACTATTAACTGGCGAACTACTTA
CTCTAGCTTCCCGGCAACAACTAATAGACTGGATGGAGGCGGATAAAGTT
GCAGGACCACTTCTGCGCTCGGCACTTCCGGCTGGCTGGTTTATTGCTGA
TAAATCAGGAGCCGGTGAGCGTGGGTCACGCGGTATCATTGCAGCACTGG
GGCCGGATGGTAAGCCCTCCCGTATCGTAGTTATCTACACTACGGGGAGT
CAGGCAACTATGGATGAACGAAATAGACAGATCGCTGAGATAGGTGCCTC
ACTGATTAAGCATTGGTAAGGATAAATTTCTGGTAAGGAGGACACGTATG
GAAGTGGGCAAGTTGGGGAAGCCGTATCCGTTGCTGAATCTGGCATATGT
GGGAGTATAAGACGCGCAGCGTCGCATCAGGCATTTTTTCTGCGCCAAT
GCAAAAAGGCCATCCGTCAGGATGGCCTTTCGCATAACTAGTGAGGCTCC
GGTGCCCGTCAGTGGGCAGAGCGCACATCGCCCACAGTCCCCGAGAAGTT
GGGGGGAGGGGTCGGCAATTGAACCGGTGCCTAGAGAAGGTGGCGCGGGG
TAAACTGGGAAAGTGATGTCGTGTACTGGCTCCGCCTTTTTCCCGAGGGT
GGGGGAGAACCGTATATAAGTGCAGTAGTCGCCGTGAACGTTCTTTTTCG
```

```
CAACGGGTTTGCCGCCAGAACACAGGTAAGTGCCGTGTGTGGTTCCCGCG
GGCCTGGCCTCTTTACGGGTTATGGCCCTTGCGTGCCTTGAATTACTTCC
CGCCCCTGGCTGCAGTACGTGATTCTTGATCCCGAGCTTCGGGTTGGAAG
TGGGTGGGAGAGTTCGAGGCCTTGCGCTTAAGGAGCCCCTTCGCCTCGTG
CTTGAGTTGAGGCCTGGCCTGGGCGCTGGGGCCGCCGCGTGCGAATCTGG
TGGCACCTTCGCGCCTGTCTCGCTGCTTTCGATAAGTCTCTAGCCATTTA
AAATTTTTGATGACCTGCTGCGACGCTTTTTTTCTGGCAAGATAGTCTTG
TAAATGCGGGCCAAGATCGATCTGCACACTGGTATTTCGGTTTTTGGGGC
CGCGGGCGGCGACGGGGCCCGTGCGTCCCAGCGCACATGTTCGGCGAGGC
GGGGCCTGCGAGCGCGGCCACCGAGAATCGGACGGGGGTAGTCTCAAGCT
GGCCGGCCTGCTCTGGTGCCTGGCCTCGCGCCGCCGTGTATCGCCCCGCC
CTGGGCGGCAAGGCTGGCCCGGTCGGCACCAGTTGCGTGAGCGGAAAGAT
GGCCGCTTCCCGGCCCTGCTGCAGGGAGCTCAAAATGGAGGACGCGGCGC
TCGGGAGAGCGGGCGGGTGAGTCACCCACACAAAGGAAAAGGGCCTTTCC
GTCCTCAGCCGTCGCTTCATGTGACTCCACGGAGTACCGGGCGCCGTCCA
GGCACCTCGATTAGTTCTCGAGCTTTTGGAGTACGTCGTCTTTAGGTTGG
GGGGAGGGGTTTTATGCGATGGAGTTTCCCCACACTGAGTGGGTGGAGAC
TGAAGTTAGGCCAGCTTGGCACTTGATGTAATTCTCCTTGGAATTTGCCC
TTTTTGAGTTTGGATCTTGGTTCATTCTCAAGCCTCAGACAGTGGTTCAA
```

HindIII

`AGTTTTTTTCTTCCATTTCAGGTGTCGTGAA``AAGCTT``-------------`

BamHI

`--------------------``GGATCC``TCTGCGCCTGGGCCCAGCTCTGTC`

```
CCACACCGCGGTCACATGGCACCACCTCTCTTGCAGCCTCCACCAAGGGC
                                    S   T   K   G
CCATCGGTCTTCCCCCTGGCACCCTCCTCCAAGAGCACCTCTGGGGGCAC
 P   S   V   F   P   L   A   P   S   S   K   S   T   S   G   G   T

AGCGGCCCTGGGCTGCCTGGTCAAGGACTACTTCCCCGAACCGGTGACGG
  A   A   L   G   C   L   V   K   D   Y   F   P   E   P   V   T   V

TGTCGTGGAACTCAGGCGCCCTGACCAGCGGCGTGCACACCTTCCCGGCT
  S   W   N   S   G   A   L   T   S   G   V   H   T   F   P   A

GTCCTACAGTCCTCAGGACTCTACTCCCTCAGCAGCGTGGTGACCGTGCC
 V   L   Q   S   S   G   L   Y   S   L   S   S   V   Y   S   V   P

CTCCAGCAGCTTGGGCACCCAGACCTACATCTGCAACGTGAATCACAAGC
  S   S   S   L   G   T   Q   T   Y   I   C   N   V   N   H   K   P

CCAGCAACACCAAGGTGGACAAGAAAGTTGAGCCCAAATCTTGTGACAAA
  S   N   T   K   V   D   K   K   V   E   P   K   S   C   D   K

ACTCACACATGCCCACCGTGCCCAGCACCTGAACTCCTGGGGGGACCGTC
  T   H   T   C   P   P   C   P   A   P   E   L   L   G   G   P   S
```

(Figure 3 cont'd)

```
AGTCTTCCTCTTCCCCCCAAAACCCAAGGACACCCTCATGATCTCCCGGA
 V  F  L  F  P  P  K  P  K  D  T  L  M  I  S  R  T

CCCCTGAGGTCACATGCGTGGTGGTGGACGTGAGCCACGAAGACCCTGAG
  P  E  V  T  C  V  V  V  D  V  S  H  E  D  P  E

GTCAAGTTCAACTGGTACGTGGACGGCGTGGAGGTGCATAACGCCAAGAC
 V  K  F  N  W  Y  V  D  G  V  E  V  H  N  A  K  T

AAAGCCGCGGGAGGAGCAGTACAACAGCACGTACCGGGTGGTCAGCGTCC
 K  P  R  E  E  Q  Y  N  S  T  Y  R  V  V  S  V  L

TCACCGTCCTGCACCAGGACTGGCTGAATGGCAAGGAGTACAAGTGCAAG
  T  V  L  H  Q  D  W  L  N  G  K  E  Y  K  C  K

GTCTCCAACAAAGCCCTCCCAGCCCCCATCGAGAAAACCATCTCCAAAGC
 V  S  N  K  A  L  P  A  P  I  E  K  T  I  S  K  A

CAAAGGGCAGCCCCGAGAACCACAGGTGTACACCCTGCCCCCATCCCGGG
 K  G  Q  P  R  E  P  Q  V  Y  T  L  P  P  S  R  E

AGGAGATGACCAAGAACCAGGTCAGCCTGACCTGCCTGGTCAAAGGCTTC
  E  M  T  K  N  Q  V  S  L  T  C  L  V  K  G  F

TATCCCAGCGACATCGCCGTGGAGTGGGAGAGCAATGGGCAGCCGGAGAA
 Y  P  S  D  I  A  V  E  W  E  S  N  G  Q  P  E  N

CAACTACAAGACCACGCCTCCCGTGCTGGACTCCGACGGCTCCTTCTTCC
  N  Y  K  T  T  P  P  V  L  D  S  D  G  S  F  F  L

TCTACAGCAAGCTCACCGTGGACAAGAGCAGGTGGCAGCAGGGGAACGTC
  Y  S  K  L  T  V  D  K  S  R  W  Q  Q  G  N  V

TTCTCATGCTCCGTGATGCATGAGGCTCTGCACAACCACTACACGCAGAA
 F  S  C  S  V  M  H  E  A  L  H  N  H  Y  T  Q  K

NotI
GAGCCTCTCCCTGTCTCCGGGTAAATGAGCGGCCGCAGGTAA
GCCAGCCCA
  S  L  S  L  S  P  G  K  *

GGCCTCGCCCTCCAGCTCAAGGCGGGACAGGTGCCCTAGAGT
AGCCTGCATCCAGGGACAGGCCCCAGCCGGGTGCTGACACGT
CCACCTCCATCTCTTCCTCAGGTCTGCCCGGGTGGCATCCCT
GTGACCCCTCCCCAGTGCCTCTCCTGGCCCTGGAAGTTGCCA
CTCCAGTGCCCACCAGCCTTGTCCTAATAAAATTAAGTTGCA
TCATTTTGTCTGACTAGGTGTCCTTCTATAATATTATGGGGT
GGAGGGGGGTGGTATGGAGCAAGGGGCCCAAGTTAACTTGTT
TATTGCAGCTTATAATGGTTACAAATAAAGCAATAGCATCAC
AAATTTCACAAATAAAGCATTTTTTTCACTGCATTCTAGTTG
(Figure 3 cont'd)
```

```
TGGTTTGTCCAAACTCATCAATGTATCTTATCATGTCTGGAT
CTGCTTCAGGCACCGGGCTTGCGGGTCATGCACCAGGTCGCG
CGGTCCTTCGGGCACTCGACGTCGGCGGTGACGGTGAAGCCG
AGCCGCTCGTAGAAGGGGAGGTTGCGGGGCGCGGAGGTCTCC
AGGAAGGCGGGCACCCCGGCGCGCTCGGCCGCCTCCACTCCG
GGGAGCACGACGGCGCTGCCCAGACCCTTGCCCTGGTGGTCG
GGCGAGACGCCGACGGTGGCCAGGAACCACGCGGGCTCCTTG
GGCCGGTGCGGCGCCAGGAGGCCTTCCATCTGTTGCTGCGCG
GCCAGCCGGGAACCGCTCAACTCGGCCATGCGCGGGCCGATC
TCGGCGAACACCGCCCCCGCTTCGACGCTCTCCGGCGTGGTC
CAGACCGCCACCGCGGCGCCGTCGTCCGCGACCCACACCTTG
CCGATGTCGAGCCCGACGCGCGTGAGGAAGAGTTCTTGCAGC
TCGGTGACCCGCTCGATGTGGCGGTCCGGGTCGACGGTGTGG
CGCGTGGCGGGGTAGTCGGCGAACGCGGCGGCGAGGGTGCGT
ACGCCCGGGGACGTCGTCGCGGGTGGCGAGGCGCACCGTG
GGCTTGTACTCGGTCATGGTGGCCTGCAGAGTCGCTCGGTGT
TCGAGGCCACACGCGTCACCTTAATATGCGAAGTGGACCTGG
GACCGCGCCGCCCCGACTGCATCTGCGTGTTAATTCGCCAAT
GACAAGACGCTGGGCGGGGTTTGTGTCATCATAGAACTAAAG
ACATGCAAATATATTTCTTCCGGGGACACCGCCAGCAAACGC
GAGCAACGGGCCACGGGATGAAGCAGCTGCGCCACTCCCTG
AAGATCCATCGTCTCCTAACAAGTTACATCACTCCTGCCCTT
CCTCACCCTCATCTCCATCACCTCCTTCATCTCCGTCATCTC
CGTCATCACCCTCCGCGGCAGCCCCTTCCACCATAGGTGGAA
ACCAGGGAGGCAAATCTACTCCATCGTCAAAGCTGCACACAG
TCACCCTGATATTGCAGGTAGGAGCGGGCTTTGTCATAACAA
GGTCCTTAATCGCATCCTTCAAAACCTCAGCAAATATATGAG
TTTGTAAAAGACCATGAAATAACAGACAATGGACTCCCTTA
GCGGGCCAGGTTGTGGGCCGGGTCCAGGGGCCATTCCAAAGG
GGAGACGACTCAATGGTGTAAGACGACATTGTGGAATAGCAA
GGGCAGTTCCTCGCCTTAGGTTGTAAAGGGAGGTCTTACTAC
CTCCATATACGAACACACCGGCGACCCAAGTTCCTTCGTCGG
TAGTCCTTTCTACGTGACTCCTAGCCAGGAGAGCTCTTAAAC
CTTCTGCAATGTTCTCAAATTTCGGGTTGGAACCTCCTTGAC
CACGATGCTTTCCAAACCACCCTCCTTTTTTGCGCCTGCCTC
CATCACCCTGACCCCCGCTGCGCGGGGGCACGTCAGGCTCAC
CATCTGGGCCGCCTTCTTGGTGGTATTCAAAATAATCGGCTT
CCCCTACAGGGTGGAAAAATGGCCTTCTACCTGGAGGGGGCC
TGCGCGGTGGAGACCCGGATGATGATGACTGACTACTGGGAC
TCCTGGGCCTCTTTTCTCCACGTCCACGACCTCTCCCCCTGG
CTCTTTCACGACTTCCCCCCCTGGCTCTTTCACGTCCTCTAC
CCCGGCGGCCTCCACTACCTCCTCGACCCCGGCCTCCACTAC
CTCCTCGACCCCGGCCTCCACTGCCTCCTCGACCCCGGCCTC
CACCTCCTGCTCCTGCCCCTCCCGCTCCTGCTCCTGCTCCTG
TTCCACCGTGGGTCCCTTTGCAGCCAATGCAACTTGGACGTT
TTTGGGGTCTCCGGACACCATCTCTATGTCTTGGCCCTGATC
CTGAGCCGCCCGGGGCTCCTGGTCTTCCGCCTCCTCGTCCTC
GTCCTCTTCCCCGTCCTCGTCCATGTGCCATGATGGCGGCCT
GCAGCTGTGTTCGAGGCCGCGCGTGTCACCTTAATATGCGAA
GTGGACCTGGGACCGCGCCGCCCCGACTGCATCTGCGTGTTC
```
(Figure 3 cont'd)

```
GAGTTCGCCAATGACAAGACGCTGGGCGGGGAGATCCCCCTT
ATTAACCCTAAACGGGTAGCATATGCTTCCCGGGTAGTAGTA
TATACTATCCAGACTAACCCTAATTCAATAGCATATGTTACC
CAACGGGAAGCATATGCTATCGAATTAGGGTTAGTAAAAGGG
TCCTAAGGAACAGCGATCTGGATAGCATATGCTATCCTAATC
TATATCTGGGTAGCATATGCTATCCTAATCTATATCTGGGTA
GCATAGGCTATCCTAATCTATATCTGGGTAGCATATGCTATC
CTAATCTATATCTGGGTAGTATATGCTATCCTAATTTATATC
TGGGTAGCATAGGCTATCCTAATCTATATCTGGGTAGCATAT
GCTATCCTAATCTATATCTGGGTAGTATATGCTATCCTAATC
TGTATCCGGGTAGCATATGCTATCCTCATGCATATACAGTCA
GCATATGATACCCAGTAGTAGAGTGGGAGTGCTATCCTTTGC
ATATGCCGCCACCTCCCAAGGAGATCTGTCGACATCGATGGG
CGCGGGTGTACACTCCGCCCATCCCGCCCCTAACTCCGCCCA
GTTCCGCCCATTCTCCGCCTCATGGCTGACTAATTTTTTTTA
TTTATGCAGAGGCCGAGGCCGCCTCGGCCTCTGAGCTATTCC
AGAAGTAGTGAGGAGGCTTTTTGGAGGCCTAGGCTTTTGCA
AAAAGCTAATTC
```

(Figure 3 cont'd)

CHIMERIC ANTI-VEGF-D ANTIBODIES AND HUMANIZED ANTI-VEGF-D ANTIBODIES AND METHODS OF USING SAME

The present application is a continuation of U.S. patent application Ser. No. 11/074,373, filed Mar. 7, 2005, now abandoned, which claims the priority benefit of U.S. Provisional Application No. 60/550,441, filed Mar. 5, 2004, incorporated herein by reference in its entirety.

FIELD OF THE INVENTION

The present invention provides materials and methods relating to modulators of vascular endothelial growth factors with respect to vascularization and angiogenesis. The invention also provides therapeutic compositions for the modulation of lymphangiogenesis, and methods for ameliorating tumor growth and metastasis in patients with cancer.

BACKGROUND OF THE INVENTION

Angiogenesis is a fundamental process required for normal growth and development of tissues, and involves the proliferation of new capillaries from pre-existing blood vessels. Angiogenesis is not only involved in embryonic development and normal tissue growth, repair, and regeneration, but is also involved in the female reproductive cycle, establishment and maintenance of pregnancy, and in repair of wounds and fractures. In addition to angiogenesis which takes place in the healthy individual, angiogenic events are involved in a number of pathological processes, notably tumor growth and metastasis, and other conditions in which blood vessel proliferation, especially of the microvascular system, is increased, such as diabetic retinopathy, psoriasis and arthropathies. Inhibition of angiogenesis is useful in preventing or alleviating these pathological processes.

Because of the crucial role of angiogenesis in so many physiological and pathological processes, factors involved in the control of angiogenesis have been intensively investigated. A number of growth factors have been shown to be involved in the regulation of angiogenesis; these include fibroblast growth factors (FGFs), platelet-derived growth factor (PDGF), transforming growth factor-α (TGFα), and hepatocyte growth factor (HGF). See for example Folkman et al, "Angiogenesis", *J. Biol. Chem.*, 267:10931-10934, 1992, for a review.

It has been suggested that a particular family of endothelial cell-specific growth factors and their corresponding receptors is primarily responsible for stimulation of endothelial cell growth and differentiation, and for certain functions of the differentiated cells. These factors are members of the PDGF/VEGF family, which act via receptor tyrosine kinases (RTKs).

Numerous PDGF/VEGF family members have been identified. These include PDGF-A (see e.g., GenBank Acc. No. X06374), PDGF-B (see e.g., GenBank Acc. No. M12783), PDGF-C (Intl. Publ. No. WO 00/18212), PDGF-D (Intl. Publ. No. WO 00/027879), VEGF (also known as VEGF-A or by particular isoform), Placenta growth factor, PlGF (U.S. Pat. No. 5,919,899), VEGF-B (also known as VEGF-related factor (VRF) Intl. Publ. No. PCT/US96/02597 and WO 96/26736; U.S. Pat. Nos. 6,331,301; 5,840,693; 5,928,939; 5,607,918), VEGF-C, (U.S. Pat. Nos. 6,645,933; 6,403,088; 6,361,946; 6,221,839; 6,130,071 and International Patent Publication No. WO 98/33917), VEGF-D (also known as c-fos-induced growth factor (FIGF) (U.S. Pat. Nos. 6,383,484 and 6,235,713, Intl. Publ. No. WO98/07832), VEGF-E (also known as NZ7 VEGF or OV NZ7; Intl. Publ. No. WO00/025805 and U.S. Patent Publ. No. 2003/0113870), NZ2 VEGF (also known as OV NZ2; see e.g., GenBank Acc. No. S67520), D1701 VEGF-like protein (see e.g., GenBank Acc. No. AF106020; Meyer et al., *EMBO J.* 18:363-374), and NZ10 VEGF-like protein (described in Intl. Patent Application PCT/US99/25869) [Stacker and Achen, *Growth Factors* 17:1-11 (1999); Neufeld et al., *FASEB J* 13:9-22 (1999); Ferrara, *J Mol Med* 77:527-543 (1999)].

The PDGF/VEGF family proteins are predominantly secreted glycoproteins that form either disulfide-linked or non-covalently bound homo- or heterodimers whose subunits are arranged in an anti-parallel manner [Stacker and Achen, *Growth Factors* 17:1-11 (1999); Muller et al., *Structure* 5:1325-1338 (1997)]. Each VEGF family member has between 30% and 45% amino acid sequence identity with VEGF. The VEGF family members share a VEGF homology domain which contains the six cysteine residues which form the cysteine knot motif. Functional characteristics of the VEGF family include varying degrees of mitogenicity for endothelial cells, induction of vascular permeability and angiogenic and lymphangiogenic properties.

Vascular endothelial growth factors appear to act by binding to receptor tyrosine kinases of the PDGF/VEGF-receptor family. Six endothelial cell receptor tyrosine kinases which bind PDGF/VEGF molecules have been identified, namely Flt-1 (VEGFR-1), KDR/Flk-1 (VEGFR-2), Flt4 (VEGFR-3), Tie and Tek/Tie-2, and the PDGF receptor. All of these have the intrinsic tyrosine kinase activity which is necessary for signal transduction. The essential, specific role in vasculogenesis and angiogenesis of Flt-1, Flk-1, Tie and Tek/Tie-2 has been demonstrated by targeted mutations inactivating these receptors in mouse embryos.

VEGFR-1 and VEGFR-2 bind VEGF with high affinity, and VEGFR-1 also binds VEGF-B and placenta growth factor (PlGF). VEGF-C has been shown to be a ligand for Flt4 (VEGFR-3), and also activates VEGFR-2 (Joukov et al., *EMBO J.*, 15: 290-298, 1996). VEGF-D binds to both VEGFR-2 and VEGFR-3. A ligand for Tek/Tie-2 has been described (International Patent Application No. PCT/US95/12935 (WO 96/11269) by Regeneron Pharmaceuticals, Inc.); however, the ligand for Tie has not yet been identified.

VEGFR-1, VEGFR-2 and VEGFR-3 are expressed differently by endothelial cells. Both VEGFR-1 and VEGFR-2 are expressed in blood vessel endothelia (Oelrichs et al., *Oncogene*, 8: 11-18, 1992; Kaipainen et al., *J. Exp. Med.*, 178: 2077-2088, 1993; Dumont et al., *Dev. Dyn.*, 203:80-92, 1995; Fong et al., *Dev. Dyn.*, 207:1-10, 1996) and VEGFR-3 is mostly expressed in the lymphatic endothelium of adult tissues (Kaipainen et al., *Proc. Natl. Acad. Sci. USA*, 9: 3566-3570, 1995). VEGFR-3 is also expressed in the blood vasculature surrounding tumors.

Disruption of the VEGFR genes results in aberrant development of the vasculature leading to embryonic lethality around midgestation. Analysis of embryos carrying a completely inactivated VEGFR-1 gene suggests that this receptor is required for functional organization of the endothelium (Fong et al., *Nature*, 376: 66-70, 1995). However, deletion of the intracellular tyrosine kinase domain of VEGFR-1 generates viable mice with a normal vasculature (Hiratsuka et al., *Proc. Natl. Acad. Sci. USA*, 95:9349-9354, 1998). The reasons underlying these differences remain to be explained but suggest that receptor signaling via the tyrosine kinase is not required for the proper function of VEGFR-1. Analysis of homozygous mice with inactivated alleles of VEGFR-2 suggests that this receptor is required for endothelial cell proliferation, hematopoesis and vasculogenesis (Shalaby et al., Nature, 376: 62-66, 1995; Shalaby et al., Cell, 89: 981-990, 1997). Inactivation of VEGFR-3 results in cardiovascular failure due to abnormal organization of the large vessels (Dumont et al., Science 282:946-949, 1998).

VEGFR-3 is widely expressed on endothelial cells during early embryonic development but as embryogenesis proceeds becomes restricted to venous endothelium and then to the lymphatic endothelium (Kaipainen et al., Cancer Res., 54:6571-6577, 1994; Kaipainen et al., Proc. Natl. Acad. Sci. USA, 92:3566-3570, 1995). VEGFR-3 is expressed on lymphatic endothelial cells in adult tissues. This receptor is essential for vascular development during embryogenesis. Abnormal development or function of the lymphatic endothelial cells can result in tumors or malformations of the lymphatic vessels, such as lymphangiomas or lymphangiectasis. Witte, et al., Regulation of Angiogenesis (eds. Goldber, I. D. & Rosen, E. M.) 65-112 (Birkä user, Basel, Switzerland, 1997). The VEGFR-3 receptor is upregulated in many types of vascular tumors, including Kaposi's sarcomas (Jussila et al., Cancer Res 58, 1955-1604, 1998; Partanen et al., Cancer 86:2406-2412, 1999). The importance of VEGFR-3 signaling for lymphangiogenesis was revealed in the genetics of familial lymphedema, a disease characterized by a hypoplasia of cutaneous lymphatic vessels, which leads to a disfiguring and disabling swelling of the extremities (Witte, et al., Regulation of Angiogenesis (supra); Rockson, S. G., Am. J. Med. 110, 288-295, 2001). Additional studies demonstrated that signaling through the VEGFR-3 receptor is sufficient to induce lymphangiogenesis (Viekkola et al., EMBO J. 20:1223-31, 2001). Further, the ligands for VEGFR-3, VEGF-C and VEGF-D, are also involved in pathogenic angiogenesis in some tumors.

Recent evidence on the association of lymphangiogenic growth factors with intralymphatic growth and metastasis of cancers (PCT/US99/23525; WO 02/060950; Mandriota, et al., EMBO J. 20:672-682, 2001); Skobe et al., Nat. Med. 7:192-198, 2001); Stacker et al., Nat. Med. 7:186-191, 2001); Karpanen et al., Cancer Res. 61:1786-1790, 2001) has provided an indication for anti-lymphangiogenic agents for tumor therapy. VEGF-C and VEGF-D signaling through the VEGFR-3 receptor has been shown to be the primary source of lymphangiogenic activation and has also been noted in pathogenic angiogenesis in some tumors.

Cancer cells spread within the body by direct invasion to surrounding tissues, spreading to body cavities, invasion into the blood vascular system (hematogenous metastasis), as well as spread via the lymphatic system (lymphatic metastasis). Regional lymph node dissemination is the first step in the metastasis of several common cancers and correlates highly with the prognosis of the disease. The lymph nodes that are involved in draining tissue fluid from the tumor area are called sentinel nodes, and diagnostic measures are in place to find these nodes and to remove them in cases of suspected metastasis. However, in spite of its clinical relevance, little is known about the mechanisms leading to metastasis via the bloodstream or via the lymphatics.

Thus, there remains a need in the art to find modulators of the growth factors and receptors involved in angiogenesis and lymphangiogenesis. Additionally, there continues to be a need for new modulators that act as specific regulators of tumor cells to improve therapy over current, non-specific cancer therapeutics, and preferably provide low, therapeutic doses and reduced toxicity and side effects to the patient.

SUMMARY OF THE INVENTION

The present invention addresses one or more needs in the art relating to regulation of angiogenesis and lymphangiogenesis by providing humanized or chimeric VEGF-D antibody substance materials and methods for inhibiting angiogenesis and lymphangiogenesis or other biological activities mediated by VEGF-D through its receptors. The antibody materials are formulated into compositions of the invention useful as therapeutics that modulate growth factor receptor-ligand interactions in subjects experiencing aberrant angiogenesis or lymphangiogenesis or other conditions characterized by VEGF-D overexpression, and may be administered with a second agent.

The invention provides a humanized antibody substance comprising an antibody that specifically binds Vascular Endothelial Growth Factor-D (VEGF-D), comprising i) a light chain variable region comprising a polypeptide comprising the amino acid sequence of SEQ ID NO: 37; ii) a heavy chain variable region comprising a polypeptide comprising the amino acid sequence of SEQ ID NO: 39; iii) a human antibody light chain constant region; and iv) a human antibody heavy chain constant region; or a fragment thereof that binds VEGF-D. In one aspect, the antibody that specifically binds Vascular Endothelial Growth Factor-D (VEGF-D), comprises i) complementarity determining regions (CDR) from a mouse antibody and framework regions (FR) from a non-murine source, wherein the heavy chain variable region ($V_H$) comprises complementarity determining regions (CDR) with the amino acid sequences: H-CDR1 set out in SEQ ID NO: 50; H-CDR2 set out in SEQ ID NO: 51; H-CDR3 set out in SEQ ID NO: 52; ii) complementarity determining regions from a mouse antibody and framework regions from non-murine source, wherein the light chain variable region ($V_L$) comprises complementarity determining regions (CDR) with the amino acid sequences: L-CDR1 set out in SEQ ID NO: 47; L-CDR2 set out in SEQ ID NO: 48; L-CDR3 set out in SEQ ID NO: 49; iii) a human antibody light chain constant region; and iv) a human antibody heavy chain constant region; or a fragment thereof that binds VEGF-D.

In one embodiment, the framework regions which are non-murine sequences are derived from a human antibody having sequence similarity to the mouse framework region. In another embodiment, the framework regions are chemically synthesized to comprise substitute amino acids more commonly seen in human framework regions, but not identical to a human antibody framework region. This substitution is carried out using techniques common in the art, and any of the four framework regions in the antibody variable chain may contain one, two, three, four, or five substituted amino acids.

In a related embodiment, the residues of the heavy chain framework region which can be altered lie within regions designated H-FR1, H-FR2, H-FR3 and H-FR4, which surround the heavy chain CDR residues, and the residues of the light chain framework regions which can be altered lie within the regions designated L-FR1, L-FR2, L-FR3 and L-FR4, which surround the light chain CDR residues.

In one aspect, the invention provides an humanized antibody substance described above wherein the light chain constant region is a kappa or lambda light chain. In a related aspect, the invention provides an humanized antibody substance wherein the heavy chain constant region is selected from the group consisting of a constant region from an IgM chain, an IgG chain, an IgA chain, an IgE chain, an IgD chain, fragments thereof, and combinations thereof. In one embodiment, the heavy chain constant region comprises an IgG chain selected from the group consisting of IgG1, IgG2, IgG3, IgG4, fragments thereof, and combinations thereof. In a further embodiment, the constant region comprises at least one of CH1, CH2, and CH3 regions of a human IgG1 heavy chain constant region.

In another aspect, the humanized antibody substance comprises a Fab fragment of the humanized antibody. In one embodiment, the humanized antibody substance is a monoclonal antibody.

The invention contemplates a chimeric monoclonal antibody which specifically binds to Vascular Endothelial Growth Factor-D (VEGF-D), the monoclonal antibody comprising complementarity determining regions (CDR) of non-human origin from SEQ ID NOS: 37 and 39 and constant regions of light and heavy chains, said constant region being of human origin, wherein the biological function of specific binding to said VEGF-D is preserved.

In one aspect, the invention provides a humanized antibody having binding specificity for Vascular Endothelial Growth Factor-D (VEGF-D), said humanized antibody comprising a light chain variable region comprising the amino acid sequence of SEQ ID NO: 37. In a related aspect, the humanized antibody further comprises a heavy chain variable region from an antibody having binding specificity for VEGF-D. In a further aspect, the invention contemplates a humanized antibody having binding specificity for Vascular Endothelial Growth Factor-D (VEGF-D), said humanized antibody comprising a heavy chain variable region comprising the amino acid sequence of SEQ ID NO: 39. In another aspect, the humanized antibody further comprises a light chain variable region from an antibody having binding specificity for VEGF-D.

The invention further provides a purified polypeptide comprising an antigen binding region of a VEGF-D antibody, wherein the antigen binding region comprises an amino acid sequence at least 90% identical to the amino acid sequence of SEQ ID NO: 37. In one embodiment, the polypeptide may be 90%, 95%, 96%, 97%, 98%, or 99% identical to the polypeptide of SEQ ID NO: 37. The invention also contemplates a purified polypeptide comprising an antigen binding region of a VEGF-D antibody, wherein the antigen binding region comprises an amino acid sequence at least 90% identical to the amino acid sequence of SEQ ID NO: 39. In one embodiment, the polypeptide may be 90%, 95%, 96%, 97%, 98%, or 99% identical to the polypeptide of SEQ ID NO: 39. It is further contemplated that the invention provides a purified polypeptide comprising the amino acid sequence of SEQ ID NO: 37 fused to the amino acid sequence of SEQ ID NO: 39, or fragments thereof that include at least a portion of SEQ ID NO: 37 and SEQ ID NO: 39, wherein the polypeptide binds VEGF-D.

In one aspect, the invention comprises a purified polypeptide comprising (a) complementarity determining regions from a mouse antibody and framework regions from a non-murine source, wherein the heavy chain variable region ($V_H$) comprises complementarity determining regions (CDR) with the amino acid sequences: H-CDR1 set out in SEQ ID NO: 50; H-CDR2 set out in SEQ ID NO: 51; H-CDR3 set out in SEQ ID NO: 52: (b) complementarity determining regions from a mouse antibody and framework regions from a non-murine source, wherein the light chain variable region ($V_L$) comprises complementarity determining regions (CDR) with the amino acid sequences: L-CDR1 set out in SEQ ID NO: 47; L-CDR2 set out in SEQ ID NO: 48; L-CDR3 set out in SEQ ID NO: 49; and (c) fragments of (a) or (b) that include at least one CDR, wherein the polypeptide binds VEGF-D.

In a related aspect, the invention contemplates a purified polypeptide comprising at least one CDR, wherein the framework regions of the heavy chain variable region and the framework regions of the light chain variable region comprise framework regions from a human antibody. In another embodiment, the framework regions of the heavy chain variable region and the framework regions of the light chain variable region are chemically altered by amino acid substitution to be more homologous to a human antibody sequence. For example, within each heavy chain framework region (H-FR1-4) it is contemplated that at least one, at least two, at least three, at least four, at least five, or at least six native framework region residues of the murine heavy chain variable region have been altered by amino acid substitution, and wherein within each light chain framework region (L-FR1-4), at least one, at least two, at least three, at least four, at least five or at least six native framework residues of the murine light chain variable region have been altered by amino acid substitution.

In another aspect, the invention provides a purified polypeptide comprising at least one CDR of a light chain variable region of a VEGF-D antibody, wherein the light chain variable region comprises an amino acid sequence at least 90% identical to the CDR sequences set out in SEQ ID NO: 47-49. In one embodiment, the polypeptide may be 90%, 95%, 96%, 97%, 98%, or 99% identical to the polypeptide of SEQ ID NO: 47, 48 or 49. In a further aspect, the invention provides a purified polypeptide comprising at least one CDR of a heavy chain variable region of a VEGF-D antibody, wherein the heavy chain variable region comprises an amino acid sequence at least 90% identical to the CDR sequences set out in SEQ ID NO: 50-52. In one embodiment, the polypeptide may be 90%, 95%, 96%, 97%, 98%, or 99% identical to the polypeptide of SEQ ID NO: 50, 51 or 52 VEGF-D binds both the VEGFR-2 and VEGFR-3 molecules on the cell surface and stimulates endothelial cell proliferation through these receptors. The present invention contemplates that a purified humanized antibody substance, antibody, polypeptide, or fragment according to the invention inhibits VEGF-D binding to VEGFR-3 and inhibits VEGF-D binding to VEGFR-2. It is further contemplated that a purified humanized antibody substance, antibody, polypeptide, or fragment according to the invention inhibits VEGF-D stimulation of endothelial cell growth.

The invention further provides an isolated polynucleotide comprising a nucleotide sequence that encodes a polypeptide comprising an antigen binding region of a VEGF-D antibody, wherein the antigen binding region comprises an amino acid sequence at least 90% identical to the amino acid sequence of SEQ ID NO: 37. In one embodiment, the polynucleotide encodes a polypeptide 90%, 95%, 96%, 97%, 98%, or 99% identical to the polypeptide of SEQ ID NO: 37. In an additional embodiment, the invention provides an isolated polynucleotide which comprises a nucleotide sequence that encodes the amino acid sequence of SEQ ID NO: 37.

In a related aspect, the invention contemplates an isolated polynucleotide comprising a nucleotide sequence that encodes a polypeptide comprising an antigen binding region of a VEGF-D antibody, wherein the antigen binding region comprises an amino acid sequence at least 90% identical to the amino acid sequence of SEQ ID NO: 39. In one embodiment, the polynucleotide encodes a polypeptide 90%, 95%, 96%, 97%, 98%, or 99% identical to the polypeptide of SEQ ID NO: 39. In an additional embodiment, the isolated polynucleotide comprises a nucleotide sequence that encodes the amino acid sequence of SEQ ID NO: 39.

In a further aspect, the invention provides an isolated polynucleotide comprising a nucleotide sequence that encodes a light chain polypeptide of a humanized VEGF-D antibody or antigen-binding fragment thereof, wherein the light chain polypeptide comprises a variable region amino acid sequence of SEQ ID NO: 37. The invention also provides an isolated polynucleotide comprising a nucleotide sequence that encodes a heavy chain polypeptide of a humanized VEGF-D antibody or antigen-binding fragment thereof, wherein the heavy chain polypeptide comprises a variable region amino acid sequence of SEQ ID NO: 39.

It is further contemplated that the polynucleotide comprising a nucleotide sequence that encodes a heavy chain polypeptide of a humanized VEGF-D antibody or antigen-binding fragment thereof, wherein the heavy chain polypeptide comprises a variable region amino acid sequence of SEQ ID NO: 39 further comprises a nucleotide sequence that encodes a light chain polypeptide of a humanized VEGF-D antibody or antigen-binding fragment thereof, wherein the light chain polypeptide comprises a variable region amino acid sequence of SEQ ID NO: 37.

In one aspect, the invention also contemplates an isolated polynucleotide comprising a nucleotide sequence that encodes the humanized antibody substance comprising an antibody that specifically binds Vascular Endothelial Growth Factor-D (VEGF-D), comprising i) a light chain variable region comprising a polypeptide comprising the amino acid sequence of SEQ ID NO: 37; ii) a heavy chain variable region comprising a polypeptide comprising the amino acid sequence of SEQ ID NO: 39; iii) a human antibody light chain constant region; and iv) a human antibody heavy chain constant region; or a fragment thereof that binds VEGF-D.

In a related aspect, the invention also contemplates an isolated polynucleotide comprising a nucleotide sequence that encodes an antibody substance or antibody that specifically binds Vascular Endothelial Growth Factor-D (VEGF-D), which comprises i) complementarity determining regions (CDR) from a mouse antibody and framework regions (FR) from a non-murine source, wherein the heavy chain variable region ($V_H$) comprises complementarity determining regions (CDR) with the amino acid sequences: H-CDR1 set out in SEQ ID NO: 50; H-CDR2 set out in SEQ ID NO: 51; H-CDR3 set out in SEQ ID NO: 52; ii) complementarity determining regions from a mouse antibody and framework regions from non-murine source, wherein the light chain variable region ($V_L$) comprises complementarity determining regions (CDR) with the amino acid sequences: L-CDR1 set out in SEQ ID NO: 47; L-CDR2 set out in SEQ ID NO: 48; L-CDR3 set out in SEQ ID NO: 49; iii) a human antibody light chain constant region; and iv) a human antibody heavy chain constant region; or a fragment thereof that binds VEGF-D.

In one embodiment, the polynucleotide encodes an antibody substance wherein the framework regions which are non-murine sequences are derived from a human antibody having sequence similarity to the mouse framework region. In another embodiment, the polynucleotide encodes an antibody substance wherein the framework regions are chemically synthesized to comprise substitute amino acids more commonly seen in human framework regions, but not identical to a human antibody framework region. This substitution is carried out using techniques common in the art, and any of the four framework regions in the antibody variable chain may contain one, two, three, four, or five substituted amino acids.

In a related embodiment, the polynucleotide residues of the heavy chain framework region described above which can be altered lie within regions designated H-FR1, H-FR2, H-FR3 and H-FR4, which surround the heavy chain CDR residues, and the polynucleotide residues of the light chain framework regions described above which can be altered lie within the regions designated L-FR1, L-FR2, L-FR3 and L-FR4, which surround the light chain CDR residues.

In one aspect, the invention provides an isolated polynucleotide encoding an humanized antibody substance described above wherein the light chain constant region is a kappa or lambda light chain. In a related aspect, the invention provides an isolated polynucleotide encoding an humanized antibody substance wherein the heavy chain constant region is selected from the group consisting of a constant region from an IgM chain, an IgG chain, an IgA chain, an IgE chain, an IgD chain, fragments thereof, and combinations thereof. In one embodiment, the isolated polynucleotide of the invention encodes heavy chain constant region comprises an IgG chain selected from the group consisting of IgG1, IgG2, IgG3, IgG4, fragments thereof, and combinations thereof. In a further embodiment, the constant region comprises at least one of $CH_1$, $CH_2$, and CH3 regions of a human IgG1 heavy chain constant region.

In a related aspect, the invention further contemplates an isolated polynucleotide comprising a nucleotide sequence that encodes a chimeric monoclonal antibody which specifically binds to Vascular Endothelial Growth Factor-D (VEGF-D), the monoclonal antibody comprising complementarity determining regions (CDR) of non-human origin from SEQ ID NOS: 37 and 39 and constant regions of light and heavy chains, said constant region being of human origin, wherein the biological function of specific binding to said VEGF-D is preserved.

In a further aspect, the invention provides an isolated polynucleotide comprising a nucleotide sequence that encodes a humanized antibody having binding specificity for Vascular Endothelial Growth Factor-D (VEGF-D), said humanized antibody comprising a light chain variable region comprising the amino acid sequence of SEQ ID NO: 37. In one embodiment, the isolated polynucleotide further comprises a heavy chain variable region from an antibody having binding specificity for VEGF-D.

In a another aspect, the invention provides an isolated polynucleotide comprising a nucleotide sequence that encodes a humanized antibody having binding specificity for Vascular Endothelial Growth Factor-D (VEGF-D), said humanized antibody comprising a heavy chain variable region comprising the amino acid sequence of SEQ ID NO: 39. In one embodiment, the polynucleotide further comprises a light chain variable region from an antibody having binding specificity for VEGF-D.

In another aspect, the invention contemplates an isolated polynucleotide comprising a nucleotide sequence that encodes a polypeptide comprising: (a) the amino acid sequence of SEQ ID NO: 37 fused to the amino acid sequence of SEQ ID NO: 39, or (b) fragments of (a) that include at least a portion of SEQ ID NO: 37 and SEQ ID NO: 39, wherein the polypeptide binds VEGF-D.

In another aspect, the invention provides an isolated polynucleotide comprising a nucleotide sequence that encodes a polypeptide which comprises a) complementarity determining regions (CDR) from a mouse antibody and framework regions (FR) from a non-murine source, wherein the heavy chain variable region ($V_H$) comprises complementarity determining regions (CDR) with the amino acid sequences: H-CDR1 set out in SEQ ID NO: 50; H-CDR2 set out in SEQ ID NO: 51; H-CDR3 set out in SEQ ID NO: 52; b) complementarity determining regions from a mouse antibody and framework regions from non-murine source, wherein the light chain variable region (V$_L$) comprises complementarity determining regions (CDR) with the amino acid sequences: L-CDR1 set out in SEQ ID NO: 47; L-CDR2 set out in SEQ ID NO: 48; L-CDR3 set out in SEQ ID NO: 49; iii) a human antibody light chain constant region; and iv) a human antibody heavy chain constant region; or a fragment of either (a) of (b) that binds VEGF-D.

In one embodiment, the polynucleotide encodes a polypeptide wherein the framework regions which are non-murine sequences are derived from a human antibody having sequence similarity to the mouse framework region. In another embodiment, the polynucleotide encodes a polypeptide wherein the framework regions are chemically synthesized to comprise substitute amino acids more commonly seen in human framework regions, but not identical to a human antibody framework region. This substitution is carried out using techniques common in the art, and any of the four framework regions in the antibody variable chain may contain at least one, two, three, four, five or six substituted amino acids.

In a related embodiment, the polynucleotide residues of the heavy chain framework region described above which can be altered lie within regions designated H-FR1, H-FR2, H-FR3 and H-FR4, which surround the heavy chain CDR residues, and the polynucleotide residues of the light chain framework regions described above which can be altered lie within the regions designated L-FR1, L-FR2, L-FR3 and L-FR4, which surround the light chain CDR residues.

Fragments of the amino acid sequence of either SEQ ID NO: 37 or 39 that include at least a portion of SEQ ID NO: 37 and SEQ ID NO: 39, and wherein the polypeptide binds VEGF-D, may be revealed in the CDR of the antibody, located within the variable regions of both the heavy chain and light chain. In one embodiment, the invention provides an isolated polynucleotide comprising a nucleotide sequence that encodes a polypeptide comprising (a) complementarity determining regions from a mouse antibody and framework regions from non-murine source, wherein the heavy chain variable region (V$_H$) comprises complementarity determining regions (CDR) with the amino acid sequences: H-CDR1 set out in SEQ ID NO: 50; H-CDR2 set out in SEQ ID NO: 51; H-CDR3 set out in SEQ ID NO: 52; (b) complementarity determining regions from a mouse antibody and framework regions from non-murine source, wherein the light chain variable region (V$_L$) comprises complementarity determining regions (CDR) with the amino acid sequences: L-CDR1 set out in SEQ ID NO: 47; L-CDR2 set out in SEQ ID NO: 48; L-CDR3 set out in SEQ ID NO: 49; and (c) fragments of (a) or (b) that include at least one CDR, wherein the polypeptide binds VEGF-D.

In a related embodiment, the invention provides a polynucleotide encoding a purified polypeptide comprising at least one CDR, or fragment thereof, wherein the framework regions of the heavy chain variable region and the framework regions of the light chain variable region comprise framework regions from a human antibody. In another embodiment, the framework regions of the heavy chain variable region and the framework regions of the light chain variable region are chemically altered by amino acid substitution to be more homologous to a human antibody sequence. For example, within each heavy chain framework region (H-FR1-4) it is contemplated that at least one, at least two, at least three, at least four, at least five, or at least six native framework region residues of the murine heavy chain variable region have been altered by amino acid substitution, and wherein within each light chain framework region (L-FR1-4), at least one, at least two, at least three, at least four, at least five or at least six native framework residues of the murine light chain variable region have been altered by amino acid substitution In an additional embodiment the invention contemplates an isolated polynucleotide comprising a nucleotide sequence that encodes a purified polypeptide comprising at least one CDR of a light chain variable region of a VEGF-D antibody, wherein the light chain variable region comprises an amino acid sequence at least 90% identical to CDR1, CDR2, or CDR3 sequences set out in SEQ ID NOS: 47-49.

In another embodiment, the invention provides an isolated polynucleotide comprising a nucleotide sequence that encodes a purified polypeptide comprising at least one CDR of a heavy chain variable region of a VEGF-D antibody, wherein the heavy chain variable region comprises an amino acid sequence at least 90% identical to CDR1, CDR2, or CDR3 sequences set out in SEQ ID NOS: 50-52.

In a further embodiment, the invention provides a polynucleotide comprising a nucleotide sequence encoding a humanized VEGF-D antibody or fragment thereof, wherein said antibody or fragment is immunospecific for VEGF-D, and wherein the antibody comprises at least one complementary determining region (CDR1, CDR2, CDR3) of the light chain variable region from the VEGF-D-specific antibody VD1/4A5 and at least one complementary determining region (CDR1, CDR2, CDR3) of the heavy chain variable of the VEGF-D-specific monoclonal antibody VD1/4A5.

The sequence of a CDR altered by insertion, substitution, or deletion may be included in the present invention, as long as it retains the activity of binding to human VEGF-D or neutralizes human VEGF-D. For example, it is contemplated that the CDRs used in the invention have a homology of 90-100% with each 4A5 antibody CDR set out in SEQ ID NOS: 47-52. In one embodiment the CDR sequences useful in making the humanized antibody substances have a homology of 95-100% with the native 4A5 CDRs. In a further embodiment, the sequences useful in making the humanized antibody substances have a homology of 98-100% with the native 4A5 CDRs.

The invention provides an expression vector comprising a polynucleotide encoding a humanized antibody substance, the antibody or polypeptide contemplated by the invention. The expression vector may be any expression vector suitable for transfection or transformation into, and expression of proteins in either prokaryotic or eukaryotic host cells. It is contemplated that the expression vector comprises an expression control sequence operably linked to a polynucleotide of the invention. In one embodiment, the vector comprises a nucleotide sequence that encodes a polypeptide comprising an amino acid sequence selected from the group consisting of SEQ ID NOS: 37, 39, and 47-52. It is contemplated that the expression vector comprises the nucleotide sequences set out in SEQ ID NO: 43 and 44 which encode plasmid insert DNA comprising the light chain variable region and heavy chain variable region, respectively.

The invention further provides a host cell transformed or transfected with a polynucleotide encoding a humanized antibody substance, antibody or polypeptide contemplated by the invention. In a further aspect, the invention provides a host cell transformed or transfected with the expression vector encoding a humanized antibody substance, antibody or polypeptide contemplated by the invention, wherein the cell expresses the antibody substance, antibody, or polypeptide encoded by the polynucleotide. The host cell of the invention may be any host cell suitable for expression of mammalian proteins. The host cell may be prokaryotic or eukaryotic. In a preferred embodiment, the host cell is a mammalian host cell.

In a related aspect the invention contemplates a method for producing an antibody substance, antibody, or polypeptide that specifically binds VEGF-D, comprising culturing a host cell transfected with an expression vector as contemplated by the invention in a culture medium, and recovering the antibody substance, antibody, or polypeptide from the cell or the medium. In one embodiment, the host cell is co-transfected with a polynucleotide comprising a nucleotide sequence that encodes a polypeptide comprising an amino acid sequence at least 90% identical to the amino acid sequence of SEQ ID NO: 37 and a polynucleotide comprising a nucleotide sequence that encodes a polypeptide comprising an amino acid sequence at least 90% identical to the amino acid sequence of SEQ ID NO: 39, wherein the cell expresses the polypeptide encoded by the polynucleotides.

In another embodiment, the host cell is co-transfected with a polynucleotide comprising a nucleotide sequence that encodes a light chain polypeptide of a humanized VEGF-D antibody or antigen-binding fragment thereof, wherein the light chain polypeptide comprises a variable region amino acid sequence of SEQ ID NO: 37, and a polynucleotide comprising a nucleotide sequence that encodes a heavy chain polypeptide of a humanized VEGF-D antibody or antigen-binding fragment thereof, wherein the heavy chain polypeptide comprises a variable region amino acid sequence of SEQ ID NO: 39, wherein the cell expresses an antibody substance comprising the polypeptides encoded by the polynucleotides, and wherein the antibody substance specifically binds VEGF-D.

In a further embodiment, a host cell transfected with an expression vector that expresses an antibody substance that specifically binds VEGF-D, is a host cell wherein the polynucleotide that encodes the light chain polypeptide comprises the sequence set out in SEQ ID NO: 43 coding for a light chain variable region and the polynucleotide that encodes the heavy chain polypeptide comprises the sequence set out in SEQ ID NO: 44 coding for the heavy chain variable region.

In another aspect, the invention provides a method for inhibiting VEGF-D mediated cell growth, migration, or differentiation, comprising administering to a human subject an antibody substance, antibody, polypeptide, or fragment according to the invention, in an amount effective to inhibit VEGF-D interaction with VEGFR-2 or VEGFR-3. It is contemplated that the humanized anti-VEGF-D antibody substance, antibody or polypeptide is administered in conjunction with a chemotherapeutic or radiotherapeutic agent. The chemotherapeutic agent or radiotherapeutic agent may be a member of the class of agents including an anti-metabolite; a DNA-damaging agent; a cytokine or growth factor; a covalent DNA-binding drug; a topoisomerase inhibitor; an anti-mitotic agent; an anti-tumor antibiotic; a differentiation agent; an alkylating agent; a methylating agent; a hormone or hormone antagonist; a nitrogen mustard; a radiosensitizer; and a photosensitizer. Specific examples of these agents are described elsewhere in the application.

It is contemplated that the humanized anti-VEGF-D antibody substance, antibody or polypeptide and the second agent are administered simultaneously, in the same formulation. It is further contemplated that the humanized anti-VEGF-D antibody substance and the second agent are administered at different times. In one embodiment, the humanized anti-VEGF-D antibody substance and the second agent are administered concurrently. In a second embodiment, the humanized anti-VEGF-D antibody substance is administered prior to the second agent. In a third embodiment, the humanized anti-VEGF-D antibody substance is administered subsequent to the second agent.

Generally, compositions of the invention are those that will inhibit tumor cell growth and metastasis by inhibiting angiogenesis and lymphangiogenesis and will act at lower concentrations, thereby permitting use of the compositions in a pharmaceutical composition at lower effective doses. Such compositions are suitable for administration by several routes such as intrathecal, parenteral, topical, intranasal, intravenous, intramuscular, inhalational, or any other clinically acceptable route of administration. Thus, in one embodiment, the invention provides a method of treating a subject, wherein the antibody substance, antibody or polypeptide is administered in an amount effective to inhibit angiogenesis or lymphangiogenesis in the subject. In a further embodiment, the subject is suffering from a condition or disorder resulting from aberrant angiogenesis or lymphangiogenesis.

The invention contemplates a method of the treating a subject suffering from a disorder or condition resulting from aberrant angiogenesis or lymphangiogenesis wherein the condition or disorder is cancer. In a related aspect, the invention provides a method for treating a subject suffering from a disorder or condition resulting from aberrant angiogenesis or lymphangiogenesis wherein the condition or disorder is selected from the group consisting of inflammation (chronic or acute), an infection, an immunological disease, arthritis, diabetes, retinopathy, psoriasis, arthopathies, congestive heart failure, fluid accumulation due to vascular permeability, lymphangioma, and lymphangiectasis. It is further contemplated that the subject with cancer is administered antibody substance, antibody or polypeptide of the invention in combination with a second agent selected from the group consisting of a chemotherapeutic agent, a radiotherapeutic agent, or radiation therapy.

The invention contemplates a pharmaceutical composition comprising a humanized anti-VEGF-D antibody substance, antibody, or polypeptide and a pharmaceutically acceptable carrier, diluent or excipient. In one embodiment, the humanized anti-VEGF-D antibody substance comprises humanized anti-VEGF-D antibody in combination with a second agent such as a chemotherapeutic agent; or humanized anti-VEGF-D antibody in a pharmaceutical composition comprising a growth factor or cytokine. Humanized anti-VEGF-D antibody substance, antibody, polypeptide, antibody fragments or variants are also contemplated for use in the pharmaceutical compositions of the invention.

The subject treated by the methods of the invention may be human, or any non-human animal model for human medical research, or an animal of importance as livestock or pets, (e.g., companion animals). In one variation, the subject has a disease or condition characterized by a need for modulation of angiogenesis or lymphangiogenesis, and administration of a composition comprising a humanized anti-VEGF-D antibody substance, antibody or polypeptide improves the animal's state, for example, by palliating disease symptoms, reducing unwanted angiogenesis or lymphangiogenesis, reducing tumor cell survival, or otherwise improving clinical symptoms. In a preferred embodiment, the subject to be treated is human.

One aspect of the invention is a chimeric or humanized antibody substance comprising:

(a) an antibody that specifically binds Vascular Endothelial Growth Factor-D (VEGF-D), comprising
  i) a light chain variable region comprising complementarity determining regions (L-CDR), wherein at least one of the L-CDR comprises an amino acid sequence selected from the group consisting of SEQ ID NOs: 47-49;

ii) a heavy chain variable region comprising complementarity determining regions (H-CDR), wherein at least one of the H-CDR comprises an amino acid sequence selected from the group consisting of SEQ ID NOs: 50-52;

iii) a human antibody light chain constant region; and iv) a human antibody heavy chain constant region; or (b) a fragment of (a) that binds VEGF-D.

The term antibody substance embraces antibodies which have the well known heavy and light chain structures of natural antibodies, as well as a variety of fragments of antibodies and engineered molecules such as single chain polypeptides that include the functional elements of antibodies for antigen binding, but may contain little or none of the constant region and other portions of an antibody that are not essential for antigen binding. A variety of VEGF-D binding molecules are described herein and represent antibody substances.

One preferred use for peptides that comprise VEGF-D binding fragments of humanized or chimeric antibodies of the invention is for use in generating multivalent ligand binding constructs, e.g., constructs that bind VEGF-D and other antigens, by recombining with fragments of other types of antibodies. Formation of bi-specific antibodies that recognize VEGF-D and at least one growth factor selected from VEGF-A, VEGF-B, VEGF-C, VEGF-E, PDGF-A, PDGF-B, PDGF-C, and PDGF-D is specifically contemplated.

In one variation, the L-CDR comprise the amino acid sequences set forth in SEQ ID NOs: 47-49 and the H-CDR comprise the amino acid sequences set forth in SEQ ID NOs: 50-52. However, recombination techniques taught herein enable the production of VEGF-D antibodies using fewer than all six of these CDR sequences.

Still further preferred aspects of the invention are set forth in the following numbered paragraphs:

1. A chimeric or humanized antibody substance comprising:

(a) an antibody that specifically binds Vascular Endothelial Growth Factor-D (VEGF-D), comprising i) a light chain variable region comprising complementarity determining regions (L-CDR), wherein at least one of the L-CDR comprises an amino acid sequence selected from the group consisting of SEQ ID NOs: 47-49;

ii) a heavy chain variable region comprising complementarity determining regions (H-CDR), wherein at least one of the H-CDR comprises an amino acid sequence selected from the group consisting of SEQ ID NOs: 50-52;

iii) a human antibody light chain constant region; and iv) a human antibody heavy chain constant region; or (b) a fragment of (a) that binds VEGF-D.

2. A chimeric or humanized antibody substance according to paragraph 1, wherein the L-CDR comprise the amino acid sequences set forth in SEQ ID NOs: 47-49 and the H-CDR comprise the amino acid sequences set forth in SEQ ID NOs: 50-52.

3. A chimeric or humanized antibody substance comprising:

(a) an antibody that specifically binds Vascular Endothelial Growth Factor-D (VEGF-D), comprising i) a light chain variable region comprising a polypeptide comprising the amino acid sequence of SEQ ID NO: 37;

ii) a heavy chain variable region comprising a polypeptide comprising the amino acid sequence of SEQ ID NO: 39;

iii) a human antibody light chain constant region; and iv) a human antibody heavy chain constant region; or (b) a fragment of (a) that binds VEGF-D.

4. A chimeric or humanized antibody substance comprising (a) an antibody that specifically binds Vascular Endothelial Growth Factor-D (VEGF-D), comprising i) heavy chain complementarity determining regions from a mouse antibody and framework regions from non-murine source, wherein the heavy chain variable region ($V_H$) comprises complementarity determining regions (CDR) with the amino acid sequences:

H-CDR1 set out in SEQ ID NO: 50
H-CDR2 set out in SEQ ID NO: 51
H-CDR3 set out in SEQ ID NO: 52 ii) light chain complementarity determining regions from a mouse antibody and framework regions from non-murine source, wherein the light chain variable region ($V_L$) comprises complementarity determining regions (CDR) with the amino acid sequences:

L-CDR1: set out in SEQ ID NO: 47
L-CDR2: set out in SEQ ID NO: 48
L-CDR3: set out in SEQ ID NO: 49;

iii) a human antibody light chain constant region; and iv) a human antibody heavy chain constant region; or (b) a fragment of (a) that binds VEGF-D.

5. The antibody substance of paragraph 4 wherein the framework regions of the heavy chain variable region and the framework regions of the light chain variable region comprise framework regions from a human antibody.

6 The antibody substance of paragraph 4 wherein the framework regions of the heavy chain variable region and the framework regions of the light chain variable region are chemically altered by amino acid substitution to be more homologous to a human antibody sequence.

7. The antibody substance of paragraph 5 wherein from 1 to 20 native framework region residues of the murine heavy chain variable region have been altered by amino acid substitution and wherein from 1 to 20 light chain variable region have been altered by amino acid substitution.

8 The antibody substance of any one of paragraphs 1-7 wherein the light chain constant region is a kappa or lambda light chain.

9. The antibody substance of any one of paragraphs 1-7 wherein the heavy chain constant region is selected from the group consisting of a constant region from an IgM chain, an IgG chain, an IgA chain, an IgE chain, an IgD chain, fragments thereof, and combinations thereof.

10. The antibody substance of any one of paragraphs 1-7 wherein the heavy chain constant region comprises an IgG chain selected from the group consisting of IgG1, IgG2, IgG3, IgG4, fragments thereof, and combinations thereof.

11. The antibody substance of paragraph 10 wherein the constant region comprises at least one of CH1, CH2, and CH3 regions of a human IgG1 heavy chain constant region.

12. The antibody substance of any one of paragraphs 1-7 that comprises a Fab fragment of the humanized antibody.

13. The antibody substance of any one of paragraphs 1-7 that is a monoclonal antibody.

14. A chimeric or humanized monoclonal antibody which specifically binds to Vascular Endothelial Growth Factor-D (VEGF-D), the monoclonal antibody comprising:

complementarity determining regions (CDR) selected from the group consisting of: the CDR sequences set forth in SEQ ID NOs: 47-52 and variants of the sequences with 1 or 2 amino acid substitutions; and constant regions of light and heavy chains, the constant region being of human origin, wherein the biological function of specific binding to the VEGF-D is preserved.

15. A chimeric or humanized monoclonal antibody according to paragraph 14 wherein the amino acid substitutions are conservative substitutions.

16. A chimeric or humanized monoclonal antibody that specifically binds to Vascular Endothelial Growth Factor-D (VEGF-D), the monoclonal antibody comprising complementarity determining regions (CDR) of non-human origin from SEQ ID NOS: 37 and 39 and constant regions of light and heavy chains, the constant region being of human origin, wherein the biological function of specific binding to the VEGF-D is preserved.

17. A chimeric or humanized antibody having binding specificity for Vascular Endothelial Growth Factor-D (VEGF-D), the humanized antibody comprising a light chain complementarity determining region amino acid sequences set forth in SEQ ID NOs: 47-49.

18. A chimeric or humanized antibody according to paragraph 17, wherein the antibody comprises a light chain variable region comprising the amino acid sequence of SEQ ID NO: 37.

19. A chimeric or humanized antibody according to paragraph 17 or 18 that further comprises a heavy chain variable region from an antibody having binding specificity for VEGF-D.

20. A chimeric or humanized antibody having binding specificity for Vascular Endothelial Growth Factor-D (VEGF-D), the humanized antibody comprising a heavy chain complementarity determining region amino acid sequences of SEQ ID NOs: 50-52.

21. A chimeric or humanized antibody according to paragraph 20, wherein the heavy chain variable region comprises the amino acid sequence of SEQ ID NO: 39.

22. A chimeric or humanized antibody according to paragraph 20 or 21 that further comprises a light chain variable region from an antibody having binding specificity for VEGF-D.

23. A purified polypeptide that binds VEGF-D, comprising an antigen binding region of a VEGF-D antibody, wherein the antigen binding region comprises an amino acid sequence at least 90% identical to the amino acid sequence of SEQ ID NO: 37, and wherein the antibody is humanized.

24. A purified polypeptide that binds VEGF-D, comprising an antigen binding region of a VEGF-D antibody, wherein the antigen binding region comprises an amino acid sequence at least 90% identical to the amino acid sequence of SEQ ID NO: 39, and wherein the antibody is humanized.

25. A purified polypeptide comprising:
 (a) the amino acid sequence of SEQ ID NO: 37 fused to the amino acid sequence of SEQ ID NO: 39, or
 (b) fragments of (a) that include at least a portion of SEQ ID NO: 37 and SEQ ID NO: 39,
 wherein the polypeptide binds VEGF-D.

26. A purified polypeptide fragment according to paragraph 25, wherein the fragment includes at least CDR sequences set forth in SEQ ID NOs: 47-52.

27. A purified polypeptide comprising
 (a) a polypeptide comprising complementarity determining regions from a mouse antibody and framework regions from non-murine source, wherein the heavy chain variable region ($V_H$) comprises complementarity determining regions (CDR) with the amino acid sequences:

H-CDR1 set out in SEQ ID NO: 50
H-CDR2 set out in SEQ ID NO: 51
H-CDR3 set out in SEQ ID NO: 52; fused to
a polypeptide comprising complementarity determining regions from a mouse antibody and framework regions from non-murine source, wherein the light chain variable region ($V_L$) comprises complementarity determining regions (CDR) with the amino acid sequences:
L-CDR1 set out in SEQ ID NO: 47
L-CDR2 set out in SEQ ID NO: 48
L-CDR3 set out in SEQ ID NO: 49; or
 (b) fragments of (a) that include at least one of the CDR, wherein the polypeptide binds VEGF-D.

28. A polypeptide fragment according to paragraph 27 that includes at least three of the CDRs.

29. A polypeptide fragment according to paragraph 27 that includes the six CDRs.

30. The purified polypeptide of paragraph 27 wherein the framework regions of the heavy chain variable region and the framework regions of the light chain variable region comprise framework regions from a human antibody.

31. The purified polypeptide of paragraph 27 wherein the framework regions of the heavy chain variable region and the framework regions of the light chain variable region are chemically altered by amino acid substitution to be more homologous to a human antibody sequence.

32. A chimeric or humanized antibody that binds VEGF-D,
 wherein the light chain variable region CDR comprise amino acid sequences at least 90% identical to the L-CDR1, L-CDR2, or L-CDR sequences set out in SEQ ID NO: 47-49; and
 wherein the heavy chain variable region CDR comprise an amino acid sequence at least 90% identical to the H-CDR1, H-CDR2, or H-CDR3 sequences set out in SEQ ID NO: 50-52.

33. A purified chimeric or humanized antibody substance, antibody, polypeptide, or fragment according to any one of paragraphs 1-32 that inhibits VEGF-D binding to VEGFR-3.

34. A purified chimeric or humanized antibody substance, antibody, polypeptide, or fragment according to any one of paragraphs 1-32 that inhibits VEGF-D binding to VEGFR-2.

35. A purified chimeric or humanized antibody substance, antibody, polypeptide, or fragment according to any one of any one of paragraphs 1-32 that inhibits VEGF-D stimulation of endothelial cell growth.

36. A composition comprising a purified chimeric or humanized antibody substance, antibody, polypeptide, or fragment according to any one of any one of paragraphs 1-35 in a pharmaceutically acceptable carrier.

37. An isolated polynucleotide comprising a nucleotide sequence that encodes the amino acid sequence of SEQ ID NO: 37.

38. An isolated polynucleotide comprising a nucleotide sequence that encodes the amino acid sequence of SEQ ID NO: 39.

39. An isolated polynucleotide comprising a nucleotide sequence that encodes the amino acid sequence of SEQ ID NO: 47.

40. An isolated polynucleotide comprising a nucleotide sequence that encodes the amino acid sequence of SEQ ID NO: 48.

41. An isolated polynucleotide comprising a nucleotide sequence that encodes the amino acid sequence of SEQ ID NO: 49

42. An isolated polynucleotide comprising a nucleotide sequence that encodes the amino acid sequence of SEQ ID NO: 50.

43. An isolated polynucleotide comprising a nucleotide sequence that encodes the amino acid sequence of SEQ ID NO: 51.

44. An isolated polynucleotide comprising a nucleotide sequence that encodes the amino acid sequence of SEQ ID NO: 52.

45. An isolated polynucleotide comprising a nucleotide sequence that encodes a light chain polypeptide of a chimeric or humanized VEGF-D antibody or antigen-binding fragment thereof, wherein the light chain polypeptide comprises L-CDR sequences set forth in SEQ ID NOs: 47-49.

46. An isolated polynucleotide comprising a nucleotide sequence that encodes a light chain polypeptide of a chimeric or humanized VEGF-D antibody or antigen-binding fragment thereof, wherein the light chain polypeptide comprises a variable region amino acid sequence of SEQ ID NO: 37.

47. An isolated polynucleotide comprising a nucleotide sequence that encodes a heavy chain polypeptide of a chimeric or humanized VEGF-D antibody or antigen-binding fragment thereof, wherein the heavy chain polypeptide comprises a H-CDR sequences set forth in SEQ ID NOs: 50-52.

48. An isolated polynucleotide according to paragraph 47, wherein the polynucleotide further comprises a nucleotide sequence that encodes a light chain polypeptide of a chimeric or humanized VEGF-D antibody or antigen-binding fragment thereof, wherein the light chain polypeptide comprises L-CDR sequences set forth in SEQ ID NOs: 47-49.

49. An isolated polynucleotide comprising a nucleotide sequence that encodes a heavy chain polypeptide of a chimeric or humanized VEGF-D antibody or antigen-binding fragment thereof, wherein the heavy chain polypeptide comprises a variable region amino acid sequence of SEQ ID NO: 39.

50. An isolated polynucleotide according to paragraph 33, wherein the polynucleotide further comprises a nucleotide sequence that encodes a light chain polypeptide of a chimeric or humanized VEGF-D antibody or antigen-binding fragment thereof, wherein the light chain polypeptide comprises a variable region amino acid sequence of SEQ ID NO: 37.

51. An isolated polynucleotide comprising a nucleotide sequence that encodes the antibody substance, antibody, polypeptide, or fragment according to any one of paragraphs 1-35.

52. A polynucleotide comprising a nucleotide sequence encoding a chimeric or humanized VEGF-D antibody or fragment thereof, wherein the antibody or fragment is immunospecific for VEGF-D, and wherein the antibody comprises at least one complementary determining region (CDR1, CDR2, CDR3) of the light chain variable region from the VEGF-D specific antibody VD1/4A5 and at least one complementary determining region (CDR1, CDR2, CDR3) of the heavy chain variable of the VEGF-D specific monoclonal antibody VD1/4A5.

53. An expression vector comprising a polynucleotide according to any one of paragraphs 37-52.

54. A host cell transformed or transfected with a polynucleotide according to any one of paragraphs 37-52.

55. A host cell transformed or transfected with the vector of paragraph 53, wherein the cell expresses the antibody substance, antibody, or polypeptide encoded by the polynucleotide.

56. A method for producing an antibody substance, antibody, or polypeptide that specifically binds VEGF-D, comprising culturing a host cell according to paragraph 55 in a culture medium and recovering the antibody substance, antibody, or polypeptide from the cell or the medium.

57. A host cell that is co-transfected with a polynucleotide according to paragraph 45 and a polynucleotide according to paragraph 47, wherein the cell expresses the polypeptides encoded by the polynucleotides.

58. A host cell according to paragraph 57, wherein the cell expresses an antibody substance comprising the polypeptides encoded by the polynucleotides, and wherein the antibody substance specifically binds VEGF-D.

59. A host cell according to paragraph 58, wherein the polynucleotide that encodes the light chain polypeptide comprises the sequence set out in SEQ ID NO: 43 coding for a light chain variable region and a the polynucleotide that encodes the heavy chain polypeptide comprises the sequence set out in SEQ ID NO: 44 coding for the heavy chain variable region.

60. A method for inhibiting VEGF-D mediated cell growth, migration, or differentiation, comprising administering to a human subject an antibody substance, antibody, polypeptide, or fragment according to any one of paragraphs 1-35, in an amount effective to inhibit VEGF-D interaction with VEGFR-2 or VEGFR-3.

61. A method according to paragraph 60, wherein the antibody is administered in an amount effective to inhibit angiogenesis or lymphangiogenesis in the human subject.

62. The method of paragraph 61 wherein the subject is suffering from a condition or disorder resulting from aberrant angiogenesis or lymphangiogenesis.

63. The method of paragraph 62 wherein the condition or disorder is cancer.

64. The method of paragraph 63 wherein the anti-VEGF-D antibody substance, antibody or polypeptide is administered in combination with a second agent selected from the group consisting of a chemotherapeutic agent, a radiotherapeutic agent, or radiation therapy.

65. The method of paragraph 62 wherein the condition or disorder is selected from the group consisting of inflammation (chronic or acute), an infection, an immunological disease, arthritis, diabetes, retinopathy, psoriasis, arthopathies, congestive heart failure, fluid accumulation due to vascular permeability, lymphangioma, and lymphangiectasis.

Additional features and variations of the invention will be apparent to those skilled in the art from the entirety of this application, including the detailed description, and all such features are intended as aspects of the invention. It should be understood, however, that the detailed description and the specific examples, while indicating preferred embodiments of the invention, are given by way of illustration only, because various changes and modifications within the spirit and scope of the invention will become apparent to those skilled in the art from this detailed description.

Moreover, features of the invention described herein can be re-combined into additional embodiments that also are intended as aspects of the invention, irrespective of whether the combination of features is specifically mentioned above as an aspect or embodiment of the invention. Also, only those limitations that are described herein as critical to the invention should be viewed as such; variations of the invention lacking features that have not been described herein as critical are intended as aspects of the invention.

With respect to aspects of the invention that have been described as a set or genus, every individual member of the set or genus is intended, individually, as an aspect of the invention, even if, for brevity, every individual member has not been specifically mentioned herein. When aspects of the invention that are described herein as being selected from a genus, it should be understood that the selection can include mixtures of two or more members of the genus.

In addition to the foregoing, the invention includes, as an additional aspect, all embodiments of the invention narrower in scope in any way than the variations specifically described herein. Although the applicant(s) invented the full scope of the claims appended hereto, the claims appended hereto are not intended to encompass within their scope the prior art work of others. Therefore, in the event that statutory prior art within the scope of a claim is brought to the attention of the applicants by a Patent Office or other entity or individual, the applicant(s) reserve the right to exercise amendment rights under applicable patent laws to redefine the subject matter of such a claim to specifically exclude such statutory prior art or obvious variations of statutory prior art from the scope of such a claim. Variations of the invention defined by such amended claims also are intended as aspects of the invention.

BRIEF DESCRIPTION OF THE DRAWINGS

FIG. 1 sets out the nucleotide and amino acid sequence for an anti-VEGF-D light chain variable region (1A) (SEQ ID NO: 36 and 37, respectively) and heavy chain variable region (1B) (SEQ ID NO: 38 and 39, respectively).

FIG. 2 sets out the nucleotide sequence (SEQ ID NO: 45) of a plasmid for expressing a chimeric anti-VEGF-D antibody light chain variable region.

FIG. 3 sets out the nucleotide sequence (SEQ ID NO: 46) of a plasmid for expression of a chimeric anti-VEGF-D antibody heavy chain variable region.

DETAILED DESCRIPTION OF THE INVENTION

Figure 4:
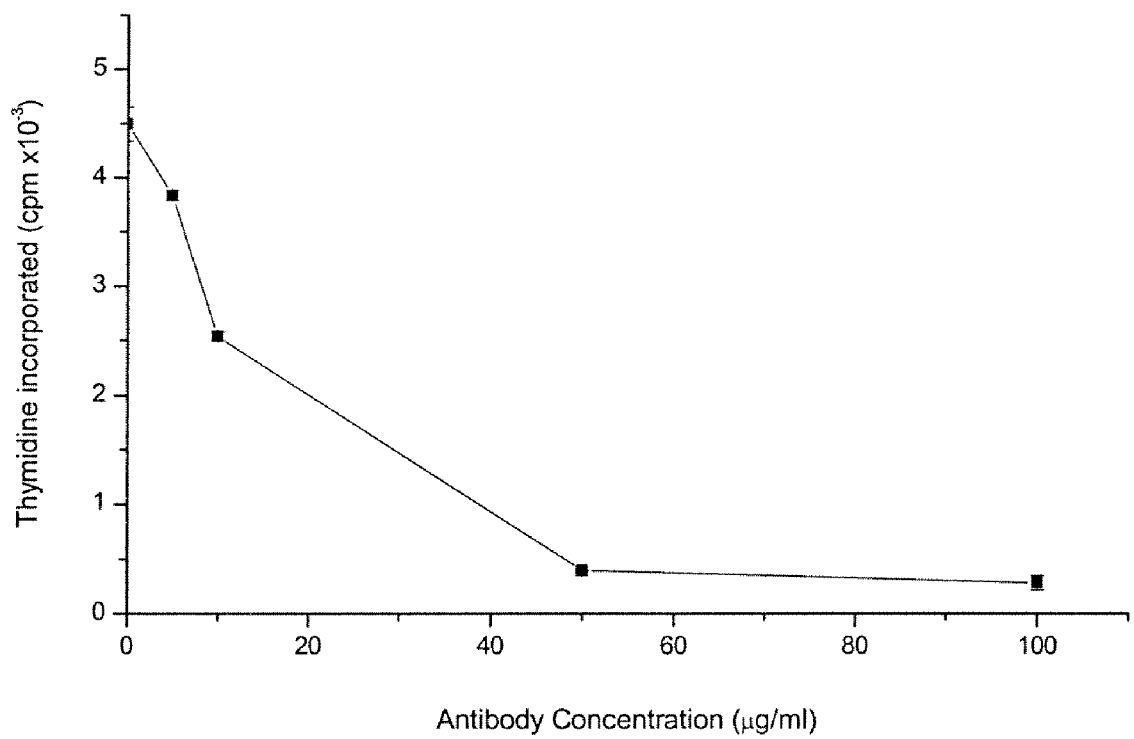
FIG. 4 is a graph depicting the cell growth (measured by Thymidine incorporation) in response to VEGF-D mixed with varying concentrations of a chimeric anti-VEGF-D antibody of VEGFR-2 transfected cells.

The present invention addresses the need in the art for new therapeutics that can specifically interfere with the angiogenesis or lymphangiogenesis involved in tumor growth and metastasis and other pathological conditions. The present invention provides chimeric and provides humanized VEGF-D antibodies which will more specifically regulate VEGF-D signaling through its receptors and provide a more effective therapy for patients suffering from aberrant lymphangiogenesis and angiogenesis.

In order that the invention may be more completely understood, several definitions are set forth.

The term "chimeric antibody" is generally used to refer to an antibody substance containing constant domains from one species and the variable domains from a second, or more generally, containing stretches of amino acid sequence from at least two species. The term "humanized" when used in relation to antibodies is used to refer to antibodies having at least CDR regions from a nonhuman source which are engineered to have a structure and immunological function more similar to true human antibodies than the original source antibodies. For example, humanizing can involve grafting CDR from a non-human antibody, such as a mouse antibody, into a human antibody substance. Humanizing also can involve select amino acid substitutions to make a non-human sequence look more like a human sequence. Use of the terms "chimeric or humanized" herein is not meant to be mutually exclusive, and rather, is meant to encompass chimeric antibodies, humanized antibodies, and chimeric antibodies that have been further humanized. Except where context otherwise indicates, statements about (properties of, uses of, testing, and so on) chimeric antibodies of the invention apply to humanized antibodies of the invention, and statements about humanized antibodies of the invention pertain also to chimeric antibodies. Likewise, except where context dictates, such statements also should be understood to be applicable to antibody substances of the invention.

The term "derivative" refers to polypeptides chemically modified by such techniques as ubiquitination, labeling (e.g., with radionuclides or various enzymes), covalent polymer attachment such as pegylation (derivatization with polyethylene glycol) and insertion or substitution by chemical synthesis of amino acids such as ornithine, which do not normally occur in human proteins.

"Detectable moiety" or a "label" refers to a composition detectable by spectroscopic, photochemical, biochemical, immunochemical, or chemical means. For example, useful labels include $^{32}$P, $^{35}$S, fluorescent dyes, electron-dense reagents, enzymes (e.g., as commonly used in an ELISA), biotin-streptavadin, dioxigenin, haptens and proteins for which antisera or monoclonal antibodies are available, or nucleic acid molecules with a sequence complementary to a target. The detectable moiety often generates a measurable signal, such as a radioactive, chromogenic, or fluorescent signal, that can be used to quantitate the amount of bound detectable moiety in a sample. Methods for attaching a detectable moiety are described below.

"Humanized anti-VEGF-D antibody" "humanized VEGF-D antibody composition" and "humanized anti-VEGF-D antibody substance" as used herein refer to compositions that comprise the variable, antigen binding regions of a non-human (e.g., murine) anti-VEGF-D antibody, or a variant or fragment thereof, fused or linked to a human constant chain and framework region. Humanized VEGF-D antibody compositions contemplated for use in the invention include humanized VEGF-D antibody alone in a pharmaceutically acceptable carrier, humanized VEGF-D antibody in combination with a second agent such as a chemotherapeutic or radiotherapeutic agent. Humanized VEGF-D antibody composition also includes humanized VEGF-D antibody in a pharmaceutical composition additionally comprising a growth factor or cytokine, as described below.

Chimeric and humanized VEGF-D antibodies as described herein are useful for making multivalent antibody substances as described in U.S. Provisional Patent Application 60/550, 511, co-filed on Mar. 5, 2004, directed to Multivalent antibody materials and methods for VEGF/PDGF family of growth factors, and related, co-filed International patent application Ser. No. 11/075,400, both incorporated herein by reference in their entirety.

Chimeric and Human antibody substances of the invention also are useful for making binding constructs as described in U.S. Provisional Application No. 60/550,907, co-filed on Mar. 5, 2004, directed to growth factor constructs materials and methods, and related, co-filed International patent application Ser. No. 11/075,047, both incorporated herein by reference in their entirety.

"Heavy chain variable region" as used herein refers to the region of the antibody molecule comprising at least one complementarity determining region (CDR) of said antibody heavy chain variable domain. The heavy chain variable region may contain one, two, or three CDR of said antibody heavy chain.

"Light chain variable region" as used herein refers to the region of an antibody molecule, comprising at least one complementarity determining region (CDR) of said antibody light chain variable domain. The light chain variable region may contain one, two, or three CDR of said antibody light chain, which may be either a kappa or lambda light chain depending on the antibody.

As used herein, "potentiate" (in the context of cancer therapy) refers to activity of humanized VEGF-D antibody, which, when administered in conjunction with a second agent, such as a chemotherapeutic agent, a radiotherapeutic agent, or a cytokine of growth factor, inhibits of tumor growth and metastasis beyond that of administration the second agent alone, or inhibits equally but with reduced side effects.

The term "specific for," when used to describe antibodies of the invention, indicates that the antibodies, through their variable regions, recognize and bind the polypeptide with a detectable preference (i.e., able to distinguish the polypeptide of interest from other known polypeptides of the same family, by virtue of measurable differences in binding affinity, despite the possible existence of localized sequence identity, homology, or similarity between family members). By "binds VEGF-D" or "specifically binds VEGF-D" is meant that the antibody or substance of the invention binds the fully processed form of VEGF-D, VEGF-DΔNΔC. Preferred antibodies also bind less processed forms of the VEGF-D molecule, including intermediate and unprocessed VEGF-D.

Specific antibodies may also interact with other proteins (for example, S. aureus protein A or other antibodies in ELISA techniques) through interactions with sequences outside the variable region of the antibodies, and in particular, in the constant region of the molecule. Screening assays to determine binding specificity of an antibody of the invention are well known and routinely practiced in the art. See Harlow et al. (Eds), Antibodies A Laboratory Manual; Cold Spring Harbor Laboratory; Cold Spring Harbor, N.Y. (1988), Chapter 6. Antibodies of the invention can be produced using any known method.

A "therapeutically effective amount" or "effective amount" refers to that amount of the compound sufficient to result in amelioration of symptoms, for example, treatment, healing, prevention or amelioration of the relevant medical condition, or an increase in rate of treatment, healing, prevention or amelioration of such conditions. When applied to an individual active ingredient, administered alone, a therapeutically effective dose refers to that ingredient alone. When applied to a combination, a therapeutically effective dose refers to combined amounts of the active ingredients that result in the therapeutic effect, whether administered in combination, serially or simultaneously.

"Antibody Variant" as used herein refers to a humanized anti-VEGF-D antibody polypeptide sequence that contains at least one amino acid substitution, deletion, or insertion in the variable region relative to the original VEGF-D antibody variable region domains.

VEGF/VEGFR Family Members

VEGF-C (SEQ ID NO: 1 and 2) was isolated from conditioned media of PC-3 prostate adenocarcinoma cell line (CRL1435) by selecting for a component of medium that caused tyrosine phosphorylation of the endothelial cell-specific receptor tyrosine kinase Flt4, using cells transfected to express Flt4. VEGF-C was purified using affinity chromatography with recombinant Flt4, and was cloned from a PC-3 cDNA library. Its isolation and characteristics are described in detail in Joukov et al, *EMBO J.* 15:290-298, 1996, and U.S. Pat. Nos. 6,221,839; 6,235,713; 6,361,946; 6,403,088; and 6,645,933 and International Patent Publ. Nos. WO 97/05250, WO 98/07832, and WO 98/01973, incorporated herein by reference.

VEGF-C is originally expressed as a larger precursor protein, prepro-VEGF-C, having extensive amino- and carboxy-terminal peptide sequences flanking a VEGF homology domain (VHD), with the C-terminal peptide containing tandemly repeated cystine residues in a motif typical of Balbiani ring 3 protein. The prepro-VEGF-C polypeptide is processed in multiple stages to produce a mature and most active VEGF-C polypeptide (ΔNΔC VEGF-C) of about 21-23 kD (as assessed by SDS-PAGE under reducing conditions). Such processing includes cleavage of a signal peptide (SEQ ID NO: 2, residues 1-31); cleavage of a carboxyl-terminal peptide (corresponding approximately to amino acids 228-419 of SEQ ID NO: 2 to produce a partially-processed form of about 29 kD; and cleavage (apparently extracellularly) of an amino-terminal peptide (corresponding approximately to amino acids 32-102 of SEQ ID NO: 2) to produced a fully-processed mature form of about 21-23 kD. Experimental evidence demonstrates that partially-processed forms of VEGF-C (e.g., the 29 kD form) are able to bind the Flt4 (VEGFR-3) receptor, whereas high affinity binding to VEGFR-2 occurs only with the fully processed forms of VEGF-C. Moreover, it has been demonstrated that amino acids 103-227 of SEQ ID NO: 2 are not all critical for maintaining VEGF-C functions. A polypeptide consisting of amino acids 112-215 (and lacking residues 103-111 and 216-227) of SEQ ID NO: 2 retains the ability to bind and stimulate VEGF-C receptors, and it is expected that a polypeptide spanning from about residue 131 to about residue 211 will retain VEGF-C biological activity. The cysteine residue at position 156 has been shown to be important for VEGFR-2 binding ability. It appears that VEGF-C polypeptides naturally associate as non-disulfide linked dimers.

A mutant VEGF-C (VEGF-C $\Delta C_{156}$), in which a single cysteine at position 156 is either substituted by another amino acid or deleted, loses the ability to bind VEGFR-2 but remains capable of binding and activating VEGFR-3 (U.S. Pat. No. 6,130,071 and International Patent Publication No. WO 98/33917). Exemplary substitutions at amino acid 156 of SEQ. ID NO: 2 include substitution of a serine residue for the cysteine at position 156 (VEGF-C C156S). VEGF-C is involved in the regulation of lymphangiogenesis: when VEGF-C was overexpressed in the skin of transgenic mice, a hyperplastic lymphatic vessel network was observed, suggesting that VEGF-C induces lymphatic growth (Jeltsch et al., *Science*, 276:1423-1425, 1997). Continued expression of VEGF-C in the adult also indicates a role in maintenance of differentiated lymphatic endothelium [Ferrara, *J Mol Med* 77:527-543 (1999)]. VEGF-C also shows angiogenic properties: it can stimulate migration of bovine capillary endothelial (BCE) cells in collagen and promote growth of human endothelial cells [see, e.g., U.S. Pat. No. 6,245,530; U.S. Pat. No. 6,221,839; and International Patent Publication No. WO 98/33917, incorporated herein by reference].

VEGF-D (SEQ ID NO: 3 and 4) was isolated as an incomplete fragment from a human breast cDNA library, commercially available from Clontech, by screening with an expressed sequence tag obtained from a human cDNA library designated "Soares Breast 3NbHBst" as a hybridization probe (Achen et al., *Proc. Natl. Acad. Sci. USA* 95: 548-553, 1998). Full length VEGF-D was subsequently cloned from a human lung cDNA library. Its isolation and characteristics are described in detail in International Patent Application No. PCT/US97/14696 (WO98/07832), incorporated herein by reference.

The VEGF-D gene is broadly expressed in the adult human, but is not ubiquitously expressed. VEGF-D is strongly expressed in heart, lung and skeletal muscle. Intermediate levels of VEGF-D are expressed in spleen, ovary, small intestine and colon, and a lower expression occurs in kidney, pancreas, thymus, prostate and testis. No VEGF-D mRNA was detected in RNA from brain, placenta, liver or peripheral blood leukocytes.

VEGF-D is structurally and functionally most closely related to VEGF-C. Like VEGF-C, VEGF-D is initially expressed as a prepro-peptide that undergoes N-terminal and C-terminal proteolytic processing, and forms non-covalently linked dimers. VEGF-D stimulates mitogenic responses in endothelial cells in vitro. During embryogenesis, VEGF-D is expressed in a complex temporal and spatial pattern, and its expression persists in the heart, lung, and skeletal muscles in adults. Isolation of a biologically active fragment of VEGF-D designated VEGF-D ΔNΔC, is described in International Patent Publication No. WO 98/07832, incorporated herein by reference.

The prepro-VEGF-D polypeptide has a putative signal peptide of 21 amino acids and is apparently proteolytically processed in a manner analogous to the processing of prepro-VEGF-C. A "recombinantly matured" VEGF-D, VEGF-D ΔNΔC, containing amino acid residues 93 to 201, and lacking residues 1-92 and 202-354 of SEQ ID NO: 4 retains the ability to activate receptors VEGFR-2 and VEGFR-3, and appears to associate as non-covalently linked dimers. Thus, preferred VEGF-D polynucleotides include those polynucleotides that comprise a nucleotide sequence encoding amino acids 93-201 of SEQ ID NO: 4.

The predominant intracellular form of human VEGF-D is a homodimeric propeptide that consists of the VEGF/PDGF Homology Domain (VHD) and the N- and C-terminal propeptides. After secretion, this polypeptide is proteolytically cleaved (Stacker et al., *J Biol Chem* 274:32127-32136, 1999). The human VEGF-D VHD consists of residues 93 to 201 of full length VEGF-D and contains the binding sites for both VEGFR-2 and VEGFR-3.

The description of the cloning of the mouse homolog of VEGF-D is also found in Intl. Patent Application PCT/US97/14696 (WO 98/07832). With the mouse, it was found that there are two isoforms. The longer amino acid sequence is designated mVEGF-D1, and the shorter sequence is designated mVEGF-D2. The nucleotide sequences of the cDNAs encoding mVEGF-D1 and mVEGF-D2 are found in SEQ ID NOs: 5 and 7, respectively. The deduced amino acid sequences for mVEGF-D1 and mVEGF-D2 are found in SEQ ID NOs: 6 and 8, respectively. The differences between the amino acid sequences are:

i) an insertion of five amino acids (DFSFE) (SEQ ID NO: 9) after residue 30 in mVEGF-D1 in comparison to mVEGF-D2;

ii) complete divergence of the C-terminal ends after residue 317 in mVEGF-D1 and residue 312 in mVEGF-D2, which results in mVEGF-D1 being considerably longer.

VEGF-D is highly conserved between mouse and man. 85% of the amino acid residues of human VEGF-D are identical in mouse VEGF-D1. It is also predicted that the predominant intracellular form of mouse VEGF-D is a homodimeric propeptide that consists of the VEGF/PDGF Homology Domain (VHD) and the N- and C-terminal propeptides. The mouse VHD consists of residues 92 to 201 of the full length mouse VEGF-D2 (SEQ ID NO: 8).

The biological functions of the different members of the VEGF family are currently being elucidated. Of particular interest are the properties of VEGF-D and VEGF-C. These proteins share 48% amino acid sequence identity and bind to both VEGFR-2 and VEGFR-3, localized on vascular and lymphatic endothelial cells, respectively. Both factors are mitogenic for endothelial cells in vitro. Recently, VEGF-C was shown to be angiogenic in the mouse cornea model and in the avian chorioallantoic membrane (Cao et al., *Proc. Natl. Acad. Sci. USA* 95: 14389-14394, 1998) and was able to induce angiogenesis in the setting of tissue ischemia (Witzenbichler et al., *Am. J. Pathol.* 153: 381-394, 1998). Furthermore, VEGF-C stimulated lymphangiogenesis in the avian chorioallantoic membrane (Oh et al., *Dev. Biol.* 188: 96-109, 1997) and in a transgenic mouse model (Jeltsch et al., *Science* 276:1423-1425, 1997). VEGF-D was shown to be angiogenic in the rabbit cornea (Marconcini et al., *Proc. Natl. Acad. Sci. USA* 96: 9671-9676, 1999).

Given that VEGF-D, like VEGF-C, binds and activates VEGFR-3, a receptor thought to signal for lymphangiogenesis (Taipale et al., *Cur. Topics Micro. Immunol.* 237: 85-96, 1999), it is highly likely that VEGF-D is lymphangiogenic. However, the angiogenic and lymphangiogenic capacity of VEGF-D has been reported by Veikkola et al. (*EMBO J.* 20:1223-31, 2001) and Rissanen et al. (*Circ Res.* 2003 92:1098-106, 2003), which showed that VEGF-D is a strong inducer of both angiogenesis and lymphangiogenesis in skeletal muscle.

Evidence indicates that VEGF-D and VEGF-C have importance for the malignancy of tumors, since angiogenesis is necessary for tumor growth and since metastases can spread via either blood vessels or lymphatic vessels (PCT/US99/23525 and Jussila et al., *Cancer Res.* 58:1599-1604. 1998). Therefore, molecules which stimulate angiogenesis or lymphangiogenesis could contribute toward malignancy.

Chemotherapeutics Agents and Cytokines

A combination of a chimeric or humanized anti-VEGF-D antibody with one or more additional therapeutics/second agents in methods of the invention may reduce the amount of either agent needed as a therapeutically effective dosage, and thereby reduce any negative side effects the agents may induce in vivo. Additional therapeutics or second agents contemplated for use in combination with a chimeric or humanized anti-VEGF-D antibody include a growth factor or cytokine, a chemotherapeutic agent, a radiotherapeutic agent, or radiation therapy.

Any chemotherapeutic or radiotherapeutic agent may be suitable for use in combination with chimeric or humanized anti-VEGF-D antibody in a composition or method of the invention, and may be identified by means well known in the art. Examples of suitable chemotherapeutic and radiotherapeutic agents include, but are not limited to: an anti-metabolite; a DNA-damaging agent; a cytokine or growth factor useful as a chemotherapeutic agent; a covalent DNA-binding drug; a topoisomerase inhibitor; an anti-mitotic agent; an anti-tumor antibiotic; a differentiation agent; an alkylating agent; a methylating agent; a hormone or hormone antagonist; a nitrogen mustard; a radiosensitizer; a photosensitizer; a radiation source, optionally together with a radiosensitizer or photosensitizer; or other commonly used therapeutic agents.

Specific examples of chemotherapeutic agents useful in methods of the present invention are listed in the table below.

Chimeric or humanized anti-VEGF-D antibody compositions administered may also include cytokines and growth factors that are effective in inhibiting tumor metastasis, and wherein the cytokine or growth factor has been shown to have an antiproliferative effect on at least one cell population. Such cytokines, lymphokines, growth factors, or other hematopoietic factors include M-CSF, GM-CSF, TNF, IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IFN, TNFα, TNF1, TNF2, G-CSF, Meg-CSF, GM-CSF, thrombopoietin, stem cell factor, and erythropoietin. Additional growth factors for use in pharmaceutical compositions of the invention include angiogenin, bone morphogenic protein-1, bone morphogenic protein-2, bone morphogenic protein-3, bone morphogenic protein-4, bone morphogenic protein-5, bone morphogenic protein-6, bone morphogenic protein-7, bone morphogenic protein-8, bone morphogenic protein-9, bone morphogenic protein-10, bone morphogenic protein-11, bone morphogenic protein-12, bone morphogenic protein-13, bone morphogenic protein-14, bone morphogenic protein-15, bone morphogenic protein receptor IA, bone morphogenic protein receptor IB, brain derived neurotrophic factor, ciliary neutrophic factor, ciliary neutrophic factor receptor α, cytokine-induced neutrophil chemotactic factor 1, cytokine-induced neutrophil, chemotactic factor 2 α, cytokine-induced neutrophil chemotactic factor 2 β, β endothelial cell growth factor, endothelin 1, epithelial-derived neutrophil attractant, glial cell line-derived neutrophic factor receptor α 1, glial cell line-derived neutrophic factor receptor α 2, growth related protein, growth related protein α, growth related protein β, growth related protein γ, heparin binding epidermal growth factor, hepatocyte growth factor, hepatocyte growth factor receptor, insulin-like growth factor I, insulin-like growth factor receptor, insulin-like growth factor II, insulin-like growth factor binding protein, keratinocyte growth factor, leukemia inhibitory factor, leukemia inhibitory factor receptor α, nerve growth factor nerve growth factor receptor, neurotrophin-3, neurotrophin-4, pre-B cell growth stimulating factor, stem cell factor, stem cell factor receptor, transforming growth factor α, transforming growth factor β, transforming growth factor β1, transforming growth factor β1.2, transforming growth factor β2, transforming growth factor β3, transforming growth factor β5, latent transforming growth factor β1, transforming growth factor β binding protein I, transforming growth factor β binding protein II, transforming growth factor β binding protein III, tumor necrosis factor receptor type I, tumor necrosis factor receptor type II, urokinase-type plasminogen activator receptor, and chimeric proteins and biologically or immunologically active fragments thereof.

Advantageously, when a second agent is used in combination with the chimeric or humanized anti-VEGF-D antibodies of the present invention, the results obtained are synergistic. That is to say, the effectiveness of the combination therapy of a chimeric or humanized anti-VEGF-D antibody and the second agent is synergistic, i.e., the effectiveness is greater than the effectiveness expected from the additive individual effects of each. Therefore, the dosage of the second agent can be reduced and thus, the risk of the toxicity problems and other side effects is concomitantly reduced.

Compositions of the invention are also readily adaptable for use in assay systems, for example, assaying cancer cell growth and properties thereof using chimeric or humanized anti-VEGF-D antibody compositions described herein, as well as identifying compounds that affect cancer cell growth and metastasis.

TABLE 1

| Alkylating agents |
| --- |
| Nitrogen mustards | mechlorethamine
cyclophosphamide
ifosfamide
melphalan
chlorambucil

TABLE 1-continued

| Nitrosoureas |
| --- | carmustine (BCNU)
lomustine (CCNU)
semustine (methyl-CCNU)
Ethylenimine/Methyl-melamine thriethylenemelamine (TEM)
triethylene thiophosphoramide
(thiotepa)
hexamethylmelamine
(HMM, altretamine)
Alkyl sulfonates busulfan
Triazines dacarbazine (DTIC)
Antimetabolites Folic Acid analogs
methotrexate
Trimetrexate
Pemetrexed
Multi-targeted antifolate
Pyrimidine analogs
5-fluorouracil
fluorodeoxyuridine
gemcitabine
cytosine arabinoside
(AraC, cytarabine)
5-azacytidine
2,2'-difluorodeoxy-cytidine
Purine analogs
6-mercaptopurine
6-thioguanine
azathioprine
2'-deoxycoformycin
(pentostatin)
erythrohydroxynonyl-adenine
(EHNA)
fludarabine phosphate
2-chlorodeoxyadenosine
(cladribine, 2-CdA)
Type I Topoisomerase Inhibitors camptothecin
topotecan
irinotecan
Natural products
Antimitotic drugs paclitaxel
Vinca alkaloids
vinblastine (VLB)
vincristine
vinorelbine
Taxotere ® (docetaxel)
estramustine
estramustine phosphate
Epipodophylotoxins etoposide
teniposide
Antibiotics actimomycin D
daunomycin (rubido-mycin)
doxorubicin (adria-mycin)
mitoxantroneidarubicin
bleomycinsplicamycin
(mithramycin)
mitomycinC
dactinomycin TABLE 1-continued Enzymes L-asparaginase
Biological response modifiers interferon-alpha
IL-2
G-CSF
GM-CSF
Differentiation Agents retinoic acid derivatives
Radiosensitizers metronidazole
misonidazole
desmethylmisonidazole
pimonidazole
etanidazole
nimorazole
RSU 1069
EO9
RB 6145
SR4233
nicotinamide
5-bromodeozyuridine
5-iododeoxyuridine
bromodeoxycytidine
Miscellaneous agents
Platinium coordination complexes cisplatin
Carboplatin
oxaliplatin
Anthracenedione mitoxantrone
Substituted urea hydroxyurea
Methylhydrazine derivatives N-methylhydrazine (MIH)
procarbazine
Adrenocortical suppressant mitotane (o,p'-DDD)
ainoglutethimide
Cytokines interferon (*, *, *)
interleukin-2
Hormones and antagonists
Adrenocorticosteroids/antagonists prednisone and equivalents
dexamethasone
ainoglutethimide
Progestins hydroxyprogesterone caproate
medroxyprogesterone acetate
megestrol acetate
Estrogens diethylstilbestrol
ethynyl estradiol/equivalents
Antiestrogen tamoxifen
Androgens testosterone propionate
fluoxymesterone/equivalents
Antiandrogens flutamide
gonadotropin-releasing TABLE 1-continued hormone analogs
leuprolide
Nonsteroidal antiandrogens flutamide
Photosensitizers hematoporphyrin derivatives
Photofrin ®
benzoporphyrin derivatives
Npe6
tin etioporphyrin (SnET2)
pheoboride-a
bacteriochlorophyll-a
naphthalocyanines
phthalocyanines
zinc phthalocyanines Antibodies VEGF-D antibodies of the invention are useful for modulating VEGF-D mitogenic activity by inhibiting VEGF-D stimulation of VEGF-D receptors such as VEGFR-3 or VEGFR-2. The invention provides VEGF-D antibody substances (e.g., monoclonal antibodies, single chain antibodies, chimeric antibodies, humanized antibodies, bifunctional/bispecific antibodies, human antibodies, and complementary determining region (CDR)-grafted antibodies, polypeptides that include CDR sequences and that specifically recognize VEGF-D, and other molecules designed from antigen-binding regions of antibodies) for administration to human beings that are chimeric or humanized, i.e., that have fully human or largely human antibody structure so as to minimize antigenicity of the antibody itself and otherwise interact with a human immune system in a manner that mimics a true human antibody. Exemplary antibodies are human antibodies which are produced and identified according to methods described in WO93/11236, incorporated herein by reference in its entirety. Antibody fragments, including Fab, Fab', $F(ab')_2$, and Fv, are also provided by the invention.

A monoclonal antibody to VEGF-D may be prepared by using any technique which provides for the production of antibody molecules by continuous cell lines in culture. These include but are not limited to the hybridoma technique originally described by Köhler et al., *Nature,* 256: 495-497, 1975), and the more recent human B-cell hybridoma technique (Kosbor et al., *Immunology Today,* 4: 72, 1983) and the EBV-hybridoma technique (Cole et al., *Monoclonal Antibodies and Cancer Therapy*, Alan R Liss, Inc., pp. 77-96, 1985, all specifically incorporated herein by reference). Antibodies against VEGF-D also may be produced in bacteria from cloned immunoglobulin cDNAs. With the use of the recombinant phage antibody system it may be possible to quickly produce and select antibodies in bacterial cultures and to genetically manipulate their structure. Preparation of anti-VEGF-D monoclonal antibodies is exemplified in U.S. Pat. No. 6,383,484.

When the hybridoma technique is employed, myeloma cell lines may be used. Such cell lines suited for use in hybridoma-producing fusion procedures preferably are non-antibody-producing, have high fusion efficiency, and exhibit enzyme deficiencies that render them incapable of growing in certain selective media which support the growth of only the desired fused cells (hybridomas). For example, where the immunized animal is a mouse, one may use P3-X63/Ag8, P3-X63-Ag8.653, NS1/1.Ag 4 1, Sp210-Ag14, FO, NSO/U, MPC-11, MPC11-X45-GTG 1.7 and S194/5XX0 Bul; for rats, one may use R210.RCY3, Y3-Ag 1.2.3, IR983F and 4B210; and U-266, GM1500-GRG2, LICR-LON-HMy2 and UC729-6 all may be useful in connection with cell fusions.

In addition to the production of monoclonal antibodies, techniques developed for the production of "chimeric antibodies," the splicing of mouse antibody genes to human antibody genes to obtain a molecule with appropriate antigen specificity and biological activity, can be used (Morrison et al., *Proc Natl Acad Sci* 81: 6851-6855, 1984; Neuberger et al., *Nature* 312: 604-608, 1984; Takeda et al., *Nature* 314: 452-454; 1985). Alternatively, techniques described for the production of single-chain antibodies (U.S. Pat. No. 4,946,778) can be adapted to produce VEGF-D-specific single chain antibodies.

Antibody fragments that contain the idiotype of the molecule may be generated by known techniques. For example, such fragments include, but are not limited to, the $F(ab')_2$ fragment which may be produced by pepsin digestion of the antibody molecule; the Fab' fragments which may be generated by reducing the disulfide bridges of the $F(ab')_2$ fragment, and the two Fab' fragments which may be generated by treating the antibody molecule with papain and a reducing agent.

Non-human antibodies may be humanized by any methods known in the art. A preferred chimeric or humanized antibody has a human constant region, while the variable region, or at least a CDR, of the antibody is derived from a non-human species. Methods for humanizing non-human antibodies are well known in the art. (see U.S. Pat. Nos. 5,585,089, and 5,693,762). Generally, a humanized antibody has one or more amino acid residues introduced into its framework region from a source which is non-human. Humanization can be performed, for example, using methods described in Jones et al. (*Nature* 321: 522-525, 1986), Riechmann et al., (*Nature*, 332: 323-327, 1988) and Verhoeyen et al. (*Science* 239:1534-1536, 1988), by substituting at least a portion of a rodent complementarity-determining region (CDRs) for the corresponding regions of a human antibody. Numerous techniques for preparing engineered antibodies are described, e.g., in Owens and Young, *J. Immunol. Meth.*, 168:149-165 (1994). Further changes can then be introduced into the antibody framework to modulate affinity or immunogenicity.

Likewise, using techniques known in the art to isolate CDRs, compositions comprising CDRs are generated. Complementarity determining regions are characterized by six polypeptide loops, three loops for each of the heavy or light chain variable regions. The amino acid position in a CDR is defined by Kabat et al., "Sequences of Proteins of Immunological Interest," U.S. Department of Health and Human Services, (1983), which is incorporated herein by reference. For example, hypervariable regions of human antibodies are roughly defined to be found at residues 28 to 35, from 49-59 and from residues 92-103 of the heavy and light chain variable regions [Janeway and Travers, *Immunobiology*, $2^{nd}$ Edition, Garland Publishing, New York, (1996)]. The murine CDR also are found at approximately these amino acid residues. It is understood in the art that CDR regions may be found within several amino acids of these approximated residues set forth above. An immunoglobulin variable region also consists of four "framework" regions surrounding the CDRs (FR1-4). The sequences of the framework regions of different light or heavy chains are highly conserved within a species, and are also conserved between human and murine sequences.

Compositions comprising one, two, and/or three CDRs of a heavy chain variable region or a light chain variable region of a monoclonal antibody are generated. For example, using the VEGF-D specific monoclonal antibody secreted by hybridoma 4A5, polypeptide compositions comprising 4A5-isolated CDRs are generated. Polypeptide compositions comprising one, two, three, four, five and/or six complementarity determining regions of a monoclonal antibody secreted by hybridoma 4A5 are also contemplated. Using the conserved framework sequences surrounding the CDRs, PCR primers complementary to these consensus sequences are generated to amplify the 4A5 CDR sequence located between the primer regions. Techniques for cloning and expressing nucleotide and polypeptide sequences are well-established in the art [see e.g. Sambrook et al., *Molecular Cloning: A Laboratory Manual*, $2^{nd}$ Edition, Cold Spring Harbor, N.Y. (1989)]. The amplified CDR sequences are ligated into an appropriate plasmid. The plasmid comprising one, two, three, four, five and/or six cloned CDRs optionally contains additional polypeptide encoding regions linked to the CDR.

It is contemplated that modified polypeptide compositions comprising one, two, three, four, five, and/or six CDRs of a monoclonal antibody of a heavy or light chain secreted by hybridoma 4A5 are generated, wherein a CDR is altered to provide increased specificity or affinity to the VEGF-D molecule. Sites at locations in the 4A5 monoclonal antibody CDRs are typically modified in series, e.g., by substituting first with conservative choices (e.g., hydrophobic amino acid substituted for a non-identical hydrophobic amino acid) and then with more dissimilar choices (e.g., hydrophobic amino acid substituted for a charged amino acid), and then deletions or insertions may be made at the target site.

Framework regions (FR) of a murine antibody are humanized by substituting compatible human framework regions chosen from a large database of human antibody variable sequences, including over twelve hundred human $V_H$ sequences and over one thousand $V_L$ sequences. The database of antibody sequences used for comparison is downloaded from Andrew C. R. Martin's KabatMan web page worldwide web at rubic.rdg.ac.uk/abs/The Kabat method for identifying CDR provides a means for delineating the approximate CDR and framework regions from any human antibody and comparing the sequence of a murine antibody for similarity to determine the CDRs and FRs. Best matched human $V_H$ and $V_L$ sequences are chosen on the basis of high overall framework matching, similar CDR length, and minimal mismatching of canonical and $V_H/V_L$ contact residues. Human framework regions most similar to the murine sequence are inserted between the murine CDR. Alternatively, the murine framework region may be modified by making amino acid substitutions of all or part of the native framework region that more closely resemble a framework region of a human antibody.

"Conservative" amino acid substitutions are made on the basis of similarity in polarity, charge, solubility, hydrophobicity, hydrophilicity, and/or the amphipathic nature of the residues involved. For example, nonpolar (hydrophobic) amino acids include alanine (Ala, A), leucine (Leu, L), isoleucine (Ile, I), valine (Val, V), proline (Pro, P), phenylalanine (Phe, F), tryptophan (Trp, W), and methionine (Met, M); polar neutral amino acids include glycine (Gly, G), serine (Ser, S), threonine (Thr, T), cysteine (Cys, C), tyrosine (Tyr, Y), asparagine (Asn, N), and glutamine (Gln, Q); positively charged (basic) amino acids include arginine (Arg, R), lysine (Lys, K), and histidine (His, H); and negatively charged (acidic) amino acids include aspartic acid (Asp, D) and glutamic acid (Glu, E). "Insertions" or "deletions" are preferably in the range of about 1 to 20 amino acids, more preferably 1 to 10 amino acids. The variation may be introduced by systematically making substitutions of amino acids in a polypeptide molecule using recombinant DNA techniques and assaying the resulting recombinant variants for activity. Nucleic acid alterations can be made at sites that differ in the nucleic acids from different species (variable positions) or in highly conserved regions (constant regions). Methods for expressing polypeptide compositions useful in the invention are described in greater detail below.

Recombinant antibody fragments, e.g., scFvs, can also be engineered to assemble into stable multimeric oligomers of high binding avidity and specificity to different target antigens. Such diabodies (dimers), triabodies (trimers) or tetrabodies (tetramers) are well known in the art, see e.g., Kortt et al., *Biomol Eng.* 2001 18:95-108, (2001) and Todorovska et al., *J Immunol Methods.* 248:47-66, (2001).

Derivatives

As stated above, derivative refers to polypeptides chemically modified by such techniques as ubiquitination, labeling (e.g., with radionuclides or various enzymes), covalent polymer attachment such as pegylation (derivatization with polyethylene glycol) and insertion or substitution by chemical synthesis of amino acids such as ornithine. Derivatives of the humanized anti-VEGF-D antibody are also useful as therapeutic agents and may be produced by the method of the invention.

The detectable moiety can be incorporated in or attached to a primer or probe either covalently, or through ionic, van der Waals or hydrogen bonds, e.g., incorporation of radioactive nucleotides, or biotinylated nucleotides that are recognized by streptavadin. The detectable moiety may be directly or indirectly detectable. Indirect detection can involve the binding of a second directly or indirectly detectable moiety to the detectable moiety. For example, the detectable moiety can be the ligand of a binding partner, such as biotin, which is a binding partner for streptavadin, or a nucleotide sequence, which is the binding partner for a complementary sequence, to which it can specifically hybridize. The binding partner may itself be directly detectable, for example, an antibody may be itself labeled with a fluorescent molecule. The binding partner also may be indirectly detectable, for example, a nucleic acid having a complementary nucleotide sequence can be a part of a branched DNA molecule that is in turn detectable through hybridization with other labeled nucleic acid molecules. (See, e.g., P D. Fahrlander and A. Klausner, *Bio/Technology* 6:1165, 1988). Quantitation of the signal is achieved by, e.g., scintillation counting, densitometry, or flow cytometry.

Polyethylene glycol (PEG) may be attached to the chimeric or humanized anti-VEGF-D antibody to provide a longer half-life in vivo. The PEG group may be of any convenient molecular weight and may be linear or branched. The average molecular weight of the PEG will preferably range from about 2 kiloDalton ("kD") to about 100 kDa, more preferably from about 5 kDa to about 50 kDa, most preferably from about 5 kDa to about 10 kDa. The PEG groups will generally be attached to the compounds of the invention via acylation or reductive alkylation through a reactive group on the PEG moiety (e.g., an aldehyde, amino, thiol, or ester group) to a reactive group on the inventive compound (e.g., an aldehyde, amino, or ester group). Addition of PEG moieties to polypeptide of interest can be carried out using techniques well-known in the art. See, e.g., International Publication No. WO 96/11953 and U.S. Pat. No. 4,179,337.

Ligation of the enzyme polypeptide with PEG usually takes place in aqueous phase and can be easily monitored by reverse phase analytical HPLC. The PEGylated peptides can be easily purified by preparative HPLC and characterized by analytical HPLC, amino acid analysis and laser desorption mass spectrometry.

Labels

In some embodiments, the chimeric or humanized anti-VEGF-D antibody is labeled to facilitate its detection. A "label" or a "detectable moiety" is a composition detectable by spectroscopic, photochemical, biochemical, immunochemical, chemical, or other physical means. For example, labels suitable for use in the present invention include, radioactive labels (e.g., $^{32}P$), fluorophores (e.g., fluorescein), electron-dense reagents, enzymes (e.g., as commonly used in an ELISA), biotin, digoxigenin, or haptens as well as proteins which can be made detectable, e.g., by incorporating a radiolabel into the hapten or peptide, or used to detect antibodies specifically reactive with the hapten or peptide.

Examples of labels suitable for use in the present invention include, but are not limited to, fluorescent dyes (e.g., fluorescein isothiocyanate, Texas red, rhodamine, and the like), radiolabels (e.g., $^3H$, $^{125}I$, $^{35}S$, $^{14}C$, or $^{32}P$), enzymes (e.g., horse radish peroxidase, alkaline phosphatase and others commonly used in an ELISA), and colorimetric labels such as colloidal gold, colored glass or plastic beads (e.g., polystyrene, polypropylene, latex, etc.).

The label may be coupled directly or indirectly to the desired component of the assay according to methods well known in the art. Preferably, the label in one embodiment is covalently bound to the biopolymer using an isocyanate reagent for conjugation of an active agent according to the invention. In one aspect of the invention, the bifunctional isocyanate reagents of the invention can be used to conjugate a label to a biopolymer to form a label biopolymer conjugate without an active agent attached thereto. The label biopolymer conjugate may be used as an intermediate for the synthesis of a labeled conjugate according to the invention or may be used to detect the biopolymer conjugate. As indicated above, a wide variety of labels can be used, with the choice of label depending on sensitivity required, ease of conjugation with the desired component of the assay, stability requirements, available instrumentation, and disposal provisions. Non-radioactive labels are often attached by indirect means. Generally, a ligand molecule (e.g., biotin) is covalently bound to the molecule. The ligand then binds to another molecules (e.g., streptavidin) molecule, which is either inherently detectable or covalently bound to a signal system, such as a detectable enzyme, a fluorescent compound, or a chemiluminescent compound.

The compounds of the invention can also be conjugated directly to signal-generating compounds, e.g., by conjugation with an enzyme or fluorophore. Enzymes suitable for use as labels include, but are not limited to, hydrolases, particularly phosphatases, esterases and glycosidases, or oxidotases, particularly peroxidases. Fluorescent compounds, i.e., fluorophores, suitable for use as labels include, but are not limited to, fluorescein and its derivatives, rhodamine and its derivatives, dansyl, umbelliferone, etc. Further examples of suitable fluorophores include, but are not limited to, eosin, TRITC-amine, quinine, fluorescein W, acridine yellow, lissamine rhodamine, B sulfonyl chloride erythroscein, ruthenium (tris, bipyridinium), Texas Red, nicotinamide adenine dinucleotide, flavin adenine dinucleotide, etc. Chemiluminescent compounds suitable for use as labels include, but are not limited to, luciferin and 2,3-dihydrophthalazinediones, e.g., luminol. For a review of various labeling or signal producing systems that can be used in the methods of the present invention, see U.S. Pat. No. 4,391,904.

Means for detecting labels are well known to those of skill in the art. Thus, for example, where the label is radioactive, means for detection include a scintillation counter or photographic film, as in autoradiography. Where the label is a fluorescent label, it may be detected by exciting the fluorochrome with the appropriate wavelength of light and detecting the resulting fluorescence. The fluorescence may be detected visually, by the use of electronic detectors such as charge coupled devices (CCDs) or photomultipliers and the like. Similarly, enzymatic labels may be detected by providing the appropriate substrates for the enzyme and detecting the resulting reaction product. Colorimetric or chemiluminescent labels may be detected simply by observing the color associated with the label. Other labeling and detection systems suitable for use in the methods of the present invention will be readily apparent to those of skill in the art. Such labeled modulators and ligands can be used in the diagnosis of a disease or health condition.

Expression Vectors Comprising Polynucleotides of the Invention

A polynucleotide according to the invention can be joined to any of a variety of other nucleotide sequences by well-established recombinant DNA techniques (see Sambrook et al., (2d Ed.; 1989) Molecular Cloning: A Laboratory Manual, Cold Spring Harbor Laboratory, Cold Spring Harbor, N.Y.). Useful nucleotide sequences for joining to polypeptides include an assortment of vectors, e.g., plasmids, cosmids, lambda phage derivatives, phagemids, and the like, that are well known in the art. Accordingly, the invention also provides a vector including a polynucleotide of the invention and a host cell containing the polynucleotide. In general, the vector contains an origin of replication functional in at least one organism, convenient restriction endonuclease sites, and a selectable marker for the host cell. Vectors according to the invention include expression vectors, replication vectors, probe generation vectors, sequencing vectors, and retroviral vectors. A host cell according to the invention can be a prokaryotic or eukaryotic cell and can be a unicellular organism or part of a multicellular organism. Large numbers of suitable vectors and promoters are known to those of skill in the art and are commercially available for generating the recombinant constructs of the present invention.

A variety of expression vector/host systems may be utilized to contain and express the coding sequence. These include, but are not limited to, microorganisms such as bacteria transformed with recombinant bacteriophage, plasmid, phagemid, or cosmid DNA expression vectors; yeast transformed with yeast expression vectors; insect cell systems infected with viral expression vectors (e.g., baculovirus); plant cell systems transfected with virus expression vectors (e.g., Cauliflower Mosaic Virus, CaMV; Tobacco Mosaic Virus, TMV) or transformed with bacterial expression vectors (e.g., Ti or pBR322 plasmid); or even animal cell systems. Mammalian cells that are useful in recombinant protein productions include, but are not limited to, VERO cells, HeLa cells, Chinese hamster ovary (CHO) cells, COS cells (such as COS-7), WI38, BHK, HepG2, 3T3, RIN, MDCK, A549, PC12, K562 and HEK 293 cells.

Variants

Amino acid sequence variants of an antibody substance or polypeptide can be substitutional, insertional or deletion variants. Deletion variants lack one or more residues of the native protein which are not essential for function or immunogenic activity. A common type of deletion variant is one lacking secretory signal sequences or signal sequences directing a protein to bind to a particular part of a cell. Insertional mutants involve the addition of material at a non-terminal point in the polypeptide. This may include the insertion of an immunoreactive epitope or simply a single residue.

Variants may be substantially homologous or substantially identical to the chimeric or humanized anti-VEGF-D antibody described below. Preferred variants are those which are variants of a chimeric or humanized anti-VEGF-D antibody polypeptide which retain at least some of the biological activity, e.g. VEGF-D binding activity, of the chimeric or humanized anti-VEGF-D antibody.

Substitutional variants typically exchange one amino acid of the wild-type for another at one or more sites within the protein, and may be designed to modulate one or more properties of the polypeptide, such as stability against proteolytic cleavage, without the loss of other functions or properties. Substitutions of this kind preferably are conservative, that is, one amino acid is replaced with one of similar shape and charge, as described above.

Polynucleotide variants and antibody fragments may be readily generated by a worker of skill to encode biologically active fragments, variants, or mutants of the naturally occurring antibody molecule that possess the same or similar biological activity to the naturally occurring antibody. This may be done by PCR techniques, cutting and digestion of DNA encoding the antibody heavy and light chain regions, and the like. For example, point mutagenesis, using PCR and other techniques well-known in the art, may be employed to identify with particularity which amino acid residues are important in particular activities associated with antibody activity. Thus, one of skill in the art will be able to generate single base changes in the DNA strand to result in an altered codon and a missense mutation.

Two manners for defining genera of polypeptide variants include percent amino acid identity to the amino acid sequence of a preferred polypeptide (e.g., 80, 85, 90, 91, 92, 93, 94, 95, 96, 97, 98, or 99% identity preferred), or the ability of encoding-polynucleotides to hybridize to each other under specified conditions. One exemplary set of conditions is as follows: hybridization at 42° C. in 50% formamide, 5×SSC, 20 mM $Na.PO_4$, pH 6.8; and washing in 1×SSC at 55° C. for 30 minutes. Formula for calculating equivalent hybridization conditions and/or selecting other conditions to achieve a desired level of stringency are well known. It is understood in the art that conditions of equivalent stringency can be achieved through variation of temperature and buffer, or salt concentration as described Ausubel, et al. (Eds.), Protocols in Molecular Biology, John Wiley & Sons (1994), pp. 6.0.3 to 6.4.10. Modifications in hybridization conditions can be empirically determined or precisely calculated based on the length and the percentage of guanosine/cytosine (GC) base pairing of the probe. The hybridization conditions can be calculated as described in Sambrook, et al., (Eds.), Molecular Cloning: A Laboratory Manual, Cold Spring Harbor Laboratory Press: Cold Spring Harbor, N.Y. (1989), pp. 9.47 to 9.51.

One aspect of the present invention contemplates generating glycosylation site mutants in which the O- or N-linked glycosylation site of the chimeric or humanized anti-VEGF-D antibody has been mutated. Such mutants will yield important information pertaining to the biological activity, physical structure and substrate binding potential of the chimeric or humanized anti-VEGF-D antibody. In particular aspects it is contemplated that other mutants of the chimeric or humanized anti-VEGF-D antibody polypeptide may be generated that retain the biological activity but have increased or decreased binding activity. As such, mutations of the antigen-binding site are particularly contemplated in order to generate protein variants with altered binding activity.

In order to construct mutants such as those described above, one of skill in the art may employ well known standard technologies. Specifically contemplated are N-terminal deletions, C-terminal deletions, internal deletions, as well as random and point mutagenesis.

N-terminal and C-terminal deletions are forms of deletion mutagenesis that take advantage for example, of the presence of a suitable single restriction site near the end of the C- or N-terminal region. The DNA is cleaved at the site and the cut ends are degraded by nucleases such as BAL31, exonuclease III, DNase I, and S1 nuclease. Rejoining the two ends produces a series of DNAs with deletions of varying size around the restriction site. Proteins expressed from such mutant can be assayed for appropriate biological function, e.g. enzymatic activity, using techniques standard in the art, and described in the specification. Similar techniques may be employed for internal deletion mutants by using two suitably placed restriction sites, thereby allowing a precisely defined deletion to be made, and the ends to be religated as above.

Also contemplated are partial digestion mutants. In such instances, one of skill in the art would employ a "frequent cutter", that cuts the DNA in numerous places depending on the length of reaction time. Thus, by varying the reaction conditions it will be possible to generate a series of mutants of varying size, which may then be screened for activity.

A random insertional mutation may also be performed by cutting the DNA sequence with a DNase I, for example, and inserting a stretch of nucleotides that encode, 3, 6, 9, 12 etc., amino acids and religating the end. Once such a mutation is made the mutants can be screened for various activities presented by the wild-type protein.

The amino acids of a particular protein can be altered to create an equivalent, or even an improved, second-generation molecule. Such alterations contemplate substitution of a given amino acid of the protein without appreciable loss of interactive binding capacity with structures such as, for example, antigen-binding regions of antibodies or binding sites on substrate molecules or receptors. Since it is the interactive capacity and nature of a protein that defines that protein's biological functional activity, certain amino acid substitutions can be made in a protein sequence, and its underlying DNA coding sequence, and nevertheless obtain a protein with like properties. Thus, various changes can be made in the DNA sequences of genes without appreciable loss of their biological utility or activity, as discussed below.

In making such changes, the hydropathic index of amino acids may be considered. It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of their hydrophobicity and charge characteristics (Kyte & Doolittle, *J. Mol. Biol.*, 157(1):105-132, 1982, incorporated herein by reference). Generally, amino acids may be substituted by other amino acids that have a similar hydropathic index or score and still result in a protein with similar biological activity, i.e., still obtain a biological functionally equivalent protein.

In addition, the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As such, an amino acid can be substituted for another having a similar hydrophilicity value and still obtain a biologically equivalent and immunologically equivalent protein.

Exemplary amino acid substitutions that may be used in this context of the invention include but are not limited to exchanging arginine and lysine; glutamate and aspartate; serine and threonine; glutamine and asparagine; and valine, leucine and isoleucine. Other such substitutions that take into account the need for retention of some or all of the biological activity whilst altering the secondary structure of the protein will be well known to those of skill in the art.

Formulation of Pharmaceutical Compositions

To administer antibody substances of the invention to human or test animals, it is preferable to formulate the antibody substances in a composition comprising one or more pharmaceutically acceptable carriers. The phrase "pharmaceutically or pharmacologically acceptable" refer to molecular entities and compositions that do not produce allergic, or other adverse reactions when administered using routes well-known in the art, as described below. "Pharmaceutically acceptable carriers" include any and all clinically useful solvents, dispersion media, coatings, antibacterial and antifungal agents, isotonic and absorption delaying agents and the like.

Pharmaceutical carriers include pharmaceutically acceptable salts, particularly where a basic or acidic group is present in a compound. For example, when an acidic substituent, such as —COOH, is present, the ammonium, sodium, potassium, calcium and the like salts, are contemplated for administration. Additionally, where an acid group is present, pharmaceutically acceptable esters of the compound (e.g., methyl, tert-butyl, pivaloyloxymethyl, succinyl, and the like) are contemplated as preferred forms of the compounds, such esters being known in the art for modifying solubility and/or hydrolysis characteristics for use as sustained release or prodrug formulations.

When a basic group (such as amino or a basic heteroaryl radical, such as pyridyl) is present, then an acidic salt, such as hydrochloride, hydrobromide, acetate, maleate, pamoate, phosphate, methanesulfonate, p-toluenesulfonate, and the like, is contemplated as a form for administration.

In addition, compounds may form solvates with water or common organic solvents. Such solvates are contemplated as well.

The chimeric or humanized anti-VEGF-D antibody compositions may be administered orally, topically, transdermally, parenterally, by inhalation spray, vaginally, rectally, or by intracranial injection. The term parenteral as used herein includes subcutaneous injections, intravenous, intramuscular, intracisternal injection, or infusion techniques. Administration by intravenous, intradermal, intramusclar, intramammary, intraperitoneal, intrathecal, retrobulbar, intrapulmonary injection and or surgical implantation at a particular site is contemplated as well. Generally, compositions are essentially free of pyrogens, as well as other impurities that could be harmful to the recipient.

Pharmaceutical compositions of the present invention containing a chimeric or humanized antibody against human VEGF-D as an active ingredient may contain pharmaceutically acceptable carriers or additives depending on the route of administration. Examples of such carriers or additives include water, a pharmaceutical acceptable organic solvent, collagen, polyvinyl alcohol, polyvinylpyrrolidone, a carboxyvinyl polymer, carboxymethylcellulose sodium, polyacrylic sodium, sodium alginate, water-soluble dextran, carboxymethyl starch sodium, pectin, methyl cellulose, ethyl cellulose, xanthan gum, gum Arabic, casein, gelatin, agar, diglycerin, glycerin, propylene glycol, polyethylene glycol, Vaseline, paraffin, stearyl alcohol, stearic acid, human serum albumin (HSA), mannitol, sorbitol, lactose, a pharmaceutically acceptable surfactant and the like. Additives used are chosen from, but not limited to, the above or combinations thereof, as appropriate, depending on the dosage form of the present invention.

Formulation of the pharmaceutical composition will vary according to the route of administration selected (e.g., solution, emulsion). An appropriate composition comprising the chimeric or humanized antibody to be administered can be prepared in a physiologically acceptable vehicle or carrier. For solutions or emulsions, suitable carriers include, for example, aqueous or alcoholic/aqueous solutions, emulsions or suspensions, including saline and buffered media. Parenteral vehicles can include sodium chloride solution, Ringer's dextrose, dextrose and sodium chloride, lactated Ringer's or fixed oils. Intravenous vehicles can include various additives, preservatives, or fluid, nutrient or electrolyte replenishers.

A variety of aqueous carriers, e.g., water, buffered water, 0.4% saline, 0.3% glycine, or aqueous suspensions may contain the active compound in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyl-eneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

The antibodies of this invention can be lyophilized for storage and reconstituted in a suitable carrier prior to use. This technique has been shown to be effective with conventional immunoglobulins. Any suitable lyophilization and reconstitution techniques can be employed. It will be appreciated by those skilled in the art that lyophilization and reconstitution can lead to varying degrees of antibody activity loss and that use levels may have to be adjusted to compensate.

Dispersible powders and granules suitable for preparation of an aqueous suspension by the addition of water provide the active compound in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The concentration of antibody in these formulations can vary widely, for example from less than about 0.5%, usually at or at least about 1% to as much as 15 or 20% by weight and will be selected primarily based on fluid volumes, viscosities, etc., in accordance with the particular mode of administration selected. Thus, a typical pharmaceutical composition for parenteral injection could be made up to contain 1 ml sterile buffered water, and 50 mg of antibody. A typical composition for intravenous infusion could be made up to contain 250 ml of sterile Ringer's solution, and 150 mg of antibody. Actual methods for preparing parenterally administrable compositions will be known or apparent to those skilled in the art and are described in more detail in, for example, Remington's Pharmaceutical Science, 15th ed., Mack Publishing Company, Easton, Pa. (1980). An effective dosage of chimeric or humanized anti-VEGF-D antibody is within the range of 0.01 mg to 1000 mg per kg of body weight per administration.

The pharmaceutical compositions may be in the form of a sterile injectable aqueous, oleaginous suspension, dispersions or sterile powders for the extemporaneous preparation of sterile injectable solutions or dispersions. The suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. The carrier can be a solvent or dispersion medium containing, for example, water, ethanol, polyol (for example, glycerol, propylene glycol, and liquid polyethylene glycol, and the like), suitable mixtures thereof, vegetable oils, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

In all cases the form must be sterile and must be fluid to the extent that easy syringability exists. The proper fluidity can be maintained, for example, by the use of a coating, such as lecithin, by the maintenance of the required particle size in the case of dispersion and by the use of surfactants. It must be stable under the conditions of manufacture and storage and must be preserved against the contaminating action of microorganisms, such as bacteria and fungi. The prevention of the action of microorganisms can be brought about by various antibacterial an antifungal agents, for example, parabens, chlorobutanol, phenol, sorbic acid, thimerosal, and the like. In many cases, it will be desirable to include isotonic agents, for example, sugars or sodium chloride. Prolonged absorption of the injectable compositions can be brought about by the use in the compositions of agents delaying absorption, for example, aluminum monostearate and gelatin.

Compositions useful for administration may be formulated with uptake or absorption enhancers to increase their efficacy. Such enhancer include for example, salicylate, glycocholate/linoleate, glycholate, aprotinin, bacitracin, SDS, caprate and the like. See, e.g., Fix (*J. Pharm. Sci.,* 85:1282-1285, 1996) and Oliyai and Stella (*Ann. Rev. Pharmacol. Toxicol.,* 32:521-544, 1993).

Chimeric or humanized anti-VEGF-D antibody compositions contemplated for use inhibit cancer growth, including proliferation, invasiveness, and metastasis, thereby rendering them particularly desirable for the treatment of cancer. In particular, the compositions exhibit cancer-inhibitory properties at concentrations that are substantially free of side effects, and are therefore useful for extended treatment protocols. For example, co-administration of a chimeric or humanized anti-VEGF-D antibody composition with another, more toxic, chemotherapeutic agent can achieve beneficial inhibition of a cancer, while effectively reducing the toxic side effects in the patient.

In addition, the properties of hydrophilicity and hydrophobicity of the compositions contemplated for use in the invention are well balanced, thereby enhancing their utility for both in vitro and especially in vivo uses, while other compositions lacking such balance are of substantially less utility. Specifically, compositions contemplated for use in the invention have an appropriate degree of solubility in aqueous media which permits absorption and bioavailability in the body, while also having a degree of solubility in lipids which permits the compounds to traverse the cell membrane to a putative site of action. Thus, chimeric or humanized anti-VEGF-D antibody compositions contemplated are maximally effective when they can be delivered to the site of the tumor and permeate the tumor cell milieu.

Administration and Dosing

In one aspect, methods of the invention include a step of administration of a pharmaceutical composition.

Methods of the invention are performed using any medically-accepted means for introducing a therapeutic directly or indirectly into a mammalian subject, including but not limited to injections, oral ingestion, intranasal, topical, transdermal, parenteral, inhalation spray, vaginal, or rectal administration. The term parenteral as used herein includes subcutaneous, intravenous, intramuscular, and intracisternal injections, as well as catheter or infusion techniques. Administration by, intradermal, intramammary, intraperitoneal, intrathecal, retrobulbar, intrapulmonary injection and or surgical implantation at a particular site is contemplated as well.

In one embodiment, administration is performed at the site of a cancer or affected tissue needing treatment by direct injection into the site or via a sustained delivery or sustained release mechanism, which can deliver the formulation internally. For example, biodegradable microspheres or capsules or other biodegradable polymer configurations capable of sustained delivery of a composition (e.g., a soluble polypeptide, antibody, or small molecule) can be included in the formulations of the invention implanted near the cancer.

Therapeutic compositions may also be delivered to the patient at multiple sites. The multiple administrations may be rendered simultaneously or may be administered over a period of time. In certain cases it is beneficial to provide a continuous flow of the therapeutic composition. Additional therapy may be administered on a period basis, for example, hourly, daily, weekly or monthly.

Particularly contemplated in the presenting invention is the administration of multiple agents, such as a chimeric or humanized anti-VEGF-D antibody in conjunction with a second agent as described herein. It is contemplated that these agents may be given simultaneously, in the same formulation. It is further contemplated that the agents are administered in a separate formulation and administered concurrently, with concurrently referring to agents given within 30 minutes of each other.

In another aspect, the second agent is administered prior to administration of the chimeric or humanized anti-VEGF-D antibody. Prior administration refers to administration of the second agent within the range of one week prior to treatment with the chimeric or humanized anti-VEGF-D antibody, up to 30 minutes before administration of the chimeric or humanized anti-VEGF-D antibody. It is further contemplated that the second agent is administered subsequent to administration of the chimeric or humanized anti-VEGF-D antibody. Subsequent administration is meant to describe administration from 30 minutes after chimeric or humanized anti-VEGF-D antibody treatment up to one week after chimeric or humanized anti-VEGF-D antibody administration.

It is further contemplated that when chimeric or humanized anti-VEGF-D antibody is administered in combination with a second agent, wherein the second agent is a cytokine or growth factor, a chemotherapeutic agent, the administration also includes use of a radiotherapeutic agent or radiation therapy. The radiation therapy administered in combination with a chimeric or humanized anti-VEGF-D antibody composition is administered as determined by the treating physician, and at doses typically given to patients being treated for cancer.

The amounts of chimeric or humanized anti-VEGF-D antibody in a given dosage will vary according to the size of the individual to whom the therapy is being administered as well as the characteristics of the disorder being treated. In exemplary treatments, it may be necessary to administer about 1 mg/day, 5 mg/day, 10 mg/day, 20 mg/day, 50 mg/day, 75 mg/day, 100 mg/day, 150 mg/day, 200 mg/day, 250 mg/day, 500 mg/day or 1000 mg/day. These concentrations may be administered as a single dosage form or as multiple doses. Standard dose-response studies, first in animal models and then in clinical testing, reveal optimal dosages for particular disease states and patient populations.

It will also be apparent that dosing should be modified if traditional therapeutics are administered in combination with therapeutics of the invention.

Kits

As an additional aspect, the invention includes kits which comprise one or more compounds or compositions packaged in a manner which facilitates their use to practice methods of the invention. In one embodiment, such a kit includes a compound or composition described herein (e.g., a composition comprising a chimeric or humanized VEGF-D antibody alone or in combination with a second agent), packaged in a container such as a sealed bottle or vessel, with a label affixed to the container or included in the package that describes use of the compound or composition in practicing the method. Preferably, the compound or composition is packaged in a unit dosage form. The kit may further include a device suitable for administering the composition according to a specific route of administration or for practicing a screening assay. Preferably, the kit contains a label that describes use of the chimeric or humanized VEGF-D antibody composition.

Additional aspects and details of the invention will be apparent from the following examples, which are intended to be illustrative rather than limiting. Example 1 describes the cloning of murine heavy chain and light chain regions of a VEGF-D specific monoclonal antibody. Example 2 describes the construction of human IgG1 expression vectors. Example 3 describes expression of a chimeric antibody and initial characterization of binding activity. Example 4 describes the purification of the antibody from 293 cells and the interaction of the chimeric antibody with VEGF-D. Example 5 discloses that the chimeric antibody blocked the interaction of VEGF-D with its receptors, VEGFR-2 and VEGFR-3. Example 6 describes the use of chimeric or humanized VEGF-D antibody to regulate VEGF-D related biological functions. Example 7 describes use of chimeric or humanized VEGF-D antibody in angiogenesis and lymphangiogenesis assays. Example 8 describes use of a chimeric or humanized VEGF-D antibody in in vivo tumor models. Example 9 describes administration of chimeric or humanized anti-VEGF-D antibody compositions to cancer patients.

Example 1

Cloning of Murine/Human Heavy and Light V-Region Genes

The following procedures pertain to construction of a chimeric antibody wherein variable regions from a mouse anti-VEGF-D antibody are assembled into human constant region to create a chimeric, humanized antibody.

The monoclonal antibody used for generating a chimeric antibody was the mouse anti-VEGF-D antibody produced by the hybridoma VD1/4A5 [deposited in the American Type Culture Collection, 10801 University Boulevard, Manassas, Va. 20110-2209, on Apr. 16, 1999 (ATCC No. HB-12698]. The deposit was made under the requirements of the Budapest Treaty on the International Recognition of the Deposit of Microorganisms for the Purposes of Patent Procedure. Production of the VD1/4A5 antibody is described in U.S. Pat. No. 6,383,484 (Achen et al.), incorporated herein by reference.

In order to begin constructing a chimeric VEGF-D antibody, it was first necessary to clone and sequence the light chain and heavy chain variable region genes from a hybridoma cell line which produces VEGF-D specific monoclonal antibody. Total RNA from VD1/4A5 or "4A5" hybridoma cells was obtained by standard RNA isolation techniques (Chomczynski & Sacchi, *Anal Biochem* 162: 156-159, 1987). First strand cDNA was prepared using the first strand cDNA synthesis kit (Pharmacia Biotech) and priming with d(T) 18 for both the heavy chain and light chain (Renner et al., *Biotechniques* 24:720-2, 1998).

The hybridoma cDNA was subjected to PCR using combinations of primers for antibody heavy and light chains. The nucleotide sequences of the murine/human 5' primers for the heavy and light chains are shown in Tables 2 and 3, respectively. The 3' primers are shown in Table 4. The light chain primer hybridized within the kappa constant region close to the V-C junction. The heavy chain 3' primer hybridised within the CH-1 constant region of heavy close to the V-CH1 junction.

TABLE 2

Oligonucleotide primers for the 5' region of Mouse Heavy Variable (MHV) domains.

| | | |
|---|---|---|
| MHV-1: | 5'ATGAAATGCAGCTGGGTCATSTTCTTC3' | (SEQ ID NO: 10) |
| MHV-2: | 5'ATGGGATGGAGCTRATCATSYTCTT3' | (SEQ ID NO: 11) |
| MHV-3: | 5'ATGAAGWTGTGGTTAAACTGGGFTTTTT3' | (SEQ ID NO: 12) |
| MHV-4: | 5'ATGRACTTTGWYTCAGCTTGRTTT3' | (SEQ ID NO: 13) |
| MHV-5: | 5'ATGGACTCGAGGCTCAAMAGTTTTCCTT3' | (SEQ ID NO: 14) |
| MHV-6: | 5'ATGGCTGTCYTRGSGCTRCTCTTCTGC3' | (SEQ ID NO: 15) |
| MHV-7: | 5'ATGGRATGGAGCKGGRTCTTTMTCTT3' | (SEQ ID NO: 16) |
| MHV-8 | 5'ATGAGAGTGCTGATTCTTTTGTG3' | (SEQ ID NO: 17) |
| MHV-9: | 5'ATGGMTTGGGTGTGGAMCTTGCTATTCCTG3' | (SEQ ID NO: 18) |
| MHV-10: | 5'ATGGGCAGACTTACATTCTCATTCCTG3' | (SEQ ID NO: 19) |
| MHV-11: | 5'ATGGATTTTGGGCTGATTTTTTTATTG3' | (SEQ ID NO: 20) |
| MHV-12: | 5'ATGATGGTGTTAAGTCTTCTGTACCTG3' | (SEQ ID NO: 21) |

KEY R = A/G,
Y = T/C,
W = A/T,
K = T/G,
M = A/C,
S = C/G.

TABLE 3

Oligonucleotide primers for the 5' region of Mouse Kappa Variable (MKV) domains.

| | | |
|---|---|---|
| MKV-1: | 5'ATGAAGTTGCCTGTTAGGCTGTTGGTGCTG3' | (SEQ ID NO: 22) |
| MKV-2: | 5'ATGGAGWCAGACACACTCCTGYTATGGGT3' | (SEQ ID NO: 23) |
| MKV-3: | 5'ATGAGTGTGCTCACTCAGGTCCTGGSGTTG3' | (SEQ ID NO: 24) |
| MKV-4: | 5'ATGAGGRCCCCTGCTCAGWTTYTTGGM-WTCTTG3' | (SEQ ID NO: 25) |
| MKV-5: | 5'ATGGATTTWCAGGTGCAGATTWTCAGCTTC3' | (SEQ ID NO: 26) |
| MKV-6: | 5'ATGAGGTKCYYTGYTSAGYTYCTGRGG3' | (SEQ ID NO: 27) |
| MKV-7: | 5'ATGGGCWTCAAGATGGAGTCACAKWYYCWGG3' | (SEQ ID NO: 28) |
| MKV-8: | 5'ATGTGGGGAYCTKTTTYCMMTTTTTCAATTG3' | (SEQ ID NO: 29) |

TABLE 3-continued

Oligonucleotide primers for the 5' region of
Mouse Kappa Variable (MKV)
domains.

| | | |
|---|---|---|
| MKV-9: | 5'ATGGTRTCCWCASCTCAGTTCCTTG3' | (SEQ ID NO: 30) |
| MKV-10: | 5'ATGTATATATGTTTGTTGTCTATTTCT3' | (SEQ ID NO: 31) |
| MKV-11: | 5'ATGGAAGCCCCAGCTCAGCTTCTCTTCC3' | (SEQ ID NO: 32) |
| MKV-12: | 5'ATGAAGTTTCCTTCTCAACTTCTGCTC3' | (SEQ ID NO: 33) |

KEY R = A/G,
Y = T/C,
W = A/T,
K = T/G,
M = A/C,
S = C/G.

TABLE 4

Oligonucleotide primers for the 3' ends of
mouse VH and VL genes.

| | |
|---|---|
| Light chain (MKC):<br>5'TGGATGGTGGGAAGATG3' | (SEQ ID NO: 34) |
| Heavy chain (MHC):<br>5'CCAGTGGATAGACAGATG3 | (SEQ ID NO: 35) |

The overall strategy was to amplify DNA fragments encoding the variable domains of the 4A5 monoclonal antibody and insert them into the pEAK8 vector.

PCR products for $V_H$ and $V_L$ chains of monoclonal antibody 4A5 obtained as described above were cloned using the TA Cloning System (Invitrogen Corporation, Leiden, The Netherlands). Pseudogenes for heavy chain and light chain were amplified and were eliminated by sequence analysis. A novel immunoglobulin-coding sequence was determined in each case, for both heavy chain and light chain, respectively.

Example 2

Construction of Human IgG1 VEGF-D Expression Vectors

Next, an expression vector comprising the mouse anti-VEGF-D antibody variable regions and human immunoglobulin constant region was assembled.

PCR was used to modify the ends of the anti-VEGF-D light chain (SEQ ID NO: 36 and 37) and heavy chain (SEQ ID NO: 38 and 39) sequences listed in FIGS. 1A and 1B. The PCR primers used to modify the 5' and 3' sequences flanking the cDNA sequences are set out in Table 5. The 5' end of the cDNA flanking sequences were modified by adding a HindIII restriction site followed by a standard Kozak sequence (GCCGCCACC, SEQ ID NO: 40), (Kozak, *Nucleic Acids Res* 15: 8125-48, 1987). All cDNA sequences was modified at the 3' end to include a splice donor site and an intron after the last amino acid of the variable domain. A BamHI restriction site was included in the intron for insertion into the expression vector. Thus, each heavy and light chain construct comprised a HindIII restriction site followed by a Kozak sequence, followed by a start codon, followed by the natural leader sequence, followed by the variable antibody cDNA. The 3' was inserted via BamHI restriction site that was removed after splicing.

TABLE 5

Oligonucleotide primers for the modification of
murine variable domains for
Chimeric anti-VEGF-D Antibody

| | | |
|---|---|---|
| VEGF HC 5'Nco | CGGGCCATGGCGGAAGTGAAGCTGGTGGAGTCTG | (SEQ ID NO: 41) |
| VEGF HG 3'BamHI | CAGAGGATCCACTCACCTGAAGAGACGGTGACCAGAGTCCC | (SEQ ID NO: 42) |
| VEGF LC 5'Nco | CGGGCCATGGACATTGTGATGACCCAGTCTCAA | (SEQ ID NO: 43) |
| VEGF LC 3'BamHI | GATGGATCCACTCACGTTTTACTTCCAACTTTGTCCCCGA | (SEQ ID NO: 44) |

Example 3

Chimeric Antibody Expression and Initial Characterization of Binding Activity

The chimeric anti-VEGF-D antibody construct was expressed by transient gene expression in HEK293 cells according to the method published by Meissner and colleagues (Meissner et al., *Biotechnol Bioeng.* 75:197-203, 2001).

Modified HEK 293-EBNA cells (Meissner et al., supra) were cultured in Ex-Cell V Pro media (Lexena, USA). Transfection of suspension adapted HEK293-EBNA cells was carried out in DMEM/F12 medium supplemented with 29 mM sodium bicarbonate, 10 mM HEPES, 2.5 mg/L human transferrin, 2.5 mg/L insulin, 0.1 mM diethanolamine, 0.1 mM L-proline, and 1% FCS (hereafter DMEM-based medium). Prior to transfection, cells were expanded in 0.5 L spinner flasks in 293G medium (Bio-Whittaker, Walkersville, Md., USA) supplemented with 1% FCS. For transfection, cells were centrifuged in 250 ml bottles for 5 minutes at 400 g and 200 ml spinner flasks were inoculated with 1×10$^6$ cells/ml freshly resuspended in 50 ml of DMEM-based medium containing 1% FCS. Cells were maintained in this medium at 37° C. for 2 hours. 1 mg of supercoiled plasmid DNA was precipitated in a 100 µl/ml transfection mix consisting of 2.5 ml of 250 mM CaCl$_2$ and 2.5 ml of 1.4 mM phosphate in 50 mM HEPES+280 mM NaCl that had been combined and mixed rapidly. After an incubation period at room temperature of exactly 1 minute the precipitation mix was added rapidly to the cell suspension.

In order to measure the assembly of the chimeric IgG 1/Kappa antibody in vitro, antibody expression was measured in HEK 293 cell supernatants. HEK 293 cells were co-transfected with the vectors coding for both the chimeric anti-VEGF-D light chain region (FIG. 2, SEQ ID NO: 45) and chimeric anti-VEGF-D heavy chain region (FIG. 3, SEQ ID NO: 46) of the individual antibody as described. After 3-4 days cell culture supernatants were tested for IgG1 antibody production by Dot Blot (BioRad, Munich, Germany). VEGF-D was bound to nitrocellulose membrane using protocol provided by the apparatus manufacturer. Wells were blocked with 1% BSA in tris-buffered saline (TBS) and washed in 0.05% Tween 20 in TBS (TTBS). The chimeric antibody (100 microliters of HEK cell culture supernatant) is then suspended in 1% BSA in TTBS and placed in well. Secondary antibody against IgG1 labelled with horseradish peroxidase (HRP) is then added to the well to detect the chimeric VEGF-D antibody. VEGF-D binding was detected using ECL. Dot blot analysis demonstrated that the chimeric antibody effectively binds to VEGF-D.

Integrity of antibodies secreted into the supernatant were analyzed by SDS Page analysis and Western blot in reducing and non-reducing conditions (Renner et al., *Eur J Immunol* 25:2027-2033, 1995). The antibody revealed the expected size for heavy (~55 kD) and light chain (~25 kD) constructs.

Example 4

Purification of Antibody from 293 Cells and Interaction of Chimeric Antibody with VEGF-D The chimeric antibody produced as described above was purified using protein A sepharose (Pharmacia Biotech), and the ability of the antibody to bind VEGF-D was monitored by immunoprecipitation and Western blotting.

Cell culture medium containing the mature human VEGF-D (VEGF-DΔNΔC) was incubated with the chimeric antibody coupled to protein A sepharose. As control, the same volume of supernatant was incubated with the same amount of a mouse monoclonal antibody to the receptor for granulocyte colony stimulating factor (LMM774 antibody) (Layton, et al., *Growth Factors* 14:117-130, 1997), coupled to protein A sepharose. After 1.5 hours incubation at 4° C., material bound to the sepharose was collected by centrifugation and subjected to SDS-polyacrylamide gel electrophoresis followed by Western blotting with a biotinylated polyclonal antiserum that binds the mature form of VEGF-D (R&D Systems, Minneapolis, Minn.) and detection using chemiluminescence (Pierce).

The chimeric VEGF-D antibody precipitated the mature VEGF-D (~21 kDa), but VEGF-D was not precipitated by the control antibody, demonstrating that the chimeric antibody specifically binds human VEGF-D.

Example 5

Chimeric Antibody Blocked Interaction of VEGF-D with its Receptors, VEGFR-2 and VEGFR-3

The chimeric antibody was tested for the ability to block the binding of human VEGF-DΔNΔC to its receptors, VEGFR-2 and VEGFR-3, using receptor binding and cross-linking bioassays.

These bioassays involve the use of Ba/F3 pre-B cells which have been transfected with plasmid constructs encoding chimeric receptors consisting of the extracellular domain of VEGFR-2 or VEGFR-3 fused to the cytoplasmic domain of the erythropoietin (EPO) receptor (Stacker, et al., *J. Biol. Chem.* 274:34884-34892, 1999; Achen, et al., *Eur. J. Biochem.* 267:2505-2515, 2000). These cells are routinely passaged in interleukin-3 (IL-3) and will die in the absence of IL-3. However, if signaling is induced from the cytoplasmic domain of the chimeric receptors, these cells survive and proliferate in the absence of IL-3. Such signaling is induced by ligands which bind and cross-link the VEGFR-2 or VEGFR-3 extracellular domains of the chimeric receptors. Therefore, binding of VEGF-DΔNΔC to the VEGFR-2 or VEGFR-3 extracellular domains causes the cells to survive and proliferate in the absence of IL-3. However, addition of substances which block the binding of VEGF-D to the receptors will cause cell death in the absence of IL-3. An alternative Ba/F3 cell line which expresses a chimeric receptor containing the extracellular domain of the Tie2 receptor, which does not bind VEGF family members, is not induced by VEGF-D to proliferate and is used, in the presence of IL-3, as a control to test for non-specific effects of potential inhibitors.

Samples of purified VEGF-DΔNΔC were incubated with varying amounts of the chimeric antibody for one hour at 4° C. in PBS before dilution of the mixtures 1:10 with IL-3-deficient cell culture medium (DMEM with 10% fetal bovine serum (FBS), 50 mM L-glutamine, 50 µg/ml gentamicin, and 1 mg/ml G418). The resulting media contained approximately 1 µg/ml of VEGF-DΔNΔC and varying concentrations of the antibody. The VEGF-2 or VEGFR-3 Ba/F3 cell lines were then incubated in the media for 48 hours at 37° C. DNA synthesis was then quantitated by the addition of 1 µCi of $^3$H-thymidine and further incubation for 4 hours prior to harvesting. Incorporated $^3$H-thymidine was measured using a cell harvester (Tomtec®) and beta counting. The effect of the chimeric antibody on the proliferative responses of the cell lines to VEGF-DΔNΔC was calculated as the mean of two experiments, with error to denote the variation from the mean.

Figure 5:
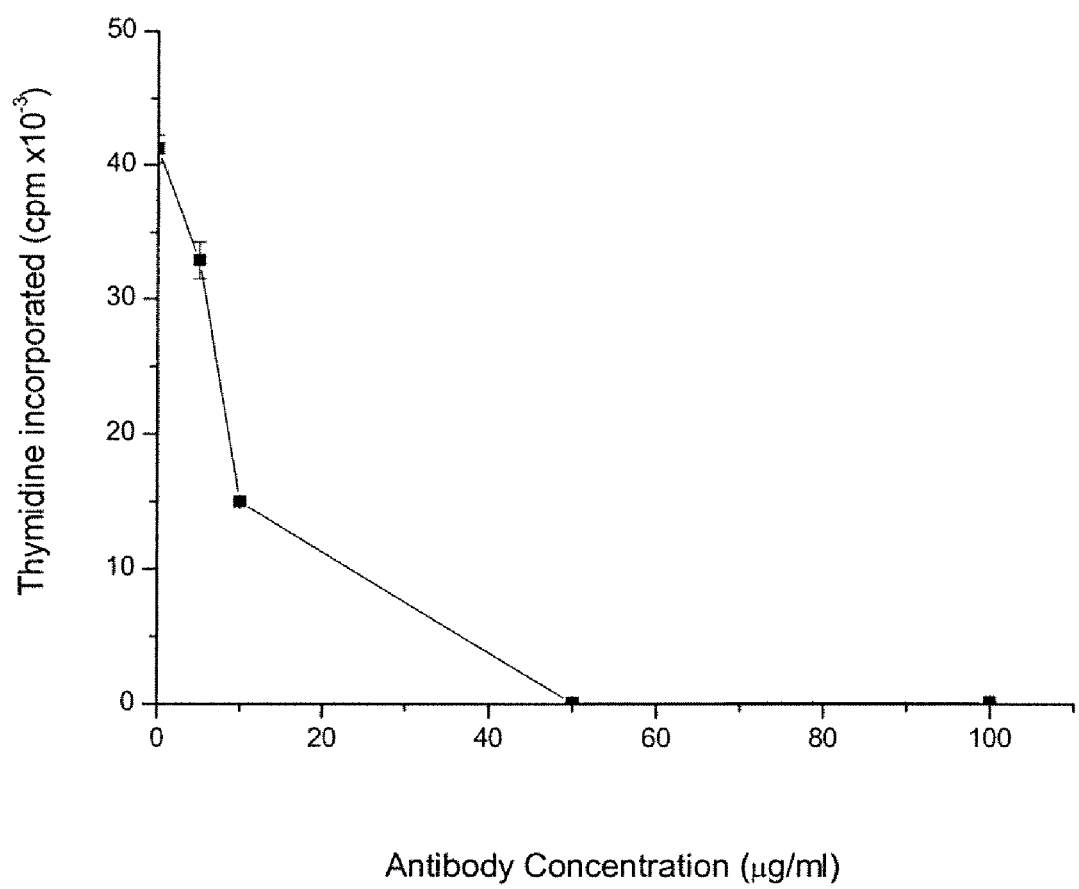
FIG. 5 is a graph depicting the cell growth (measured by Thymidine incorporation) in response to VEGF-D mixed with varying concentrations of a chimeric anti-VEGF-D antibody of VEGFR-3 transfected cells.

The chimeric antibody blocked the response of both VEGFR-2 and VEGFR-3 expressing cell lines to VEGF-DΔNΔC in a dose-dependent fashion. Inclusion of antibody at 50 µg/ml in the cell culture medium was sufficient to totally block the response of the cell lines of both the VEGFR expressing Ba/F3 cells (FIG. 4 and FIG. 5). In contrast, the antibody did not inhibit the survival and proliferation of the control Tie2 cell line in the presence of IL-3, indicating that it did not exert non-specific cytotoxic effects.

These data demonstrated that the chimeric antibody blocks the binding and cross-linking of VEGFR-2 and VEGFR-3 by VEGF-D at the cell surface. Thus, the chimeric anti-VEGF-D antibody provides a useful therapeutic to block angiogenic or lymphangiogenic signals through the VEGFR-2 and VEGFR-3 receptors thereby reducing tumor cell growth and metastasis.

Example 6

Effects of Chimeric or Humanized VEGF-D Antibody on VEGF-D Mediated Biological Functions VEGF-D is involved with many functions of angiogenesis, lymphangiogenesis and endothelial cell growth. The influence of chimeric or humanized VEGF-D antibody on such VEGF-D functions is investigated using the following assays:

A. Cell Migration Assay

For example, human microvascular endothelial cells (HMVEC) express VEGFR-3, and such cells can be used to investigate the effect of chimeric or humanized anti-VEGF-D antibody on such cells. Since VEGF/VEGFR interactions are thought to play a role in migration of cells, a cell migration assay using HMVEC or other suitable cells can be used to demonstrate stimulatory or inhibitory effects of chimeric or humanized anti-VEGF-D antibody molecules.

Using a modified Boyden chamber assay, polycarbonate filter wells (Transwell, Costar, 8 micrometer pore) are coated with 50 µg/ml fibronectin (Sigma), 0.1% gelatin in PBS for 30 minutes at room temperature, followed by equilibration into DMEM/0.1% BSA at 37° C. for 1 hour. HMVEC (passage 4-9, $1\times10^5$ cells) naturally expressing VEGFR-3 receptors or endothelial cell lines recombinantly expressing VEGFR-3 and/or VEGFR-2 are plated in the upper chamber of the filter well and allowed to migrate to the undersides of the filters, toward the bottom chamber of the well, which contains serum-free media supplemented with either pro-VEGF-D, enzymatically processed VEGF-D, or recombinant mature VEGF-D in the presence of varying concentrations of chimeric or humanized anti-VEGF-D antibody. After 5 hours, cells adhering to the top of the transwell are removed with a cotton swab, and the cells that migrate to the underside of the filter are fixed and stained. For quantification of cell numbers, 6 randomly selected 400× microscope fields are counted per filter.

In another variation, the migration assay described above is carried out using porcine aortic endothelial cells (PAEC) stably transfected with constructs such as those described previously, to express VEGFR-2, VEGFR-3, or both VEGFR-2 and VEGFR-3 (i.e. PAE/VEGFR-2, PAE/VEGFR-3, or PAE/VEGFR-2/VEGFR-3). PAEC are transfected using the method described in Soker et al. (*Cell* 92:735-745. 1998). Transfected PAEC ($1.5\times10^4$ cells in serum free F12 media supplemented with 0.1% BSA) are plated in the upper wells of a Boyden chamber prepared with fibronectin as described above. Increasing concentrations of either pro-VEGF-D or fully processed VEGF-D are added to the wells of the lower chamber to induce migration of the endothelial cells. After 4 hours, the number of cells migrating through the filter is quantitated by phase microscopy.

An inhibition of VEGF-D mediated cell migration as a result of addition of the chimeric or humanized anti-VEGF-D antibody indicates that the antibody is a useful tool for inhibiting lymphangiogenesis and angiogenesis at the site of tumor or other aberrant lymph migration.

Example 7

Assay of VEGF-D Blockade in Angiogenesis and Lymphangiogenesis

There continues to be a long-felt need for additional agents that inhibit angiogenesis (e.g., to inhibit growth of tumors). Moreover, various angiogenesis inhibitors may work in concert through the same or different receptors, and on different portions of the circulatory system (e.g., arteries or veins or capillaries; vascular or lymphatic). Angiogenesis assays are employed to measure the effects of chimeric or humanized anti-VEGF-D antibody on angiogenic processes, alone or in combination with other angiogenic and anti-angiogenic factors to determine preferred combination therapy involving chimeric or humanized anti-VEGF-D antibody and other modulators. Exemplary procedures include the following.

A. In Vitro Assays for Angiogenesis

1. Sprouting Assay

HMVEC cells (passage 5-9) are grown to confluency on collagen coated beads (Pharmacia) for 5-7 days. The beads are plated in a gel matrix containing 5.5 mg/ml fibronectin (Sigma), 2 units/ml thrombin (Sigma), DMEM/2% fetal bovine serum (FBS) and the following test and control proteins: 20 ng/ml VEGF, 20 ng/ml VEGF-C, 20 ng/ml VEGF-D, or growth factors plus chimeric or humanized anti-VEGF-D antibody, and several combinations of other angiogenic and anti-angiogenic factors. Serum free media supplemented with test and control proteins is added to the gel matrix every 2 days and the number of endothelial cell sprouts exceeding bead length are counted and evaluated.

2. Migration Assay

The transwell migration assay previously described may also be used in conjunction with the sprouting assay to determine the effects the chimeric or humanized anti-VEGF-D antibody of the invention have on the interactions of VEGF-D activators and cellular function. The effects of VEGF-D on cellular migration are assayed in response the chimeric or humanized anti-VEGF-D antibody, or in combination with known angiogenic or anti-angiogenic agents. A decrease in cellular migration due to the presence of chimeric or humanized anti-VEGF-D antibody after VEGF-D stimulation indicates that the invention provides a method for inhibiting angiogenesis.

This assay may also be carried out with cells that naturally express either VEGFR-3 or VEGFR-2, e.g. bovine endothelial cells which preferentially express VEGFR-2. Use of naturally occurring or transiently expressing cells displaying a specific receptor may determine that the chimeric or humanized anti-VEGF-D antibody of the invention may be used to preferentially treat diseases involving aberrant activity of either VEGFR-3 or VEGFR-2.

B. In vivo assays for angiogenesis and lymphangiogenesis.

1. Chorioallantoic Membrane (CAM) Assay

Three-day old fertilized white Leghorn eggs are cracked, and chicken embryos with intact yolks are carefully placed in 20×100 mm plastic Petri dishes. After six days of incubation in 3% $CO_2$ at 37° C., a disk of methylcellulose containing VEGF-D, and various combinations of the chimeric or humanized anti-VEGF-D antibody, and soluble VEGFR-2 or VEGFR-3 complexes, dried on a nylon mesh (3×3 mm) is implanted on the CAM of individual embryos, to determine the influence of chimeric or humanized anti-VEGF-D antibody on vascular development and potential uses thereof to promote or inhibit vascular formation. The nylon mesh disks are made by desiccation of 10 µl of 0.45% methylcellulose (in $H_2O$). After 4-5 days of incubation, embryos and CAMs are examined for the formation of new blood vessels and lymphatic vessels in the field of the implanted disks by a stereoscope. Disks of methylcellulose containing PBS are used as negative controls. Antibodies that recognize both blood and lymphatic vessel cell surface molecules are used to further characterize the vessels.

2. Corneal Assay

Corneal micropockets are created with a modified von Graefe cataract knife in both eyes of male 5- to 6-week-old C57BL6/J mice. A micropellet (0.35×0.35 mm) of sucrose aluminum sulfate (Bukh Meditec, Copenhagen, Denmark) coated with hydron polymer type NCC (IFN Science, New Brunswick, N.J.) containing various concentrations of VEGF molecules (especially VEGF-D) alone or in combination with: i) factors known to modulate vessel growth (e.g., 160 ng of VEGF, or 80 ng of FGF-2); or ii) chimeric or humanized anti-VEGF-D antibody. The pellet is positioned 0.6-0.8 mm from the limbus. After implantation, erythromycin/ophthamic ointment is applied to the eyes. Eyes are examined by a slit-lamp biomicroscope over a course of 3-12 days. Vessel length and clock-hours of circumferential neovascularization and lymphangiogenesis are measured. Furthermore, eyes are cut into sections and are immunostained for blood vessel and/or lymphatic markers (LYVE-1 [Prevo et al., *J. Biol. Chem.*, 276:19420-19430, 2001)], podoplanin [Breiteneder-Geleff et al., *Am. J. Pathol.*, 154:385-94, 1999).] and VEGFR-3) to further characterize affected vessels.

Example 8

In Vivo Tumor Models

Molecules of VEGF-family proteins are often correlative with vascular density in and around tumors and tumor progression. There is a need in the art to develop newer, more effective therapeutics that are specific for the offending agent, rather than being non-specific. One molecule that could potentially knock out lymphangiogenesis and angiogenesis in tumors would be especially therapeutic. Chimeric or humanized anti-VEGF-D antibodies are first tested in the following experimental models to determine their efficacy for administration to human patients suffering from cancer.

A. Ectopic Tumor Implantation

Six- to 8-week-old nude (nu/nu) mice (SLC, Shizuoka, Japan) undergo subcutaneous transplantation of C6 rat glioblastoma cells or PC-3 prostate cancer cells in 0.1 mL phosphate-buffered saline (PBS) on the right flank. The chimeric or humanized anti-VEGF-D antibody outlined previously are administered to the animals at various concentrations and dosing regimens. Tumor size is measured in 2 dimensions, and tumor volume is calculated using the formula, width2× length/2. After 14 days, the mice are humanely killed and autopsied to evaluate the quantity and physiology of tumor vasculature in response to VEGF-D inhibition by chimeric or humanized anti-VEGF-D antibodies.

It will be apparent that the assay can also be performed using other tumor cell lines implanted in nude mice or other mouse strains. Use of wild type mice implanted with LLC lung cancer cells and B16 melanoma cells is specifically contemplated.

B. Lymphatic Metastasis Model

VEGF-D/VEGFR-3 interactions are often associated in adult tissue with the organization and growth of lymphatic vessels. The following protocol indicates the ability of chimeric or humanized anti-VEGF-D antibody, or fragments thereof to inhibit lymphatic metastasis.

MDA-MB-435 breast cancer cells are injected bilaterally into the second mammary fat pads of athymic, female, eight week old nude mice. The cells often metastasize to lymph node by 12 weeks. Initially, the role of chimeric or humanized anti-VEGF-D antibody binding to VEGF-D in tumor metastasis is assessed using assays of VEGFR-3/VEGF-D binding described previously. A decrease in metastasis correlating with administration of the chimeric or humanized anti-VEGF-D antibody indicates that blockade of VEGF-D activity is important in tumor metastasis. Moreover, the chimeric or humanized anti-VEGF-D antibody polypeptides are administered in combination with other materials for reducing tumor metastasis. See, e.g., Intl. Patent Publ. No. WO 00/21560, incorporated herein by reference in its entirety. Mice are sacrificed after 12 weeks and lymph nodes are investigated by histologic analysis. Decrease in lymphatic vessels and tumor spread as a result of administration of the chimeric or humanized anti-VEGF-D antibody indicate the invention may be an effective therapeutic compound in the prevention of tumor metastasis.

Example 9

Administration of Chimeric or Humanized Anti-VEGF-D Antibody Compositions to Cancer Patients Administration of chimeric or humanized anti-VEGF-D antibody in animal models of tumor metastasis provides the basis for administering cancer patients chimeric or humanized anti-VEGF-D antibody alone or in combination with cytokines or growth factors, or chemotherapeutic or radiotherapeutic agents. Humanized or chimeric anti-VEGF-D antibody is administered using regimens similar to those described for administration of the anti-VEGF antibody (Cobleigh et al., *Semin. Oncol.* 30 (Suppl 16): 117-24, 2003; Yang et al., *New Engl. J. Med.* 349:4278-34, 2003)

Humanized or chimeric anti-VEGF-D antibody is administered to patients within a dose range of 3 mg/kg to 20 mg/kg per treatment. It is recognized by one of skill in the art that the amount of dose will vary from patient to patient, and may be anywhere from 1 mg/kg/day to 100 mg/kg/day. Humanized or chimeric anti-VEGF-D antibody is administered in doses appropriate for the patient's size, sex, and weight, as would be known or readily determined in the art. Subsequent doses of the chimeric or humanized anti-VEGF-D antibody may be increased or decreased to address the particular patient's response to therapy.

Chimeric or humanized anti-VEGF-D antibody is given in any formulation recognized in the art to allow the composition to diffuse into the bloodstream or tissue sites, e.g. aqueous solution or oily suspension. Chimeric or humanized anti-VEGF-D antibody is administered at a frequency and dose determined by the treating physician. For example, anti-VEGF-D antibody may be administered once daily for 7 days, twice daily for 7 days, every other day for 14 days, continuously for 14 days, 1 time/week, 1 time every other week, or any other regimen the physician prescribes. Humanized or chimeric anti-VEGF-D antibody may be administered continuously, e.g., through intravenous delivery or by slow release methods, for an extended period of time. The administration may last 1-24 hours, or longer and is amenable to optimization using routine experimentation. The anti-VEGF-D antibody may also be given for a duration not requiring extended treatment. Additionally, anti-VEGF-D antibody composition may be administered daily, weekly, bi-weekly, or at other effective frequencies, as would be determinable by one of ordinary skill in the art.

It is contemplated that anti-VEGF-D antibody is administered to patients in combination with other therapeutics, such as with other chemotherapeutic or radiotherapeutic agents, or with growth factors or cytokines. When given in combination with another agent, the amount of anti-VEGF-D antibody given may be reduced accordingly. Second agents are administered in an amount determined to be safe and effective at ameliorating human disease.

It is contemplated that cytokines or growth factors, and chemotherapeutic agents or radiotherapeutic agents are administered in the same formulation as chimeric or humanized anti-VEGF-D antibody and given simultaneously. Alternatively, the agents may also be administered in a separate formulation and still be administered concurrently with chimeric or humanized anti-VEGF-D antibody. As used herein, concurrently refers to agents given within 30 minutes of each other. The second agent may also be administered prior to administration of chimeric or humanized anti-VEGF-D antibody. Prior administration refers to administration of the agent within the range of one week prior to anti-VEGF-D antibody treatment up to 30 minutes before administration of anti-VEGF-D antibody. It is further contemplated that the second agent is administered subsequent to administration of anti-VEGF-D antibody. Subsequent administration is meant to describe administration from 30 minutes after anti-VEGF-D antibody treatment up to one week after anti-VEGF-D antibody administration. Chimeric or humanized anti-VEGF-D antibody compositions may also be administered in conjunction with a regimen of radiation therapy as prescribed by a treating physician.

In one approach, the effectiveness of chimeric or humanized anti-VEGF-D antibody treatment is determined by computer tomographic (CT) scans of the tumor area with the degree of tumor regression assessed by measuring the decrease in tumor size. Biopsies or blood samples are also used to assess the presence or absence and metastasizing ability of particular cell types in response to treatment with chimeric or humanized anti-VEGF-D antibody alone, or in combination with other chemotherapeutic agents. These response assessments are made periodically during the course of treatment to monitor the response of a patient to a given therapy.

A decrease in tumor size, reduction of tumor metastasis and improvement in patient prognosis after treatment with chimeric or humanized anti-VEGF-D antibody alone or in combination with a cytokine or growth factor, a chemotherapeutic agent or a radiotherapeutic agent indicates that the method effectively treats patients exhibiting solid tumor and/or tumors capable of tumor metastasis.

Numerous modifications and variations in the invention as set forth in the above illustrative examples are expected to occur to those skilled in the art. Consequently only such limitations as appear in the appended claims should be placed on the invention.

The invention claimed is:

1. A method for inhibiting Vascular Endothelial Growth Factor-D (VEGF-D) mediated cell growth, migration, or differentiation, comprising administering to a human subject an antibody that specifically binds VEGF-D, wherein the antibody is administered in an amount effective to inhibit VEGF-D interaction with VEGFR-2 or VEGFR-3, and wherein the antibody comprises a light chain variable region comprising a polypeptide comprising the amino acid sequence of SEQ ID NO: 37;

a heavy chain variable region comprising a polypeptide comprising the amino acid sequence of SEQ ID NO: 39;

a human antibody light chain constant region; and a human antibody heavy chain constant region.

2. A method for inhibiting Vascular Endothelial Growth Factor-D (VEGF-D) mediated cell growth, migration, or differentiation, comprising administering to a human subject a chimeric or humanized antibody that specifically binds VEGF-D, wherein the antibody is administered in an amount effective to inhibit VEGF-D interaction with VEGFR-2 or VEGFR-3, and wherein the chimeric or humanized antibody comprises heavy chain complementarity determining regions from a mouse antibody and framework regions from non-murine source, wherein the heavy chain variable region (VH) comprises complementarity determining regions (CDR) with the amino acid sequences: H-CDR1 set forth in SEQ ID NO: 50, H-CDR2 set forth in SEQ ID NO: 51, and H-CDR3 set forth in SEQ ID NO: 52;

light chain complementarity determining regions from a mouse antibody and framework regions from non-murine source, wherein the light chain variable region (VL) comprises complementarity determining regions (CDR) with the amino acid sequences L-CDR1 set forth in SEQ ID NO: 47, L-CDR2 set forth in SEQ ID NO: 48, and L-CDR3: set forth in SEQ ID NO: 49;

a human antibody light chain constant region; and a human antibody heavy chain constant region.

3. The method according to claim 2, wherein the framework regions of the heavy chain variable region and the framework regions of the light chain variable region comprise human framework regions.

4. A method for inhibiting Vascular Endothelial Growth Factor-D (VEGF-D) mediated cell growth, migration, or differentiation, comprising administering to a human subject a chimeric or humanized antibody that specifically binds VEGF-D, wherein the antibody is administered in an amount effective to inhibit VEGF-D interaction with VEGFR-2 or VEGFR-3, and wherein the chimeric or humanized antibody comprises complementarity determining regions (CDR) of non-human origin from SEQ ID NOS: 37 and 39 and constant regions of light and heavy chains, said constant region being of human origin, wherein the biological function of specific binding to said VEGF-D is preserved.

* * * * *

SEQUENCE LISTING

```
<160> NUMBER OF SEQ ID NOS: 52

<210> SEQ ID NO 1
<211> LENGTH: 2076
<212> TYPE: DNA
<213> ORGANISM: Homo sapiens

<400> SEQUENCE: 1
cggggaaggg gagggaggag ggggacgagg gctctggcgg gtttggaggg gctgaacatc      60
gcggggtgtt ctggtgtccc ccgccccgcc tctccaaaaa gctacaccga cgcggaccgc     120
ggcggcgtcc tccctcgccc tcgcttcacc tcgcgggctc cgaatgcggg gagctcggat     180
gtccggtttc ctgtgaggct tttacctgac acccgccgcc tttccccggc actggctggg     240
agggcgccct gcaaagttgg gaacgcggag ccccggaccc gctcccgccg cctccggctc     300
gcccaggggg ggtcgccggg aggagcccgg gggagaggga ccaggagggg cccgcggcct     360 cgcagggggcg cccgcgcccc caccccctgcc cccgccagcg gaccggtccc ccaccccgg    420 tccttccacc atgcacttgc tgggcttctt ctctgtggcg tgttctctgc tcgccgctgc     480
gctgctcccg ggtcctcgcg aggcgcccgc cgccgccgcc gccttcgagt ccggactcga     540
cctctcggac gcggagcccg acgcgggcga ggccacggct tatgcaagca aagatctgga     600
ggagcagtta cggtctgtgt ccagtgtaga tgaactcatg actgtactct acccagaata     660
ttggaaaatg tacaagtgtc agctaaggaa aggaggctgg caacataaca gagaacaggc     720
caacctcaac tcaaggacag aagagactat aaaatttgct gcagcacatt ataatacaga     780
gatcttgaaa agtattgata atgagtggag aaagactcaa tgcatgccac gggaggtgtg     840
tatagatgtg gggaaggagt ttggagtcgc gacaaacacc ttctttaaac ctccatgtgt     900
gtccgtctac agatgtgggg gttgctgcaa tagtgagggg ctgcagtgca tgaacaccag     960
cacgagctac ctcagcaaga cgttatttga aattacagtg cctctctctc aaggccccaa    1020
accagtaaca atcagttttg ccaatcacac ttcctgccga tgcatgtcta aactggatgt    1080
```

```
ttacagacaa gttcattcca ttattagacg ttccctgcca gcaacactac cacagtgtca    1140
ggcagcgaac aagacctgcc ccaccaatta catgtggaat aatcacatct gcagatgcct    1200
ggctcaggaa gattttatgt tttcctcgga tgctggagat gactcaacag atggattcca    1260
tgacatctgt ggaccaaaca aggagctgga tgaagagacc tgtcagtgtg tctgcagagc    1320
ggggcttcgg cctgccagct gtggacccca caagaacta gacagaaact catgccagtg    1380
tgtctgtaaa acaaactct tccccagcca atgtggggcc aaccgagaat tgatgaaaa     1440 cacatgccag tgtgtatgta aagaacctg ccccagaaat caaccctaa atcctggaaa     1500 atgtgcctgt gaatgtacag aaagtccaca gaaatgcttg ttaaaaggaa agaagttcca    1560
ccaccaaaca tgcagctgtt acagacggcc atgtacgaac cgccagaagg cttgtgagcc    1620
aggattttca tatagtgaag aagtgtgtcg ttgtgtccct tcatattgga aaagaccaca    1680
aatgagctaa gattgtactg ttttccagtt catcgattt ctattatgga aaactgtgtt     1740
gccacagtag aactgtctgt gaacagagag acccttgtgg gtccatgcta acaaagacaa    1800
aagtctgtct ttcctgaacc atgtggataa ctttacagaa atggactgga gctcatctgc    1860
aaaaggcctc ttgtaaagac tggttttctg ccaatgacca aacagccaag attttcctct    1920
tgtgatttct ttaaaagaat gactatataa tttatttcca ctaaaaatat tgtttctgca    1980 ttcatttta tagcaacaac aattggtaaa actcactgtg atcaatattt ttatatcatg      2040
caaaatatgt ttaaaataaa atgaaaattg tattat                              2076

<210> SEQ ID NO 2
<211> LENGTH: 419
<212> TYPE: PRT
<213> ORGANISM: Homo sapiens

<400> SEQUENCE: 2

Met His Leu Leu Gly Phe Phe Ser Val Ala Cys Ser Leu Leu Ala Ala
1               5                   10                  15

Ala Leu Leu Pro Gly Pro Arg Glu Ala Pro Ala Ala Ala Ala Ala Phe
            20                  25                  30

Glu Ser Gly Leu Asp Leu Ser Asp Ala Glu Pro Asp Ala Gly Glu Ala
        35                  40                  45

Thr Ala Tyr Ala Ser Lys Asp Leu Glu Glu Gln Leu Arg Ser Val Ser
    50                  55                  60

Ser Val Asp Glu Leu Met Thr Val Leu Tyr Pro Glu Tyr Trp Lys Met
65                  70                  75                  80

Tyr Lys Cys Gln Leu Arg Lys Gly Gly Trp Gln His Asn Arg Glu Gln
                85                  90                  95

Ala Asn Leu Asn Ser Arg Thr Glu Glu Thr Ile Lys Phe Ala Ala Ala
            100                 105                 110

His Tyr Asn Thr Glu Ile Leu Lys Ser Ile Asp Asn Glu Trp Arg Lys
        115                 120                 125

Thr Gln Cys Met Pro Arg Glu Val Cys Ile Asp Val Gly Lys Glu Phe
    130                 135                 140

Gly Val Ala Thr Asn Thr Phe Phe Lys Pro Pro Cys Val Ser Val Tyr
145                 150                 155                 160

Arg Cys Gly Gly Cys Cys Asn Ser Glu Gly Leu Gln Cys Met Asn Thr
                165                 170                 175

Ser Thr Ser Tyr Leu Ser Lys Thr Leu Phe Glu Ile Thr Val Pro Leu
            180                 185                 190
```

```
Ser Gln Gly Pro Lys Pro Val Thr Ile Ser Phe Ala Asn His Thr Ser
        195                 200                 205

Cys Arg Cys Met Ser Lys Leu Asp Val Tyr Arg Gln Val His Ser Ile
        210                 215                 220

Ile Arg Arg Ser Leu Pro Ala Thr Leu Pro Gln Cys Gln Ala Ala Asn
225                 230                 235                 240

Lys Thr Cys Pro Thr Asn Tyr Met Trp Asn Asn His Ile Cys Arg Cys
                245                 250                 255

Leu Ala Gln Glu Asp Phe Met Phe Ser Ser Asp Ala Gly Asp Asp Ser
            260                 265                 270

Thr Asp Gly Phe His Asp Ile Cys Gly Pro Asn Lys Glu Leu Asp Glu
        275                 280                 285

Glu Thr Cys Gln Cys Val Cys Arg Ala Gly Leu Arg Pro Ala Ser Cys
    290                 295                 300

Gly Pro His Lys Glu Leu Asp Arg Asn Ser Cys Gln Cys Val Cys Lys
305                 310                 315                 320

Asn Lys Leu Phe Pro Ser Gln Cys Gly Ala Asn Arg Glu Phe Asp Glu
                325                 330                 335

Asn Thr Cys Gln Cys Val Cys Lys Arg Thr Cys Pro Arg Asn Gln Pro
            340                 345                 350

Leu Asn Pro Gly Lys Cys Ala Cys Glu Cys Thr Glu Ser Pro Gln Lys
        355                 360                 365

Cys Leu Leu Lys Gly Lys Lys Phe His His Gln Thr Cys Ser Cys Tyr
    370                 375                 380

Arg Arg Pro Cys Thr Asn Arg Gln Lys Ala Cys Glu Pro Gly Phe Ser
385                 390                 395                 400

Tyr Ser Glu Glu Val Cys Arg Cys Val Pro Ser Tyr Trp Lys Arg Pro
                405                 410                 415

Gln Met Ser

<210> SEQ ID NO 3
<211> LENGTH: 2128
<212> TYPE: DNA
<213> ORGANISM: Homo sapiens

<400> SEQUENCE: 3
caagacttct ctgcattttc tgccaaaatc tgtgtcagat ttaagacaca tgcttctgca      60
agcttccatg aaggttgtgc aaaaaagttt caatccagag ttgggttcca gctttctgta     120
gctgtaagca ttggtggcca caccacctcc ttacaaagca actagaacct gcggcataca     180
ttggagagat tttttaatt ttctggacat gaagtaaatt tagagtgctt tctaatttca     240
ggtagaagac atgtccacct tctgattatt tttggagaac attttgattt ttttcatctc     300
tctctcccca cccctaagat tgtgcaaaaa aagcgtacct tgcctaattg aaataatttc     360
attggatttt gatcagaact gattatttgg ttttctgtgt gaagttttga ggtttcaaac     420
tttccttctg gagaatgcct tttgaaacaa ttttctctag ctgcctgatg tcaactgctt     480
agtaatcagt ggatattgaa atattcaaaa tgtacagaga gtgggtagtg gtgaatgttt     540
tcatgatgtt gtacgtccag ctggtgcagg ctccagtaa tgaacatgga ccagtgaagc     600
gatcatctca gtccacattg gaacgatctg aacagacagt cagggctgct tctagtttgg     660
aggaactact tcgaattact cactctgagg actggaagct gtggagatgc aggctgaggc     720
tcaaaagttt taccagtatg gactctcgct cagcatccca tcggtccact aggttttgcgg    780 caactttcta tgacattgaa acactaaaag ttatagatga agaatggcaa agaactcagt     840
```

```
gcagccctag agaaacgtgc gtggaggtgg ccagtgagct ggggaagagt accaacacat    900
tcttcaagcc cccttgtgtg aacgtgttcc gatgtggtgg ctgttgcaat gaagagagcc    960
ttatctgtat gaacaccagc acctcgtaca tttccaaaca gctctttgag atatcagtgc   1020
ctttgacatc agtacctgaa ttagtgcctg ttaaagttgc caatcataca ggttgtaagt   1080
gcttgccaac agccccccgc catccatact caattatcag aagatccatc cagatccctg   1140
aagaagatcg ctgttcccat tccaagaaac tctgtcctat tgacatgcta tgggatagca   1200
acaaatgtaa atgtgttttg caggaggaaa atccacttgc tggaacagaa gaccactctc   1260
atctccagga accagctctc tgtgggccac acatgatgtt tgacgaagat cgttgcgagt   1320
gtgtctgtaa acaccatgt cccaaagatc taatccagca ccccaaaaac tgcagttgct   1380
ttgagtgcaa agaaagtctg gagacctgct gccagaagca caagctattt cacccagaca   1440
cctgcagctg tgaggacaga tgcccctttc ataccagacc atgtgcaagt ggcaaaacag   1500
catgtgcaaa gcattgccgc tttccaaagg agaaaagggc tgcccagggg ccccacagcc   1560
gaaagaatcc ttgattcagc gttccaagtt ccccatccct gtcatttta acagcatgct   1620
gctttgccaa gttgctgtca ctgtttttt cccaggtgtt aaaaaaaaaa tccatttac   1680
acagcaccac agtgaatcca gaccaaccttt ccattcacac cagctaagga gtccctggtt   1740
cattgatgga tgtcttctag ctgcagatgc ctctgcgcac caaggaatgg agaggagggg   1800
acccatgtaa tccttttgtt tagttttgtt tttgttttt ggtgaatgag aaaggtgtgc   1860
tggtcatgga atggcaggtg tcatatgact gattactcag agcagatgag gaaaactgta   1920
gtctctgagt cctttgctaa tcgcaactct tgtgaattat tctgattctt ttttatgcag   1980
aatttgattc gtatgatcag tactgacttt ctgattactg tccagcttat agtcttccag   2040
tttaatgaac taccatctga tgtttcatat ttaagtgtat ttaaagaaaa taaacaccat   2100
tattcaagcc aaaaaaaaaa aaaaaaa                                      2128
```

<210> SEQ ID NO 4
<211> LENGTH: 354
<212> TYPE: PRT
<213> ORGANISM: Homo sapiens

<400> SEQUENCE: 4

```
Met Tyr Arg Glu Trp Val Val Asn Val Phe Met Met Leu Tyr Val
1               5                   10                  15

Gln Leu Val Gln Gly Ser Ser Asn Glu His Gly Pro Val Lys Arg Ser
            20                  25                  30

Ser Gln Ser Thr Leu Glu Arg Ser Glu Gln Gln Ile Arg Ala Ala Ser
        35                  40                  45

Ser Leu Glu Glu Leu Leu Arg Ile Thr His Ser Glu Asp Trp Lys Leu
    50                  55                  60

Trp Arg Cys Arg Leu Arg Leu Lys Ser Phe Thr Ser Met Asp Ser Arg
65                  70                  75                  80

Ser Ala Ser His Arg Ser Thr Arg Phe Ala Ala Thr Phe Tyr Asp Ile
                85                  90                  95

Glu Thr Leu Lys Val Ile Asp Glu Glu Trp Gln Arg Thr Gln Cys Ser
            100                 105                 110

Pro Arg Glu Thr Cys Val Glu Val Ala Ser Glu Leu Gly Lys Ser Thr
        115                 120                 125

Asn Thr Phe Phe Lys Pro Cys Val Asn Val Phe Arg Cys Gly Gly
    130                 135                 140
```

```
Cys Cys Asn Glu Glu Ser Leu Ile Cys Met Asn Thr Ser Thr Ser Tyr
145                 150                 155                 160

Ile Ser Lys Gln Leu Phe Glu Ile Ser Val Pro Leu Thr Ser Val Pro
            165                 170                 175

Glu Leu Val Pro Val Lys Val Ala Asn His Thr Gly Cys Lys Cys Leu
            180                 185                 190

Pro Thr Ala Pro Arg His Pro Tyr Ser Ile Ile Arg Arg Ser Ile Gln
            195                 200                 205

Ile Pro Glu Glu Asp Arg Cys Ser His Ser Lys Lys Leu Cys Pro Ile
210                 215                 220

Asp Met Leu Trp Asp Ser Asn Lys Cys Lys Cys Val Leu Gln Glu Glu
225                 230                 235                 240

Asn Pro Leu Ala Gly Thr Glu Asp His Ser His Leu Gln Glu Pro Ala
            245                 250                 255

Leu Cys Gly Pro His Met Met Phe Asp Glu Asp Arg Cys Glu Cys Val
            260                 265                 270

Cys Lys Thr Pro Cys Pro Lys Asp Leu Ile Gln His Pro Lys Asn Cys
            275                 280                 285

Ser Cys Phe Glu Cys Lys Glu Ser Leu Glu Thr Cys Cys Gln Lys His
            290                 295                 300

Lys Leu Phe His Pro Asp Thr Cys Ser Cys Glu Asp Arg Cys Pro Phe
305                 310                 315                 320

His Thr Arg Pro Cys Ala Ser Gly Lys Thr Ala Cys Ala Lys His Cys
                    325                 330                 335

Arg Phe Pro Lys Glu Lys Arg Ala Ala Gln Gly Pro His Ser Arg Lys
            340                 345                 350

Asn Pro

<210> SEQ ID NO 5
<211> LENGTH: 1325
<212> TYPE: DNA
<213> ORGANISM: Mus Musculus

<400> SEQUENCE: 5
ggagaatgcc ttttgcaaca cttttcagta gctgcctgga aacaactgct tagtcatcgg      60
tagacattta aatattcaa aatgtatgga gaatggggaa tggggaatat cctcatgatg      120
ttccatgtgt acttggtgca gggcttcagg agcgaacatg gaccagtgaa ggatttttct      180
tttgagcgat catcccggtc catgttggaa cgatctgaac aacagatccg agcagcttct      240
agtttggagg agttgctgca aatcgcgcac tctgaggact ggaagctgtg gcgatgccgg      300
ttgaagctca aaagtcttgc cagtatggac tcacgctcag catcccatcg ctccaccaga      360
tttgcggcaa ctttctatga cactgaaaca ctaaaagtta tagatgaaga atggcagagg      420
acccaatgca gccctagaga gacatgcgta gaagtcgcca gtgagctggg aagacaacc      480 aacacattct tcaagccccc ctgtgtaaat gtcttccggt gtggaggctg ctgcaacgaa      540
gagggtgtga tgtgtatgaa cacaagcacc tcctacatct ccaaacagct ctttgagata      600
tcagtgcctc tgacatcagt gcccgagtta gtgcctgtta aaattgccaa ccatacgggt      660
tgtaagtgct gcccacgggc ccccgccat ccttactcaa ttatcagaag atccattcag      720
accccagaag aagatgaatg tcctcattcc aagaaactct gtcctattga catgctgtgg      780
gataacacca aatgtaaatg tgttttgcaa gacgagactc cactgcctgg acagaaagac      840
cactcttacc tccaggaacc cactctctgt ggaccgcaca tgacgtttga tgaagatcgc      900
```

```
tgtgagtgcg tctgtaaagc accatgtccg ggagatctca ttcagcaccc ggaaaactgc    960
agttgctttg agtgcaaaga aagtctggag agctgctgcc aaaagcacaa gatttttcac   1020
ccagacacct gcagctgtga ggacagatgt ccttttcaca ccagaacatg tgcaagtaga   1080
aagccagcct gtggaaagca ctggcgcttt ccaaaggaga caagggccca gggactctac   1140
agccaggaga acccttgatt caacttcctt tcaagtcccc ccatctctgt cattttaaac   1200
agctcactgc tttgtcaagt tgctgtcact gttgcccact acccttgaa catgtgcaaa    1260 cacagacaca cacacacaca cacacagaga gcaactagaa ttatgttttc taggtgctgc   1320
ctaag                                                              1325
```

<210> SEQ ID NO 6
<211> LENGTH: 358
<212> TYPE: PRT
<213> ORGANISM: Mus musculus

<400> SEQUENCE: 6

```
Met Tyr Gly Glu Trp Gly Met Gly Asn Ile Leu Met Met Phe His Val
1               5                   10                  15

Tyr Leu Val Gln Gly Phe Arg Ser Glu His Gly Pro Val Lys Asp Phe
            20                  25                  30

Ser Phe Glu Arg Ser Ser Arg Ser Met Leu Glu Arg Ser Glu Gln Gln
        35                  40                  45

Ile Arg Ala Ala Ser Ser Leu Glu Glu Leu Leu Gln Ile Ala His Ser
    50                  55                  60

Glu Asp Trp Lys Leu Trp Arg Cys Arg Leu Lys Leu Lys Ser Leu Ala
65                  70                  75                  80

Ser Met Asp Ser Arg Ser Ala Ser His Arg Ser Thr Arg Phe Ala Ala
                85                  90                  95

Thr Phe Tyr Asp Thr Glu Thr Leu Lys Val Ile Asp Glu Glu Trp Gln
            100                 105                 110

Arg Thr Gln Cys Ser Pro Arg Glu Thr Cys Val Glu Val Ala Ser Glu
        115                 120                 125

Leu Gly Lys Thr Thr Asn Thr Phe Phe Lys Pro Pro Cys Val Asn Val
    130                 135                 140

Phe Arg Cys Gly Gly Cys Cys Asn Glu Glu Gly Val Met Cys Met Asn
145                 150                 155                 160

Thr Ser Thr Ser Tyr Ile Ser Lys Gln Leu Phe Glu Ile Ser Val Pro
                165                 170                 175

Leu Thr Ser Val Pro Glu Leu Val Pro Val Lys Ile Ala Asn His Thr
            180                 185                 190

Gly Cys Lys Cys Leu Pro Thr Gly Pro Arg His Pro Tyr Ser Ile Ile
        195                 200                 205

Arg Arg Ser Ile Gln Thr Pro Glu Glu Asp Cys Pro His Ser Lys
    210                 215                 220

Lys Leu Cys Pro Ile Asp Met Leu Trp Asp Asn Thr Lys Cys Lys Cys
225                 230                 235                 240

Val Leu Gln Asp Glu Thr Pro Leu Pro Gly Thr Glu Asp His Ser Tyr
                245                 250                 255

Leu Gln Glu Pro Thr Leu Cys Gly Pro His Met Thr Phe Asp Glu Asp
            260                 265                 270

Arg Cys Glu Cys Val Cys Lys Ala Pro Cys Pro Gly Asp Leu Ile Gln
        275                 280                 285
```

```
His Pro Glu Asn Cys Ser Cys Phe Glu Cys Lys Glu Ser Leu Glu Ser
    290                 295                 300

Cys Cys Gln Lys His Lys Ile Phe His Pro Asp Thr Cys Ser Cys Glu
305                 310                 315                 320

Asp Arg Cys Pro Phe His Thr Arg Thr Cys Ala Ser Arg Lys Pro Ala
                325                 330                 335

Cys Gly Lys His Trp Arg Phe Pro Lys Glu Thr Arg Ala Gln Gly Leu
                340                 345                 350

Tyr Ser Gln Glu Asn Pro
        355
```

<210> SEQ ID NO 7
<211> LENGTH: 1135
<212> TYPE: DNA
<213> ORGANISM: Mus musculus

<400> SEQUENCE: 7

```
aaactttgct tctggagaat gccttttgca acacttttca gtagctgcct ggaaacaact    60
gcttagtcat cggtagacat ttaaaatatt caaaatgtat ggagaatggg gaatggggaa   120
tatcctcatg atgttccatg tgtacttggt gcagggcttc aggagcgaac atggaccagt   180
gaagcgatca tcccggtcca tgttggaacg atctgaacaa cagatccgag cagcttctag   240
tttggaggag ttgctgcaaa tcgcgcactc tgaggactgg aagctgtggc gatgccggtt   300
gaagctcaaa agtcttgcca gtatggactc acgctcagca tcccatcgct ccaccagatt   360
tgcggcaact ttctatgaca ctgaaacact aaaagttata gatgaagaat ggcagaggac   420
ccaatgcagc cctagagaga catgcgtaga agtcgccagt gagctgggga agacaaccaa   480
cacattcttc aagccccccct gtgtaaatgt cttccggtgt ggaggctgct gcaacgaaga   540
gggtgtgatg tgtatgaaca caagcacctc ctacatctcc aaacagctct ttgagatatc   600
agtgcctctg acatcagtgc cgagttagt gcctgttaaa attgccaacc atacgggttg   660
taagtgcttg cccacgggcc ccgccatcc ttactcaatt atcagaagat ccattcagac   720
cccagaagaa gatgaatgtc ctcattccaa gaaactctgt cctattgaca tgctgtggga   780
taacaccaaa tgtaaatgtg ttttgcaaga cgagactcca ctgcctggga cagaagacca   840
ctcttacctc caggaaccca ctctctgtgg accgcacatg acgtttgatg aagatcgctg   900
tgagtgcgtc tgtaaagcac catgtccggg agatctcatt cagcacccgg aaaactgcag   960
ttgctttgag tgcaaagaaa gtctggagag ctgctgccaa aagcacaaga ttttcacccc  1020
agacacctgc aggtcaatgg tcttttcgct ttcccttaa cttggtttac tgatgacatt  1080
taaaggacat actaatctga tctgttcagg ctcttttctc tcagagtcca agcac       1135
```

<210> SEQ ID NO 8
<211> LENGTH: 321
<212> TYPE: PRT
<213> ORGANISM: Mus musculus

<400> SEQUENCE: 8

```
Met Tyr Gly Glu Trp Gly Met Gly Asn Ile Leu Met Met Phe His Val
1               5                   10                  15

Tyr Leu Val Gln Gly Phe Arg Ser Glu His Gly Pro Val Lys Arg Ser
                20                  25                  30

Ser Arg Ser Met Leu Glu Arg Ser Glu Gln Gln Ile Arg Ala Ala Ser
            35                  40                  45

Ser Leu Glu Glu Leu Leu Gln Ile Ala His Ser Glu Asp Trp Lys Leu
```

```
            50                  55                  60
Trp Arg Cys Arg Leu Lys Leu Lys Ser Leu Ala Ser Met Asp Ser Arg
 65                  70                  75                  80

Ser Ala Ser His Arg Ser Thr Arg Phe Ala Ala Thr Phe Tyr Asp Thr
                 85                  90                  95

Glu Thr Leu Lys Val Ile Asp Glu Glu Trp Gln Arg Thr Gln Cys Ser
            100                 105                 110

Pro Arg Glu Thr Cys Val Glu Val Ala Ser Glu Leu Gly Lys Thr Thr
            115                 120                 125

Asn Thr Phe Phe Lys Pro Pro Cys Val Asn Val Phe Arg Cys Gly Gly
130                 135                 140

Cys Cys Asn Glu Glu Gly Val Met Cys Met Asn Thr Ser Thr Ser Tyr
145                 150                 155                 160

Ile Ser Lys Gln Leu Phe Glu Ile Ser Val Pro Leu Thr Ser Val Pro
                165                 170                 175

Glu Leu Val Pro Val Lys Ile Ala Asn His Thr Gly Cys Lys Cys Leu
            180                 185                 190

Pro Thr Gly Pro Arg His Pro Tyr Ser Ile Ile Arg Arg Ser Ile Gln
            195                 200                 205

Thr Pro Glu Glu Asp Glu Cys Pro His Ser Lys Lys Leu Cys Pro Ile
210                 215                 220

Asp Met Leu Trp Asp Asn Thr Lys Cys Lys Cys Val Leu Gln Asp Glu
225                 230                 235                 240

Thr Pro Leu Pro Gly Thr Glu Asp His Ser Tyr Leu Gln Glu Pro Thr
                245                 250                 255

Leu Cys Gly Pro His Met Thr Phe Asp Glu Asp Arg Cys Glu Cys Val
            260                 265                 270

Cys Lys Ala Pro Cys Pro Gly Asp Leu Ile Gln His Pro Glu Asn Cys
            275                 280                 285

Ser Cys Phe Glu Cys Lys Glu Ser Leu Glu Ser Cys Cys Gln Lys His
            290                 295                 300

Lys Ile Phe His Pro Asp Thr Cys Arg Ser Met Val Phe Ser Leu Ser
305                 310                 315                 320

Pro

<210> SEQ ID NO 9
<211> LENGTH: 5
<212> TYPE: PRT
<213> ORGANISM: Mus musculus

<400> SEQUENCE: 9

Asp Phe Ser Phe Glu
 1               5

<210> SEQ ID NO 10
<211> LENGTH: 27
<212> TYPE: DNA
<213> ORGANISM: Artificial sequence
<220> FEATURE:
<223> OTHER INFORMATION: Synthetic primer

<400> SEQUENCE: 10
atgaaatgca gctgggtcat sttcttc                                          27

<210> SEQ ID NO 11
<211> LENGTH: 25
<212> TYPE: DNA
```

```
<213> ORGANISM: Artificial sequence
<220> FEATURE:
<223> OTHER INFORMATION: Synthetic primer

<400> SEQUENCE: 11
atgggatgga gctratcats ytctt                                          25

<210> SEQ ID NO 12
<211> LENGTH: 27
<212> TYPE: DNA
<213> ORGANISM: Artificial sequence
<220> FEATURE:
<223> OTHER INFORMATION: Synthetic primer

<400> SEQUENCE: 12
atgaagwtgt ggttaaactg ggttttt                                        27

<210> SEQ ID NO 13
<211> LENGTH: 24
<212> TYPE: DNA
<213> ORGANISM: Artificial sequence
<220> FEATURE:
<223> OTHER INFORMATION: Synthetic primer

<400> SEQUENCE: 13
atgractttg wytcagcttg rttt                                           24

<210> SEQ ID NO 14
<211> LENGTH: 28
<212> TYPE: DNA
<213> ORGANISM: Artificial sequence
<220> FEATURE:
<223> OTHER INFORMATION: Synthetic primer

<400> SEQUENCE: 14
atggactcca ggctcaamag ttttcctt                                       28

<210> SEQ ID NO 15
<211> LENGTH: 27
<212> TYPE: DNA
<213> ORGANISM: Artificial sequence
<220> FEATURE:
<223> OTHER INFORMATION: Synthetic primer

<400> SEQUENCE: 15
atggctgtcy trgsgctrct cttctgc                                        27

<210> SEQ ID NO 16
<211> LENGTH: 26
<212> TYPE: DNA
<213> ORGANISM: Artificial sequence
<220> FEATURE:
<223> OTHER INFORMATION: Synthetic primer

<400> SEQUENCE: 16
atggratgga gckggrtctt tmtctt                                         26

<210> SEQ ID NO 17
<211> LENGTH: 23
<212> TYPE: DNA
<213> ORGANISM: Artificial sequence
<220> FEATURE:
<223> OTHER INFORMATION: Synthetic primer

<400> SEQUENCE: 17
atgagagtgc tgattctttt gtg                                            23
```

<210> SEQ ID NO 18
<211> LENGTH: 30
<212> TYPE: DNA
<213> ORGANISM: Artificial sequence
<220> FEATURE:
<223> OTHER INFORMATION: Synthetic primer

<400> SEQUENCE: 18
atggmttggg tgtggamctt gctattcctg                                    30

<210> SEQ ID NO 19
<211> LENGTH: 27
<212> TYPE: DNA
<213> ORGANISM: Artificial sequence
<220> FEATURE:
<223> OTHER INFORMATION: Synthetic primer

<400> SEQUENCE: 19
atgggcagac ttacattctc attcctg                                       27

<210> SEQ ID NO 20
<211> LENGTH: 28
<212> TYPE: DNA
<213> ORGANISM: Artificial sequence
<220> FEATURE:
<223> OTHER INFORMATION: Synthetic primer

<400> SEQUENCE: 20
atggattttg ggctgatttt ttttattg                                      28

<210> SEQ ID NO 21
<211> LENGTH: 27
<212> TYPE: DNA
<213> ORGANISM: Artificial sequence
<220> FEATURE:
<223> OTHER INFORMATION: Synthetic primer

<400> SEQUENCE: 21
atgatggtgt taagtcttct gtacctg                                       27

<210> SEQ ID NO 22
<211> LENGTH: 30
<212> TYPE: DNA
<213> ORGANISM: Artificial sequence
<220> FEATURE:
<223> OTHER INFORMATION: Synthetic primer

<400> SEQUENCE: 22
atgaagttgc ctgttaggct gttggtgctg                                    30

<210> SEQ ID NO 23
<211> LENGTH: 29
<212> TYPE: DNA
<213> ORGANISM: Artificial sequence
<220> FEATURE:
<223> OTHER INFORMATION: Synthetic primer

<400> SEQUENCE: 23
atggagwcag acacactcct gytatgggt                                     29

<210> SEQ ID NO 24
<211> LENGTH: 30
<212> TYPE: DNA
<213> ORGANISM: Artificial sequence
<220> FEATURE:

<223> OTHER INFORMATION: Synthetic primer

<400> SEQUENCE: 24
atgagtgtgc tcactcaggt cctggsgttg                               30

<210> SEQ ID NO 25
<211> LENGTH: 33
<212> TYPE: DNA
<213> ORGANISM: Artificial sequence
<220> FEATURE:
<223> OTHER INFORMATION: Synthetic primer

<400> SEQUENCE: 25
atgaggrccc ctgctcagwt tyttggmwtc ttg                           33

<210> SEQ ID NO 26
<211> LENGTH: 30
<212> TYPE: DNA
<213> ORGANISM: Artificial sewuence
<220> FEATURE:
<223> OTHER INFORMATION: Synthetic primer

<400> SEQUENCE: 26
atggatttwc aggtgcagat twtcagcttc                               30

<210> SEQ ID NO 27
<211> LENGTH: 27
<212> TYPE: DNA
<213> ORGANISM: Artificial sequence
<220> FEATURE:
<223> OTHER INFORMATION: Synthetic primer

<400> SEQUENCE: 27
atgaggtkcy ytgytsagyt yctgrgg                                  27

<210> SEQ ID NO 28
<211> LENGTH: 31
<212> TYPE: DNA
<213> ORGANISM: Artificial sequence
<220> FEATURE:
<223> OTHER INFORMATION: Synthetic primer

<400> SEQUENCE: 28
atgggcwtca agatggagtc acakwyycwg g                             31

<210> SEQ ID NO 29
<211> LENGTH: 31
<212> TYPE: DNA
<213> ORGANISM: Artificial sequence
<220> FEATURE:
<223> OTHER INFORMATION: Synthetic primer

<400> SEQUENCE: 29
atgtggggay ctktttycmm tttttcaatt g                             31

<210> SEQ ID NO 30
<211> LENGTH: 25
<212> TYPE: DNA
<213> ORGANISM: Artificial sequence
<220> FEATURE:
<223> OTHER INFORMATION: Synthetic primer

<400> SEQUENCE: 30
atggtrtccw casctcagtt ccttg                                    25

<210> SEQ ID NO 31
<211> LENGTH: 27
<212> TYPE: DNA
<213> ORGANISM: Artificial sequence
<220> FEATURE:
<223> OTHER INFORMATION: Synthetic primer

<400> SEQUENCE: 31
atgtatatat gtttgttgtc tatttct                                27

<210> SEQ ID NO 32
<211> LENGTH: 28
<212> TYPE: DNA
<213> ORGANISM: Artificial sequence
<220> FEATURE:
<223> OTHER INFORMATION: Synthetic primer

<400> SEQUENCE: 32
atggaagccc cagctcagct tctcttcc                               28

<210> SEQ ID NO 33
<211> LENGTH: 27
<212> TYPE: DNA
<213> ORGANISM: Artificial sequence
<220> FEATURE:
<223> OTHER INFORMATION: Synthetic primer

<400> SEQUENCE: 33
atgaagtttc cttctcaact tctgctc                                27

<210> SEQ ID NO 34
<211> LENGTH: 17
<212> TYPE: DNA
<213> ORGANISM: Artificial sequence
<220> FEATURE:
<223> OTHER INFORMATION: Synthetic primer

<400> SEQUENCE: 34
tggatggtgg gaagatg                                           17

<210> SEQ ID NO 35
<211> LENGTH: 18
<212> TYPE: DNA
<213> ORGANISM: Artificial sequence
<220> FEATURE:
<223> OTHER INFORMATION: Synthetic primer

<400> SEQUENCE: 35
ccagtggata gacagatg                                          18

<210> SEQ ID NO 36
<211> LENGTH: 396
<212> TYPE: DNA
<213> ORGANISM: Mus musculus

<400> SEQUENCE: 36
atgaagttgc ctgttaggct gttggtgctg atgttctgga ttcctgcttc cagcagtgat      60
tttgtgatga cccaaactcc actctccctg cctgtcagtc ttggagatca agcctccatc     120
tcttgcagat ctagtcagag ccttgtacac agtaatggaa acacctattt acattggtac     180
ctgcagaagc caggccagtc tccaaagctc ctgatctaca aagtttccaa ccgatttttct    240 ggggtcccag acaggttcag tgcagtgga tcagggacag atttcacact caagatcagc      300
agagtggagg ctgaggatct gggagtttat ttctgctctc aaagtacaca tgttcctcgg     360
acgttcggtg gaggcaccaa gctggaaatc aaacgt                                    396

<210> SEQ ID NO 37
<211> LENGTH: 132
<212> TYPE: PRT
<213> ORGANISM: Mus musculus

<400> SEQUENCE: 37

Met Lys Leu Pro Val Arg Leu Leu Val Leu Met Phe Trp Ile Pro Ala
1               5                   10                  15

Ser Ser Ser Asp Phe Val Met Thr Gln Thr Pro Leu Ser Leu Pro Val
            20                  25                  30

Ser Leu Gly Asp Gln Ala Ser Ile Ser Cys Arg Ser Ser Gln Ser Leu
        35                  40                  45

Val His Ser Asn Gly Asn Thr Tyr Leu His Trp Tyr Leu Gln Lys Pro
    50                  55                  60

Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Phe Cys
            100                 105                 110

Ser Gln Ser Thr His Val Pro Arg Thr Phe Gly Gly Gly Thr Lys Leu
        115                 120                 125

Glu Ile Lys Arg
    130

<210> SEQ ID NO 38
<211> LENGTH: 421
<212> TYPE: DNA
<213> ORGANISM: Mus musculus

<400> SEQUENCE: 38
atgggatgga gcggggtctt tctcttcctc ctgtcaggaa gtacaggtgt ccactctgag     60
atccagctac agcagtctgg acctgacctg gtgaagcctg ggcttcggt gaaggtatcc    120
tgcagggctt ctggttactc attcactggc tacaacatgt actgggtgaa gcagagccat    180
ggaaagagcc ttgagtggat tgatatatt gatccttaca atggtgatac tacctacaac    240
cagaagttca aggcaaggc cacattgact gttgacaagt cctccagcac agccttcatg    300
catctcaaca gcctgacatc tgaggactct gcagtctatt actgtgcaag gacctcctat    360
tatggaggta tggactactg gggtcaagga acctcagtca ccgtctcctc agcaggtgag    420
t                                                                    421

<210> SEQ ID NO 39
<211> LENGTH: 137
<212> TYPE: PRT
<213> ORGANISM: Mus musculus

<400> SEQUENCE: 39

Met Gly Trp Ser Gly Val Phe Leu Phe Leu Leu Ser Gly Ser Thr Gly
1               5                   10                  15

Val His Ser Glu Ile Gln Leu Gln Gln Ser Gly Pro Asp Leu Val Lys
            20                  25                  30

Pro Gly Ala Ser Val Lys Val Ser Cys Arg Ala Ser Gly Tyr Ser Phe
        35                  40                  45

Thr Gly Tyr Asn Met Tyr Trp Val Lys Gln Ser His Gly Lys Ser Leu

```
              50                  55                  60
Glu Trp Ile Gly Tyr Ile Asp Pro Tyr Asn Gly Asp Thr Thr Tyr Asn
 65                  70                  75                  80

Gln Lys Phe Lys Gly Lys Ala Thr Leu Thr Val Asp Lys Ser Ser Ser
                 85                  90                  95

Thr Ala Phe Met His Leu Asn Ser Leu Thr Ser Glu Asp Ser Ala Val
                100                 105                 110

Tyr Tyr Cys Ala Arg Thr Ser Tyr Gly Gly Met Asp Tyr Trp Gly
                115                 120                 125

Gln Gly Thr Ser Val Thr Val Ser Ser
    130                 135

<210> SEQ ID NO 40
<211> LENGTH: 9
<212> TYPE: DNA
<213> ORGANISM: Artificial sequence
<220> FEATURE:
<223> OTHER INFORMATION: Synthetic primer

<400> SEQUENCE: 40 gccgccacc                                                              9

<210> SEQ ID NO 41
<211> LENGTH: 34
<212> TYPE: DNA
<213> ORGANISM: Artificial sequence
<220> FEATURE:
<223> OTHER INFORMATION: Synthetic primer

<400> SEQUENCE: 41
cgggccatgg cggaagtgaa gctggtggag tctg                                 34

<210> SEQ ID NO 42
<211> LENGTH: 41
<212> TYPE: DNA
<213> ORGANISM: Artificial sequence
<220> FEATURE:
<223> OTHER INFORMATION: Synthetic primer

<400> SEQUENCE: 42
cagaggatcc actcacctga agagacggtg accagagtcc c                         41

<210> SEQ ID NO 43
<211> LENGTH: 33
<212> TYPE: DNA
<213> ORGANISM: Artificial sequence
<220> FEATURE:
<223> OTHER INFORMATION: Synthetic primer

<400> SEQUENCE: 43
cgggccatgg acattgtgat gacccagtct caa                                  33

<210> SEQ ID NO 44
<211> LENGTH: 40
<212> TYPE: DNA
<213> ORGANISM: Artificial sequence
<220> FEATURE:
<223> OTHER INFORMATION: Synthetic primer

<400> SEQUENCE: 44
gatggatcca ctcacgtttt acttccaact ttgtccccga                           40

<210> SEQ ID NO 45
```

<211> LENGTH: 6515
<212> TYPE: DNA
<213> ORGANISM: Homo sapiens

<400> SEQUENCE: 45

```
ggcgtaatct gctgcttgca acaaaaaaaa ccaccgctac cagcggtggt ttgtttgccg      60
gatcaagagc taccaactct ttttccgaag gtaactggct tcagcagagc gcagatacca     120
aatactgtcc ttctagtgta gccgtagtta ggccaccact tcaagaactc tgtagcaccg     180
cctacatacc tcgctctgct aatcctgtta ccagtggctg ctgccagtgg cgataagtcg     240
tgtcttaccg ggttggactc aagacgatag ttaccggata aggcgcagcg gtcgggctga     300
acggggggtt cgtgcacaca gcccagcttg gagcgaacga cctacaccga actgagatac     360
ctacagcgtg agcattgaga aagcgccacg cttcccgaag ggagaaaggc ggacaggtat     420
ccggtaagcg gcagggtcgg aacaggagag cgcacgaggg agcttccagg gggaaacgcc     480
tggtatcttt atagtcctgt cgggtttcgc cacctctgac ttgagcgtcg attttttgtga    540
tgctcgtcag ggggggcggag cctatggaaa aacgccagca acgcaagcta gagtttaaac     600
ttgacagatg agacaataac cctgataaat gcttcaataa tattgaaaaa ggaaaagtat     660
gagtattcaa catttccgtg tcgcccttat tcccttttttt gcggcatttt gccttcctgt     720
ttttgctcac ccagaaacgc tggtgaaagt aaaagatgca gaagatcact tgggtgcgcg     780
agtgggttac atcgaactgg atctcaacag cggtaagatc cttgagagtt tcgccccga     840
agaacgtttc ccaatgatga gcacttttaa agttctgcta tgtggcgcgg tattatcccg     900
tattcttggt tgaatactca ccagtcacag aaaagcatct tacggatggc atgacagtaa     960
gagaattatg cagtgctgcc ataaccatga gtgataacac tgcggccaac ttacttctga    1020
caactatcgg aggaccgaag gagctaaccg cttttttgca acatggggg gatcatgtaa     1080
ctcgccttga tcgttgggaa ccggagctga atgaagccat accaaacgac gagcgtgaca    1140
ccacgatgcc tgtagcaatg gcaacaacgt tgcgaaaact attaactggc gaactactta    1200
ctctagcttc ccggcaacaa ctaatagact ggatggaggc ggataaagtt gcaggaccac    1260
ttctgcgctc ggcacttccg gctggctggt ttattgctga taaatcagga gccggtgagc    1320
gtgggtcacg cggtatcatt gcagcactgg ggccggatgg taagccctcc cgtatcgtag    1380
ttatctacac tacggggagt caggcaacta tggatgaacg aaatagacag atcgctgaga    1440
taggtgcctc actgattaag cattggtaag gataaatttc tggtaaggag gacacgtatg    1500
gaagtgggca agttggggaa gccgtatccg ttgctgaatc tggcatatgt gggagtataa    1560
gacgcgcagc gtcgcatcag gcattttttt ctgcgccaat gcaaaaaggc catccgtcag    1620
gatggccttt cgcataacta gtgaggctcc ggtgcccgtc agtgggcaga gcgcacatcg    1680
cccacagtcc ccgagaagtt gggggaggg gtcggcaatt gaaccggtgc ctagagaagg    1740
tggcgcgggg taaactggga aagtgatgtc gtgtactggc tccgcctttt tcccgagggt    1800
gggggagaac cgtatataag tgcagtagtc gccgtgaacg ttcttttttcg caacgggttt    1860
gccgccagaa cacaggtaag tgccgtgtgt ggttcccgcg ggcctggcct ctttacgggt    1920
tatggccctt gcgtgccttg aattacttcc cgcccctggc tgcagtacgt gattcttgat    1980
cccgagcttc gggttggaag tgggtgggag agttcgaggc cttgcgctta aggagcccct    2040
tcgcctcgtg cttgagttga ggcctggcct gggcgctggg gccgccgcgt gcgaatctgg    2100
tggcaccttc gcgcctgtct cgctgctttc gataagtctc tagccattta aaattttttga   2160
tgacctgctg cgacgctttt tttctggcaa gatagtcttg taaatgcggg ccaagatcga    2220
```

```
tctgcacact ggtatttcgg tttttggggc cgcgggcggc gacggggccc gtgcgtccca    2280
gcgcacatgt tcggcgaggc ggggcctgcg agcgcggcca ccgagaatcg gacgggggta    2340
gtctcaagct ggccggcctg ctctggtgcc tggcctcgcg ccgccgtgta tcgccccgcc    2400
ctgggcggca aggctggccc ggtcggcacc agttgcgtga gcggaaagat ggccgcttcc    2460
cggccctgct gcagggagct caaaatggag gacgcggcgc tcgggagagc gggcgggtga    2520
gtcacccaca caaaggaaaa gggcctttcc gtcctcagcc gtcgcttcat gtgactccac    2580
ggagtaccgg gcgccgtcca ggcacctcga ttagttctcg agcttttgga gtacgtcgtc    2640
tttaggttgg ggggagggt tttatgcgat ggagtttccc cacactgagt gggtggagac    2700
tgaagttagg ccagcttggc acttgatgta attctccttg gaatttgccc tttttgagtt    2760
tggatcttgg ttcattctca agcctcagac agtggttcaa agttttttc ttccatttca    2820
ggtgtcgtga aaagcttgga tccatctggg ataagcatgc tgttttctgt ctgtccctaa    2880
catgccctgt gattatgcgc aaacaacaca cccaagggca gaactttgtt acttaaacac    2940
catcctgttt gcttctttcc tcaggaactg tggctgcacc atctgtcttc atcttcccgc    3000
catctgatga gcagttgaaa tctggaactg cctctgttgt gtgcctgctg ataacttct    3060
atcccagaga ggccaaagta cagtggaagg tggataacgc cctccaatcg ggtaactccc    3120
aggagagtgt cacagagcag gacagcaagg acagcaccta cagcctcagc agcaccctga    3180
cgctgagcaa agcagactac gagaaacaca agtctacgc ctgcgaagtc acccatcagg    3240
gcctgagctc gcccgtcaca aagagcttca caggggaga gtgttgagcg gccgcaggta    3300
agccagccca ggcctcgccc tccagctcaa ggccgggaca ggtgccctag agtagcctgc    3360
atccaggac aggccccagc cgggtgctga cacgtccacc tccatctctt cctcaggtct    3420
gcccgggtgg catccctgtg acccctcccc agtgcctctc ctggccctgg aagttgccac    3480
tccagtgccc accagccttg tcctaataaa attaagttgc atcattttgt ctgactaggt    3540
gtccttctat aatattatgg ggtggagggg ggtggtatgg agcaaggggc ccaagttaac    3600
ttgtttattg cagcttataa tggttacaaa taaagcaata gcatcacaaa tttcacaaat    3660
aaagcatttt tttcactgca ttctagttgt ggtttgtcca aactcatcaa tgtatcttat    3720
catgtctgga tctgcttcag gcaccgggct tgcgggtcat gcaccaggtc gcgcggtcct    3780
tcgggcactc gacgtcggcg gtgacggtga agccgagccg ctcgtagaag gggaggttgc    3840
ggggcgcgga ggtctccagg aaggcgggca ccccggcgcg ctcggccgcc tccactccgg    3900
ggagcacgac ggcgctgccc agacccttgc cctggtggtc gggcgagacg ccgacggtgg    3960
ccaggaacca cgcgggctcc ttgggccggt gcggcgccag gaggcttcc atctgttgct    4020
gcgcggccag ccgggaaccg ctcaactcgg ccatgcgcgg gccgatctcg gcgaacaccg    4080
cccccgcttc gacgctctcc ggcgtggtcc agaccgccac cgcggcgccg tcgtccgcga    4140
cccacacctt gccgatgtcg agcccgacgc gcgtgaggaa gagttcttgc agctcggtga    4200
cccgctcgat gtggcggtcc gggtcgacgg tgtggcgcgt ggcggggtag tcggcgaacg    4260
cggcggcgag ggtgcgtacg gccgcgggga cgtcgtcgcg ggtggcgagg cgcaccgtgg    4320
gcttgtactc ggtcatggtg gcctgcagag tcgctcggtg ttcgaggcca cacgcgtcac    4380
cttaatatgc gaagtggacc tgggaccgcg ccgccccgac tgcatctgcg tgttaattcg    4440
ccaatgacaa gacgctgggc ggggtttgtg tcatcataga actaaagaca tgcaaatata    4500
tttcttccgg ggacaccgcc agcaaacgcg agcaacgggc cacgggatg aagcagctgc    4560
```

```
gccactccct gaagatccat cgtctcctaa caagttacat cactcctgcc cttcctcacc    4620
ctcatctcca tcacctcctt catctccgtc atctccgtca tcaccctccg cggcagcccc    4680
ttccaccata ggtggaaacc agggaggcaa atctactcca tcgtcaaagc tgcacacagt    4740
caccctgata ttgcaggtag gagcgggctt tgtcataaca aggtccttaa tcgcatcctt    4800
caaaacctca gcaaatatat gagttttgtaa aagaccatg aaataacaga caatggactc    4860
ccttagcggg ccaggttgtg ggccgggtcc aggggccatt ccaaagggga gacgactcaa    4920
tggtgtaaga cgacattgtg gaatagcaag ggcagttcct cgccttaggt tgtaaaggga    4980
ggtcttacta cctccatata cgaacacacc ggcgacccaa gttccttcgt cggtagtcct    5040
ttctacgtga ctcctagcca ggagagctct taaaccttct gcaatgttct caaatttcgg    5100
gttggaacct ccttgaccac gatgctttcc aaaccaccct ccttttttgc gcctgcctcc    5160
atcaccctga ccccgctgc gcgggggcac gtcaggctca ccatctgggc cgccttcttg    5220
gtggtattca aaataatcgg cttcccctac agggtggaaa aatggccttc tacctggagg    5280
gggcctgcgc ggtggagacc cggatgatga tgactgacta ctgggactcc tgggcctctt    5340
ttctccacgt ccacgacctc tccccctggc tctttcacga cttccccccc tggctctttc    5400
acgtcctcta ccccggcggc ctccactacc tcctcgaccc cggcctccac tacctcctcg    5460
accccggcct ccactgcctc ctcgaccccg gcctccacct cctgctcctg ccctcccgc    5520 tcctgctcct gctcctgttc caccgtgggt ccctttgcag ccaatgcaac ttggacgttt    5580 ttgggggtctc cggacaccat ctctatgtct tggccctgat cctgagccgc ccggggctcc    5640
tggtcttccg cctcctcgtc ctcgtcctct ccccgtcct cgtccatgtg ccatgatggc    5700
ggcctgcagc tgtgttcgag gccgcgcgtg tcaccttaat atgcgaagtg gacctgggac    5760
cgcgccgccc cgactgcatc tgcgtgttcg agttcgccaa tgacaagacg ctgggcgggg    5820 agatcccccct tattaaccct aaacgggtag catatgcttc ccgggtagta gtatatacta    5880
tccagactaa ccctaattca atagcatatg ttacccaacg ggaagcatat gctatcgaat    5940
tagggttagt aaaagggtcc taaggaacag cgatctggat agcatatgct atcctaatct    6000
atatctgggt agcatatgct atcctaatct atatctgggt agcataggct atcctaatct    6060
atatctgggt agcatatgct atcctaatct atatctgggt agtatatgct atcctaattt    6120
atatctgggt agcataggct atcctaatct atatctgggt agcatatgct atcctaatct    6180
atatctgggt agtatatgct atcctaatct gtatccgggt agcatatgct atcctcatgc    6240
atatacagtc agcatatgat acccagtagt agagtgggag tgctatcctt tgcatatgcc    6300
gccacctccc aaggagatct gtcgacatcg atgggcgcgg tgtacactc cgcccatccc    6360 gcccctaact ccgcccagtt ccgcccattc tccgcctcat ggctgactaa tttttttat    6420 ttatgcagag gccgaggccg cctcggcctc tgagctattc cagaagtagt gaggaggctt    6480
ttttggaggc ctaggctttt gcaaaaagct aattc                              6515
```

<210> SEQ ID NO 46
<211> LENGTH: 7122
<212> TYPE: DNA
<213> ORGANISM: Homo sapiens

<400> SEQUENCE: 46

```
ggcgtaatct gctgcttgca acaaaaaaaa ccaccgctac cagcggtggt ttgtttgccg      60
gatcaagagc taccaactct ttttccgaag gtaactggct tcagcagagc gcagatacca     120
aatactgtcc ttctagtgta gccgtagtta ggccaccact tcaagaactc tgtagcaccg     180
```

```
cctacatacc tcgctctgct aatcctgtta ccagtggctg ctgccagtgg cgataagtcg    240
tgtcttaccg ggttggactc aagacgatag ttaccggata aggcgcagcg gtcgggctga    300 acgggggggtt cgtgcacaca gcccagcttg gagcgaacga cctacaccga actgagatac    360
ctacagcgtg agcattgaga aagcgccacg cttcccgaag ggagaaaggc ggacaggtat    420
ccggtaagcg gcagggtcgg aacaggagag cgcacgaggg agcttccagg gggaaacgcc    480
tggtatcttt atagtcctgt cgggtttcgc cacctctgac ttgagcgtcg attttttgtga   540 tgctcgtcag gggggcggag cctatggaaa aacgccagca acgcaagcta gagtttaaac    600
ttgacagatg agacaataac cctgataaat gcttcaataa tattgaaaaa ggaaaagtat    660
gagtattcaa catttccgtg tcgcccttat tcccttttttt gcggcatttt gccttcctgt    720
ttttgctcac ccagaaacgc tggtgaaagt aaaagatgca gaagatcact tgggtgcgcg    780
agtgggttac atcgaactgg atctcaacag cggtaagatc cttgagagtt ttcgccccga    840
agaacgtttc ccaatgatga gcacttttaa agttctgcta tgtggcgcgg tattatcccg    900
tattcttggt tgaatactca ccagtcacag aaaagcatct tacgatggc atgcagtaa     960 gagaattatg cagtgctgcc ataaccatga gtgataacac tgcggccaac ttacttctga    1020
caactatcgg aggaccgaag gagctaaccg cttttttgca caacatgggg gatcatgtaa    1080
ctcgccttga tcgttgggaa ccggagctga atgaagccat accaaacgac gagcgtgaca    1140
ccacgatgcc tgtagcaatg gcaacaacgt tgcgaaaact attaactggc gaactactta    1200
ctctagcttc ccggcaacaa ctaatagact ggatggaggc ggataaagtt gcaggaccac    1260
ttctgcgctc ggcacttccg gctggctggt ttattgctga taaatcagga gccggtgagc    1320
gtgggtcacg cggtatcatt gcagcactgg ggccggatgg taagccctcc cgtatcgtag    1380
ttatctacac tacggggagt caggcaacta tggatgaacg aaatagacag atcgctgaga    1440
taggtgcctc actgattaag cattggtaag gataaatttc tggtaaggag gacacgtatg    1500
gaagtgggca agttggggaa gccgtatccg ttgctgaatc tggcatatgt gggagtataa    1560
gacgcgcagc gtcgcatcag gcattttttt ctgcgccaat gcaaaaaggc catccgtcag    1620
gatggccttt cgcataacta gtgaggctcc ggtgcccgtc agtgggcaga gcgcacatcg    1680
cccacagtcc ccgagaagtt gggggagggg gtcggcaatt gaaccggtgc ctagagaagg    1740
tggcgcgggg taaactggga aagtgatgtc gtgtactggc tccgcttttt tcccgagggt    1800
gggggagaac cgtatataag tgcagtagtc gccgtgaacg ttcttttttcg caacgggttt    1860 gccgccagaa cacaggtaag tgccgtgtgt ggttcccgcg ggcctggcct ctttacgggt    1920
tatgcccttt gcgtgccttg aattacttcc cgccccctggc tgcagtacgt gattcttgat    1980
cccgagcttc gggttggaag tgggtgggag agttcgaggc cttgcgctta aggagcccct    2040
tcgcctcgtg cttgagttga ggcctggcct gggcgctggg gccgccgcgt gcgaatctgg    2100
tggcaccttc gcgcctgtct cgctgctttc gataagtctc tagccattta aaatttttga    2160
tgacctgctg cgacgctttt tttctggcaa gatagtcttg taaatgcggg ccaagatcga    2220
tctgcacact ggtatttcgg ttttttgggc gcgggcggc gacggggccc gtgcgtccca    2280
gcgcacatgt tcggcgaggc ggggcctgcg agcgcggcca ccgagaatcg gacggggta    2340 gtctcaagct ggccggcctg ctctggtgcc tggcctcgcg ccgccgtgta tcgccccgcc    2400
ctgggcggca aggctggccc ggtcggcacc agttgcgtga gcggaaagat ggccgcttcc    2460
cggccctgct gcagggagct caaaatggag gacgcggcgc tcgggagagc gggcgggtga    2520
```

-continued

```
gtcacccaca caaaggaaaa gggcctttcc gtcctcagcc gtcgcttcat gtgactccac    2580
ggagtaccgg gcgccgtcca ggcacctcga ttagttctcg agcttttgga gtacgtcgtc    2640
tttaggttgg ggggaggggt tttatgcgat ggagtttccc cacactgagt gggtggagac    2700
tgaagttagg ccagcttggc acttgatgta attctccttg gaatttgccc ttttttgagtt   2760
tggatcttgg ttcattctca agcctcagac agtggttcaa agttttttttc ttccatttca   2820
ggtgtcgtga aaagcttgga tcctctgcgc ctgggcccag ctctgtccca caccgcggtc    2880
acatggcacc acctctcttg cagcctccac caagggccca tcggtcttcc ccctggcacc    2940
ctcctccaag agcacctctg ggggcacagc ggccctgggc tgcctggtca aggactactt    3000
ccccgaaccg gtgacggtgt cgtggaactc aggcgccctg accagcggcg tgcacacctt    3060
cccggctgtc ctacagtcct caggactcta ctccctcagc agcgtggtga ccgtgccctc    3120
cagcagcttg ggcacccaga cctacatctg caacgtgaat cacaagccca gcaacaccaa    3180
ggtggacaag aaagttgagc ccaaatcttg tgacaaaact cacacatgcc caccgtgccc    3240
agcacctgaa ctcctggggg gaccgtcagt cttcctcttc cccccaaaac ccaaggacac    3300
cctcatgatc tcccggaccc ctgaggtcac atgcgtggtg gtggacgtga gccacgaaga    3360
ccctgaggtc aagttcaact ggtacgtgga cggcgtggag gtgcataacg ccaagacaaa    3420
gccgcgggag gagcagtaca acagcacgta ccgggtggtc agcgtcctca ccgtcctgca    3480
ccaggactgg ctgaatggca aggagtacaa gtgcaaggtc tccaacaaag ccctcccagc    3540
ccccatcgag aaaaccatct ccaaagccaa agggcagccc cgagaaccac aggtgtacac    3600
cctgccccca tcccgggagg agatgaccaa gaaccaggtc agcctgacct gcctggtcaa    3660
aggcttctat cccagcgaca tcgccgtgga gtgggagagc aatgggcagc cggagaacaa    3720
ctacaagacc acgcctcccg tgctggactc cgacggctcc ttcttcctct acagcaagct    3780
caccgtggac aagagcaggt ggcagcaggg gaacgtcttc tcatgctccg tgatgcatga    3840
ggctctgcac aaccactaca cgcagaagag cctctccctg tctccgggta aatgagcggc    3900
cgcaggtaag ccagcccagg cctcgccctc cagctcaagg cgggacaggt gccctagagt    3960
agcctgcatc cagggacagg ccccagccgg gtgctgacac gtccacctcc atctcttcct    4020
caggtctgcc cggtggcat ccctgtgacc cctccccagt gcctctcctg gccctggaag    4080
ttgccactcc agtgcccacc agccttgtcc taataaaatt aagttgcatc attttgtctg   4140
actaggtgtc cttctataat attatggggt ggagggggt ggtatggagc aaggggccca     4200
agttaacttg tttattgcag cttataatgg ttacaaataa agcaatagca tcacaaattt   4260
cacaaataaa gcatttttt cactgcattc tagttgtggt ttgtccaaac tcatcaatgt    4320
atcttatcat gtctggatct gcttcaggca ccgggcttgc gggtcatgca ccaggtcgcg    4380
cggtccttcg ggcactcgac gtcggcggtg acggtgaagc cgagccgctc gtagaagggg    4440
aggttgcggg gcgcggaggt ctccaggaag gcggcacccc ggcgcgctc ggccgcctcc     4500
actccgggga gcacgacggc gctgcccaga cccttgccct ggtggtcggg cgagacgccg    4560
acggtggcca ggaaccacgc gggctccttg gccggtgcg cgccaggag gccttccatc      4620
tgttgctgcg cggccagccg ggaaccgctc aactcggcca tgcgcgggcc gatctcggcg    4680
aacaccgccc ccgcttcgac gctctccggc gtggtccaga ccgccaccgc ggcgcgtcg    4740
tccgcgaccc acaccttgcc gatgtcgagc ccgacgcgcg tgaggaagag ttcttgcagc    4800
tcggtgaccc gctcgatgtg gcggtccggg tcgacggtgt ggcgcgtggc ggggtagtcg    4860
gcgaacgcgg cggcgagggt gcgtacggcc cgggggacgt cgtcgcgggt ggcgaggcgc    4920
```

-continued

```
accgtgggct tgtactcggt catggtggcc tgcagagtcg ctcggtgttc gaggccacac    4980
gcgtcacctt aatatgcgaa gtggacctgg gaccgcgccg ccccgactgc atctgcgtgt    5040
taattcgcca atgacaagac gctgggcggg gtttgtgtca tcatagaact aaagacatgc    5100
aaatatattt cttccgggga caccgccagc aaacgcgagc aacgggccac ggggatgaag    5160
cagctgcgcc actccctgaa gatccatcgt ctcctaacaa gttacatcac tcctgccctt    5220
cctcaccctc atctccatca cctccttcat ctccgtcatc tccgtcatca ccctccgcgg    5280
cagcccttc caccataggt ggaaaccagg gaggcaaatc tactccatcg tcaaagctgc     5340
acacagtcac cctgatattg caggtaggag cgggctttgt cataacaagg tccttaatcg    5400
catccttcaa aacctcagca aatatatgag tttgtaaaaa gaccatgaaa taacagacaa    5460
tggactccct tagcgggcca ggttgtgggc cgggtccagg ggccattcca aaggggagac    5520
gactcaatgg tgtaagacga cattgtggaa tagcaagggc agttcctcgc cttaggttgt    5580
aaagggaggt cttactacct ccatatacga acacaccggc gacccaagtt ccttcgtcgg    5640
tagtcctttc tacgtgactc ctagccagga gagctcttaa accttctgca atgttctcaa    5700
atttcgggtt ggaacctcct tgaccacgat gctttccaaa ccaccctcct ttttttgcgcc   5760
tgcctccatc accctgaccc ccgctgcgcg ggggcacgtc aggctcacca tctgggccgc    5820
cttcttggtg gtattcaaaa taatcggctt ccctacagg gtggaaaaat ggccttctac     5880
ctggagggg cctgcgcggt ggagacccgg atgatgatga ctgactactg ggactcctgg     5940
gcctcttttc tccacgtcca cgacctctcc ccctggctct ttcacgactt ccccccctgg    6000
ctctttcacg tcctctaccc cggcggcctc cactacctcc tcgacccgg cctccactac     6060
ctcctcgacc ccgcctcca ctgcctcctc gaccccggcc tccacctcct gctcctgccc     6120
ctcccgctcc tgctcctgct cctgttccac cgtgggtccc tttgcagcca atgcaacttg    6180
gacgttttg gggtctccgg acaccatctc tatgtcttgg ccctgatcct gagccgcccg     6240
gggctcctgg tcttccgcct cctcgtcctc gtcctcttcc ccgtcctcgt ccatgtgcca    6300
tgatggcggc ctgcagctgt gttcgaggcc gcgcgtgtca ccttaatatg cgaagtggac    6360
ctgggaccgc gccgcccga ctgcatctgc gtgttcgagt tcgccaatga caagacgctg     6420
ggcggggaga tcccccttat taaccctaaa cgggtagcat atgcttcccg ggtagtagta    6480
tatactatcc agactaaccc taattcaata gcatatgtta cccaacggga agcatatgct    6540
atcgaattag ggttagtaaa agggtcctaa ggaacagcga tctggatagc atatgctatc    6600
ctaatctata tctgggtagc atatgctatc ctaatctata tctgggtagc ataggctatc    6660
ctaatctata tctgggtagc atatgctatc ctaatctata tctgggtagt atatgctatc    6720
ctaatttata tctgggtagc ataggctatc ctaatctata tctgggtagc atatgctatc    6780
ctaatctata tctgggtagt atatgctatc ctaatctgta tccgggtagc atatgctatc    6840
ctcatgcata tacagtcagc atatgatacc cagtagtaga gtgggagtgc tatcctttgc    6900
atatgccgcc acctcccaag gagatctgtc gacatcgatg ggcgcgggtg tacactccgc    6960
ccatcccgcc cctaactccg cccagttccg cccattctcc gcctcatggc tgactaattt    7020
ttttttattta tgcagaggcc gaggccgcct cggcctctga gctattccag aagtagtgag    7080
gaggcttttt tggaggccta ggcttttgca aaaagctaat tc                       7122
```

<210> SEQ ID NO 47
<211> LENGTH: 16
<212> TYPE: PRT

```
<213> ORGANISM: Mus musculus

<400> SEQUENCE: 47

Arg Ser Ser Gln Ser Leu Val His Ser Asn Gly Asn Thr Tyr Leu His
1               5                   10                  15

<210> SEQ ID NO 48
<211> LENGTH: 7
<212> TYPE: PRT
<213> ORGANISM: Mus musculus

<400> SEQUENCE: 48

Lys Val Ser Asn Arg Phe Ser
1               5

<210> SEQ ID NO 49
<211> LENGTH: 9
<212> TYPE: PRT
<213> ORGANISM: Mus musculus

<400> SEQUENCE: 49

Ser Gln Ser Thr His Val Pro Arg Thr
1               5

<210> SEQ ID NO 50
<211> LENGTH: 10
<212> TYPE: PRT
<213> ORGANISM: Mus musculus

<400> SEQUENCE: 50

Gly Tyr Ser Phe Thr Gly Tyr Asn Met Tyr
1               5                   10

<210> SEQ ID NO 51
<211> LENGTH: 17
<212> TYPE: PRT
<213> ORGANISM: Mus musculus

<400> SEQUENCE: 51

Tyr Ile Asp Pro Tyr Asn Gly Asp Thr Thr Tyr Asn Gln Lys Phe Lys
1               5                   10                  15
Gly

<210> SEQ ID NO 52
<211> LENGTH: 9
<212> TYPE: PRT
<213> ORGANISM: Mus musculus

<400> SEQUENCE: 52

Thr Ser Tyr Tyr Gly Gly Met Asp Tyr
1               5
```